US007824432B2

(12) United States Patent
Michelson

(10) Patent No.: US 7,824,432 B2
(45) Date of Patent: *Nov. 2, 2010

(54) METHOD FOR INSTALLATION OF DYNAMIC ANTERIOR CERVICAL PLATE SYSTEM HAVING MOVEABLE SEGMENTS

(75) Inventor: Gary K. Michelson, Venice, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1047 days.

This patent is subject to a terminal disclaimer.

(21) Appl. No.: 10/971,254

(22) Filed: Oct. 23, 2004

(65) Prior Publication Data

US 2005/0085816 A1 Apr. 21, 2005

Related U.S. Application Data

(62) Division of application No. 10/160,059, filed on Jun. 4, 2002, now Pat. No. 7,118,573.

(60) Provisional application No. 60/379,589, filed on May 9, 2002, provisional application No. 60/377,916, filed on May 3, 2002, provisional application No. 60/356,318, filed on Feb. 12, 2002, provisional application No. 60/355,194, filed on Feb. 8, 2002, provisional application No. 60/296,681, filed on Jun. 6, 2001, provisional application No. 60/296,680, filed on Jun. 6, 2001, provisional application No. 60/296,060, filed on Jun. 4, 2001, provisional application No. 60/296,059, filed on Jun. 4, 2001.

(51) Int. Cl.
*A61B 17/70* (2006.01)
(52) U.S. Cl. .................. 606/281; 606/71; 606/282
(58) Field of Classification Search ............ 606/61, 606/69–71
See application file for complete search history.

(56) References Cited

U.S. PATENT DOCUMENTS

| | | |
|---|---|---|
| 1,105,105 A | 7/1914 | Sherman |
| 3,604,414 A | 9/1971 | Borges |
| 3,659,595 A | 5/1972 | Haboush |
| 3,900,025 A | 8/1975 | Barnes, Jr. |
| 3,960,147 A | 6/1976 | Murray |
| 4,034,418 A | 7/1977 | Jackson et al. |
| 4,289,123 A | 9/1981 | Dunn |
| RE31,628 E | 7/1984 | Allgower et al. |

(Continued)

FOREIGN PATENT DOCUMENTS

DE 4007308 5/1991

(Continued)

OTHER PUBLICATIONS

Advertisement for Codman Anterior Cervical Plate System by Codman; Johnson & Johnson; Professional, Inc.; undated.

(Continued)

*Primary Examiner*—Eduardo C Robert
*Assistant Examiner*—Mary Hoffman
(74) *Attorney, Agent, or Firm*—Martin & Ferraro, LLP

(57) ABSTRACT

An anterior cervical plating system includes moveable plate segments to vary the overall length of the plate and allow and/or cause intersegmental compression of vertebral bodies. The plating system is capable of both passive and active dynamization and has the ability to produce the former from the latter.

42 Claims, 77 Drawing Sheets

U.S. PATENT DOCUMENTS

| | | | |
|---|---|---|---|
| 4,467,809 A | 8/1984 | Brighton | |
| 4,488,543 A | 12/1984 | Tornier | |
| 4,493,317 A | 1/1985 | Klaue | |
| 4,503,848 A | 3/1985 | Caspar et al. | |
| 4,599,086 A | 7/1986 | Doty | |
| 4,651,724 A | 3/1987 | Berentey et al. | |
| 4,743,256 A | 5/1988 | Brantigan | |
| 4,794,918 A | 1/1989 | Wolter | |
| 4,795,804 A | 1/1989 | Urist | |
| 4,936,848 A | 6/1990 | Bagby | |
| 5,034,418 A | 7/1991 | Yamagishi et al. | |
| 5,041,113 A | 8/1991 | Biedermann et al. | |
| 5,053,036 A | 10/1991 | Perren et al. | |
| 5,127,912 A | 7/1992 | Ray et al. | |
| 5,129,903 A | 7/1992 | Luhr et al. | |
| 5,147,361 A | 9/1992 | Ojima et al. | |
| 5,167,665 A | 12/1992 | McKinney | |
| 5,180,381 A | 1/1993 | Aust et al. | |
| 5,190,544 A | 3/1993 | Chapman et al. | |
| 5,209,751 A | 5/1993 | Farris et al. | |
| 5,234,431 A | 8/1993 | Keller | |
| 5,300,073 A | 4/1994 | Ray et al. | |
| 5,330,477 A | 7/1994 | Crook | |
| 5,344,421 A | 9/1994 | Crook | |
| 5,364,399 A | 11/1994 | Lowery et al. | |
| 5,397,363 A | 3/1995 | Gelbard | |
| 5,423,826 A | 6/1995 | Coates et al. | |
| 5,470,333 A | 11/1995 | Ray | |
| 5,520,690 A | 5/1996 | Errico et al. | |
| 5,531,746 A | 7/1996 | Errico et al. | |
| 5,531,747 A | 7/1996 | Ray | |
| 5,549,612 A | 8/1996 | Yapp et al. | |
| 5,558,674 A | 9/1996 | Heggeness et al. | |
| 5,569,250 A | 10/1996 | Sarver et al. | |
| 5,578,034 A | 11/1996 | Estes | |
| 5,593,409 A * | 1/1997 | Michelson | 606/61 |
| 5,601,553 A | 2/1997 | Trebing et al. | |
| 5,605,938 A * | 2/1997 | Roufa et al. | 514/59 |
| 5,607,426 A | 3/1997 | Ralph et al. | |
| 5,616,142 A | 4/1997 | Yuan et al. | |
| 5,628,781 A * | 5/1997 | Williams et al. | 623/1.39 |
| 5,643,265 A | 7/1997 | Errico et al. | |
| 5,646,142 A | 7/1997 | Dantanarayana et al. | |
| 5,662,652 A | 9/1997 | Schafer et al. | |
| 5,672,177 A | 9/1997 | Seldin | |
| 5,676,666 A | 10/1997 | Oxland et al. | |
| 5,676,703 A | 10/1997 | Gelbard | |
| 5,681,313 A | 10/1997 | Diez | |
| 5,713,900 A | 2/1998 | Benzel et al. | |
| 5,722,977 A | 3/1998 | Wilhelmy | |
| 5,728,127 A | 3/1998 | Asher et al. | |
| 5,735,853 A | 4/1998 | Olerud | |
| 5,735,899 A | 4/1998 | Schwartz et al. | |
| 5,741,258 A | 4/1998 | Klaue et al. | |
| 5,755,796 A | 5/1998 | Ibo et al. | |
| 5,766,254 A | 6/1998 | Gelbard | |
| 5,800,433 A | 9/1998 | Benzel et al. | |
| D402,032 S | 12/1998 | Stone | |
| 5,843,082 A | 12/1998 | Yuan et al. | |
| 5,865,848 A | 2/1999 | Baker | |
| 5,866,113 A * | 2/1999 | Hendriks et al. | 424/78.17 |
| D406,646 S | 3/1999 | Stone | |
| 5,876,402 A | 3/1999 | Errico | |
| 5,899,939 A * | 5/1999 | Boyce et al. | 623/16.11 |
| 5,902,304 A | 5/1999 | Walker et al. | |
| 5,904,683 A | 5/1999 | Pohndorf et al. | |
| 5,947,893 A | 9/1999 | Agrawal et al. | |
| 5,951,558 A | 9/1999 | Fiz | |
| 5,954,722 A | 9/1999 | Bono | |
| 5,954,725 A | 9/1999 | Sherman et al. | |
| 5,964,760 A | 10/1999 | Richelsoph | |
| 5,964,762 A | 10/1999 | Biedermann et al. | |
| 5,964,763 A | 10/1999 | Incavo et al. | |
| 5,968,098 A * | 10/1999 | Winslow | 623/17.11 |
| 6,022,350 A | 2/2000 | Ganem | |
| 6,030,389 A | 2/2000 | Wagner et al. | |
| 6,045,554 A | 4/2000 | Grooms et al. | |
| 6,087,555 A | 7/2000 | Dunstan et al. | |
| 6,106,527 A | 8/2000 | Wu et al. | |
| 6,106,557 A | 8/2000 | Robioneck et al. | |
| 6,117,135 A | 9/2000 | Schlapfer | |
| 6,136,001 A | 10/2000 | Michelson | |
| 6,139,316 A | 10/2000 | Sachdeva et al. | |
| 6,139,550 A | 10/2000 | Michelson | |
| 6,152,927 A | 11/2000 | Farris et al. | |
| 6,159,213 A | 12/2000 | Rogozinski | |
| 6,193,721 B1 | 2/2001 | Michelson | |
| D440,311 S | 4/2001 | Michelson | |
| 6,217,580 B1 | 4/2001 | Levin | |
| 6,224,602 B1 | 5/2001 | Hayes | |
| 6,224,607 B1 | 5/2001 | Michelson | |
| 6,228,085 B1 | 5/2001 | Theken et al. | |
| 6,235,034 B1 | 5/2001 | Bray | |
| 6,235,059 B1 | 5/2001 | Benezech et al. | |
| 6,258,089 B1 | 7/2001 | Campbell et al. | |
| 6,277,124 B1 | 8/2001 | Haag | |
| D449,692 S | 10/2001 | Michelson | |
| 6,296,647 B1 | 10/2001 | Robioneck et al. | |
| 6,302,883 B1 | 10/2001 | Bono | |
| 6,306,136 B1 | 10/2001 | Baccelli | |
| 6,328,738 B1 | 12/2001 | Suddaby | |
| 6,342,055 B1 | 1/2002 | Eisermann et al. | |
| 6,355,036 B1 | 3/2002 | Nakajima | |
| 6,383,189 B1 | 5/2002 | Schumacher | |
| 6,395,030 B1 | 5/2002 | Songer et al. | |
| 6,402,756 B1 | 6/2002 | Ralph et al. | |
| 6,406,478 B1 | 6/2002 | Kuo | |
| 6,410,519 B1 | 6/2002 | Gruskin et al. | |
| 6,413,259 B1 | 7/2002 | Lyons et al. | |
| 6,471,706 B1 * | 10/2002 | Schumacher et al. | 606/69 |
| 6,503,250 B2 | 1/2003 | Paul | |
| 6,533,786 B1 | 3/2003 | Needham et al. | |
| 6,558,686 B1 | 5/2003 | Darouiche | |
| 6,576,017 B2 | 6/2003 | Foley et al. | |
| 6,585,738 B1 | 7/2003 | Mangione et al. | |
| 6,599,290 B2 | 7/2003 | Bailey et al. | |
| 6,602,256 B1 | 8/2003 | Hayes | |
| 6,605,090 B1 | 8/2003 | Trieu et al. | |
| 6,645,208 B2 | 11/2003 | Apfelbaum et al. | |
| 6,652,525 B1 | 11/2003 | Assaker et al. | |
| 6,702,817 B2 | 3/2004 | Beger et al. | |
| 6,764,489 B2 | 7/2004 | Ferree | |
| 6,783,526 B1 | 8/2004 | Lin et al. | |
| 6,786,910 B2 | 9/2004 | Coehn et al. | |
| 6,793,658 B2 | 9/2004 | LeHuec et al. | |
| 6,855,147 B2 | 2/2005 | Harrington, Jr. | |
| 6,872,210 B2 * | 3/2005 | Hearn | 606/69 |
| 6,908,469 B2 | 6/2005 | Sellers et al. | |
| 7,112,202 B2 * | 9/2006 | Michelson | 606/71 |
| 7,115,130 B2 * | 10/2006 | Michelson | 606/71 |
| 2001/0049559 A1 | 12/2001 | Koo et al. | |
| 2002/0004660 A1 | 1/2002 | Henniges et al. | |
| 2002/0055741 A1 | 5/2002 | Schlapfer et al. | |
| 2002/0111630 A1 | 8/2002 | Ralph et al. | |
| 2002/0183754 A1 | 12/2002 | Michelson | |
| 2002/0183757 A1 | 12/2002 | Michelson | |
| 2003/0060828 A1 | 3/2003 | Michelson | |
| 2003/0229348 A1 | 12/2003 | Sevrain | |
| 2004/0167521 A1 | 8/2004 | De Windt | |
| 2004/0181226 A1 | 9/2004 | Michelson | |
| 2004/0186476 A1 | 9/2004 | Michelson | |
| 2005/0187554 A1 * | 8/2005 | Michelson | 606/70 |

| | | | |
|---|---|---|---|
| 2005/0192576 | A1* | 9/2005 | Michelson ............... 606/61 |
| 2005/0216010 | A1* | 9/2005 | Michelson ............... 606/69 |

FOREIGN PATENT DOCUMENTS

| | | |
|---|---|---|
| DE | 4409833 | 10/1995 |
| DE | 4414781 | 11/1995 |
| DE | 44 38 264 A | 3/1996 |
| DE | 19542064 | 6/1997 |
| WO | WO 94 26193 | 11/1994 |
| WO | WO 95 35067 | 12/1995 |
| WO | WO 96 08206 | 3/1996 |
| WO | WO 96 39975 | 12/1996 |
| WO | WO 99 56653 | 11/1999 |
| WO | WO 00/01314 | 1/2000 |
| WO | WO 01 26566 | 4/2001 |
| WO | WO 01/89428 | 11/2001 |

OTHER PUBLICATIONS

Aesculap Scientific Information Booklet; *Anterior Cervical Fusion and Interbody Stabilization with the Trapezial Osteosynthetic Plate Technique* by Wolfhard Casper; Feb. 1986.
Synthes Brochure: Spine for *Cervical Spine Locking Plate*; 1991.
Orion Brochure: *Anterior Cervical Plate System, Surgical Technique*, as described by Gary L. Lowery, M.D., Ph.D.; 1996.
Codman Brochure: *Anterior Cervical Plate System*; Sep. 1995.
Spinal Concepts Brochure: *The AcuFix, Anterior Cervical Plate System*; Undated.
EBI Brochure: *Introducing EBI VueLock, Anterior Cervical Plate System*; 2001.
Blackstone Brochure: *Blackstone Anterior Cervical Plate*; Undated.
Alphatec Manufacturing Brochure: *Deltaloc, Anterior Cervical Plate System*; Undated.
Sofamor Danek Brochure: *Atlantis, Anterior Cervical Plate System*; Undated.
Ortho Development Brochure: *Ortho Development Cervical Plate*; Undated.
Osteotech Brochure: *Affirm, Anterior Cervial Plate System*; Undated.
Office Action dated Jun. 30, 2004 from U.S. Appl. No. 10/160,062.
Office Action dated Feb. 13, 2006 from U.S. Appl. No. 10/160,062.
Office Action dated Oct. 31, 2005 from U.S. Appl. No. 10/810,190.
Office Action dated Aug. 8, 2007 from U.S. Appl. No. 10/925,857.
Office Action dated Jun. 18, 2009 from U.S. Appl. No. 10/925,857.
Office Action dated Nov. 24, 2009 from U.S. Appl. No. 10/925,857.
Office Action dated Jun. 9, 2004 from U.S. Appl. No. 10/160,086.
Office Action dated May 16, 2005 from U.S. Appl. No. 10/160,086.
Office Action dated Dec. 21, 2005 from U.S. Appl. No. 10/160,086.
Office Action dated Nov. 27, 2006 from U.S. Appl. No. 10/809,242.
Office Action dated Jun. 1, 2007 from U.S. Appl. No. 11/130,934.
Office Action dated May 15, 2008 from U.S. Appl. No. 11/130,934.
Office Action dated Jul. 13, 2004 from U.S. Appl. No. 10/160,247.
Office Action dated Mar. 23, 2005 from U.S. Appl. No. 10/160,247.
Office Action dated Oct. 31, 2005 from U.S. Appl. No. 10/810,230.
Office Action dated Aug. 1, 2007 from U.S. Appl. No. 10/926,734.
Office Action dated Jun. 19, 2009 from U.S. Appl. No. 10/926,734.
Office Action dated Dec. 3, 2009 from U.S. Appl. No. 10/926,734.
Office Action dated Mar. 11, 2004 from U.S. Appl. No. 10/160,407.
Office Action dated Apr. 8, 2005 from U.S. Appl. No. 10/160,407.
Office Action dated May 17, 2007 from U.S. Appl. No. 11/102,112.
Office Action dated Jan. 17, 2008 from U.S. Appl. No. 11/102,112.
Office Action dated Jul. 31, 2008 from U.S. Appl. No. 11/102,112.
Office Action dated Jan. 30, 2009 from U.S. Appl. No. 11/102,112.
Office Action dated Jun. 1, 2007 from U.S. Appl. No. 11/128,556.
Office Action dated Jan. 17, 2008 from U.S. Appl. No. 11/128,556.
Office Action dated Aug. 6, 2008 from U.S. Appl. No. 11/128,556.
Office Action dated. Feb. 3, 2009 from U.S. Appl. No. 11/128,556.
Office Action dated Jul. 1, 2009 from U.S. Appl. No. 11/128,556.
Office Action dated Sep. 8, 2004 from U.S. Appl. No. 10/160,059.
Office Action dated Apr. 1, 2005 from U.S. Appl. No. 10/160,059.

* cited by examiner

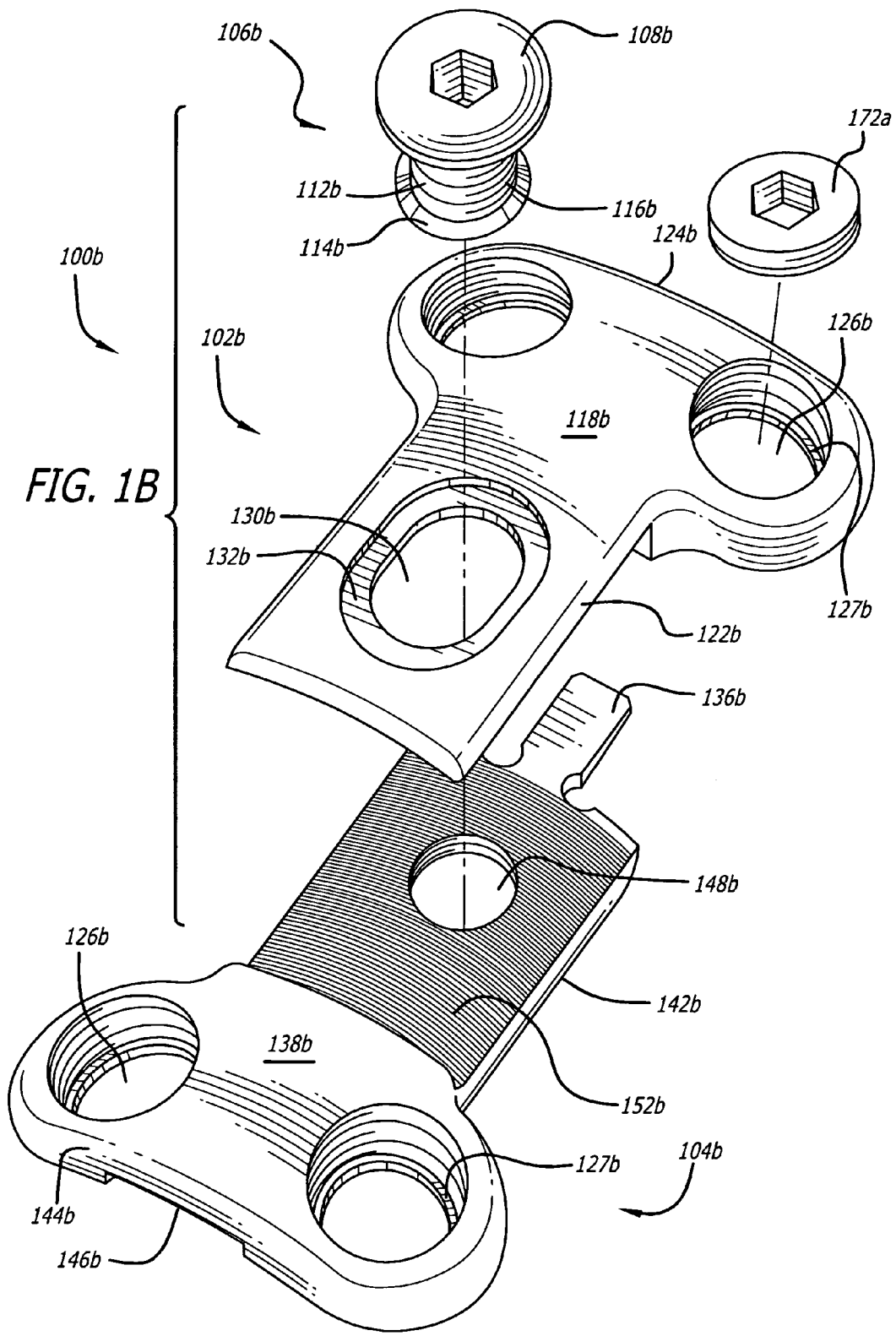

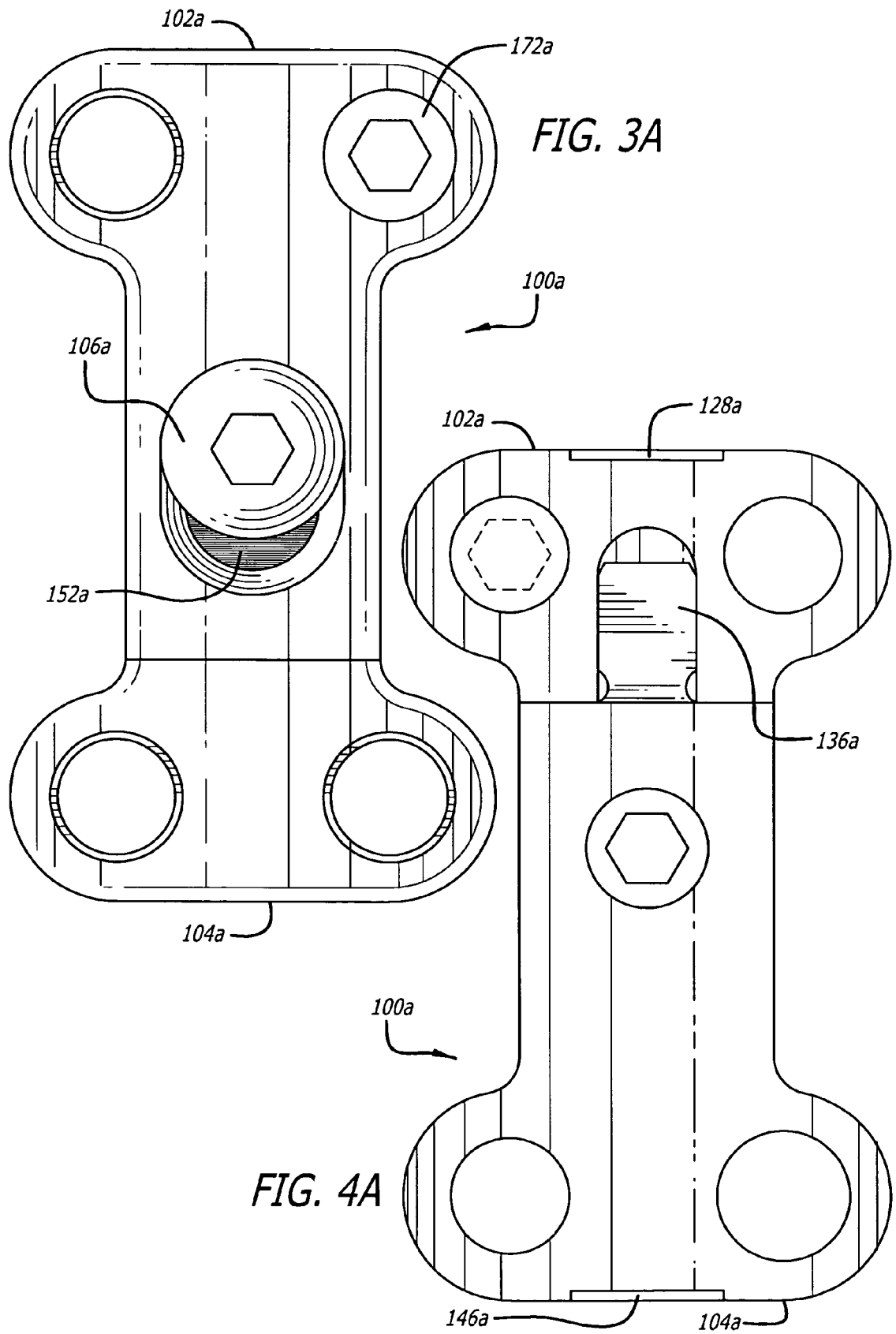

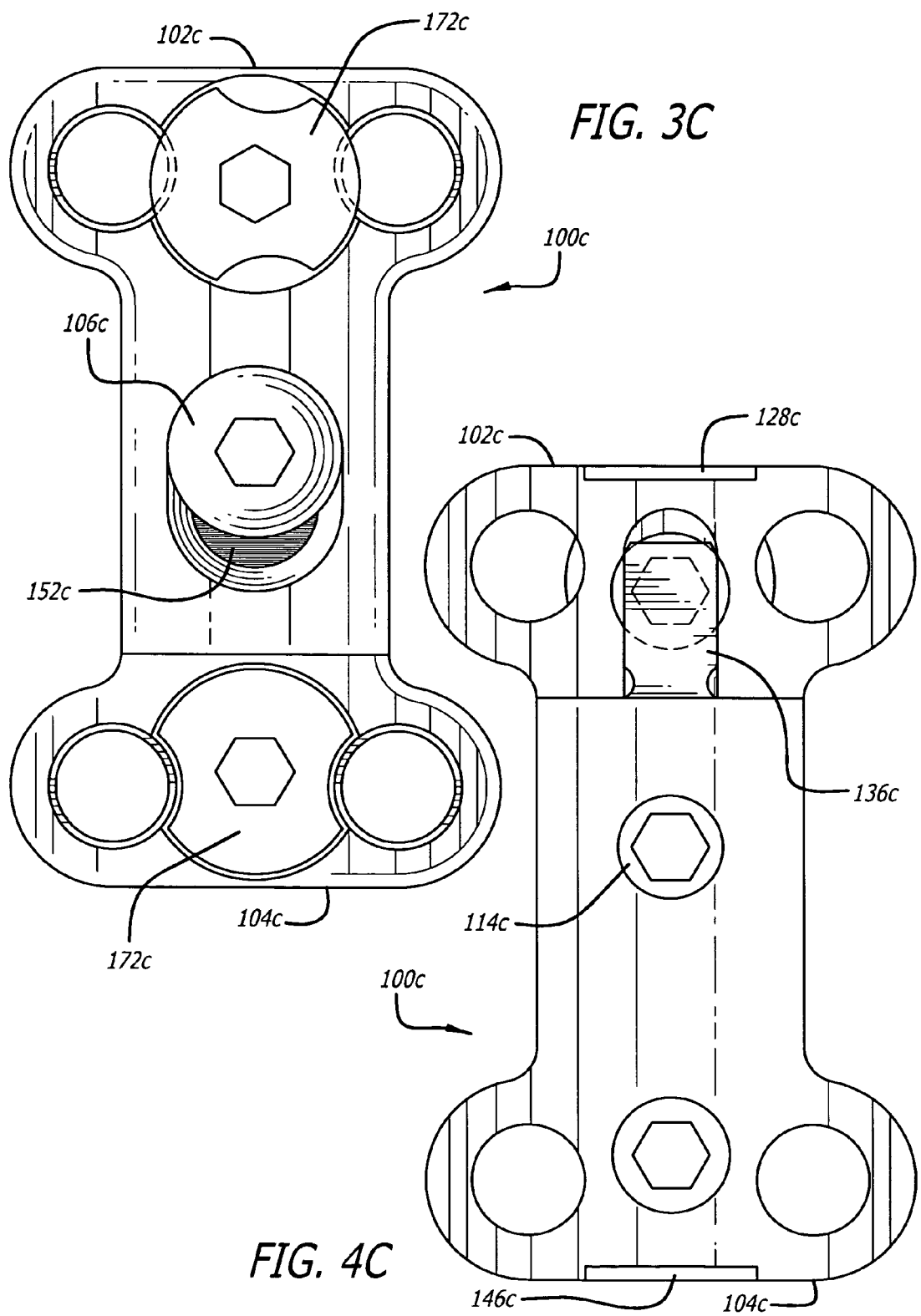

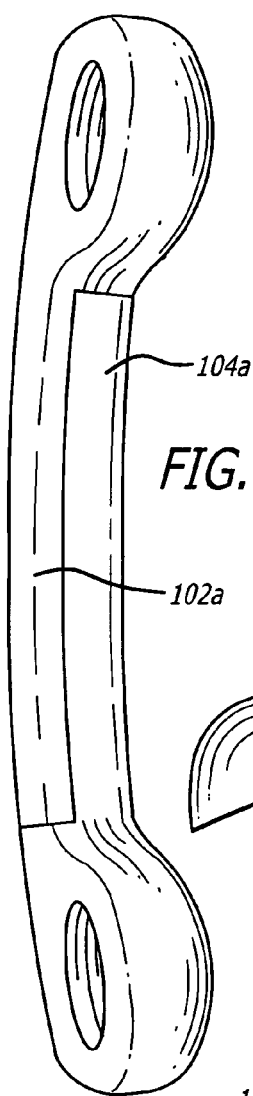
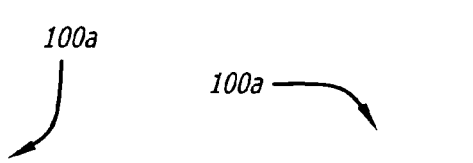
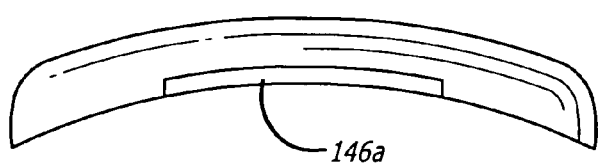
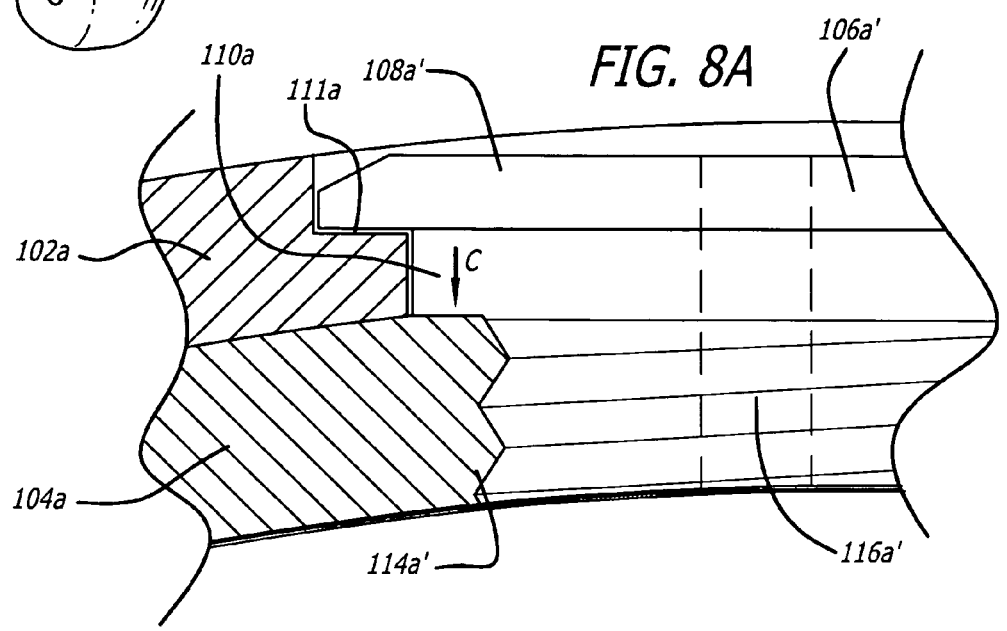

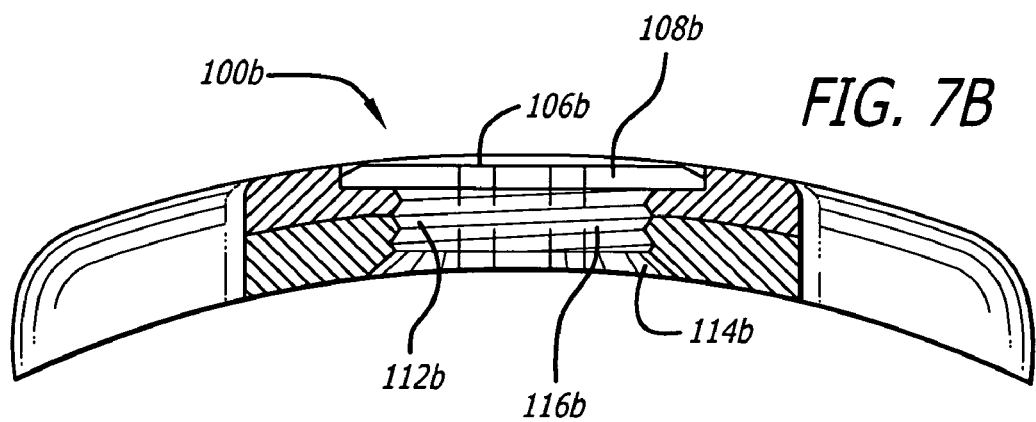
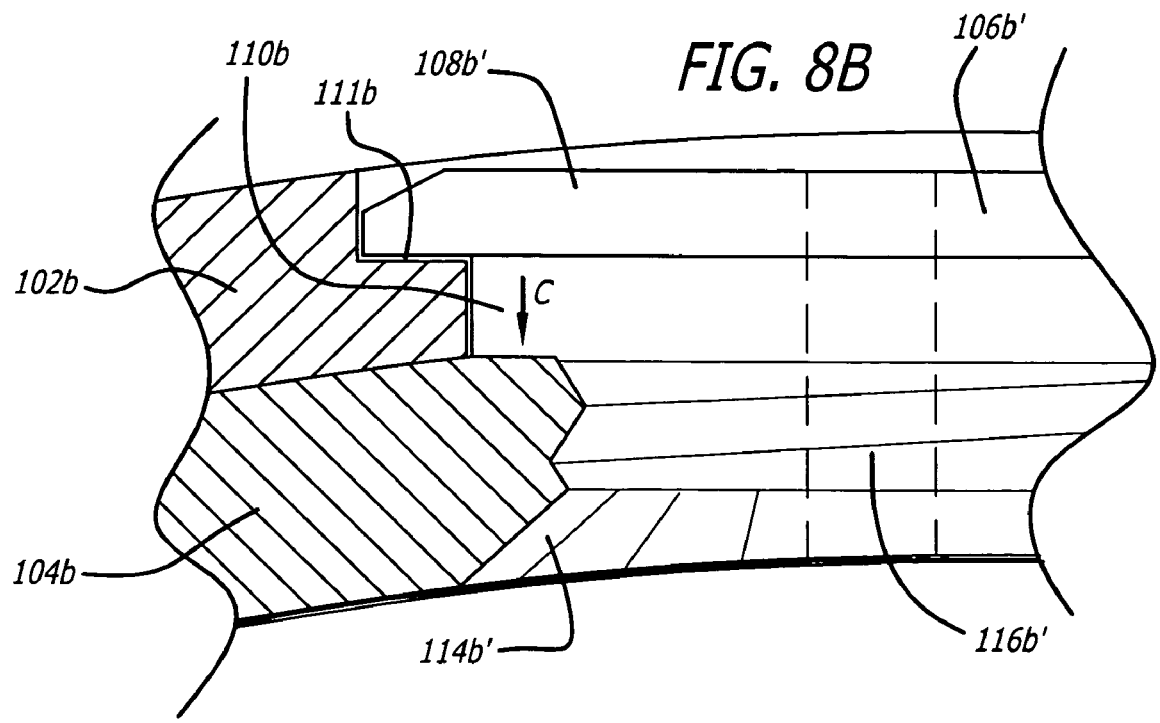

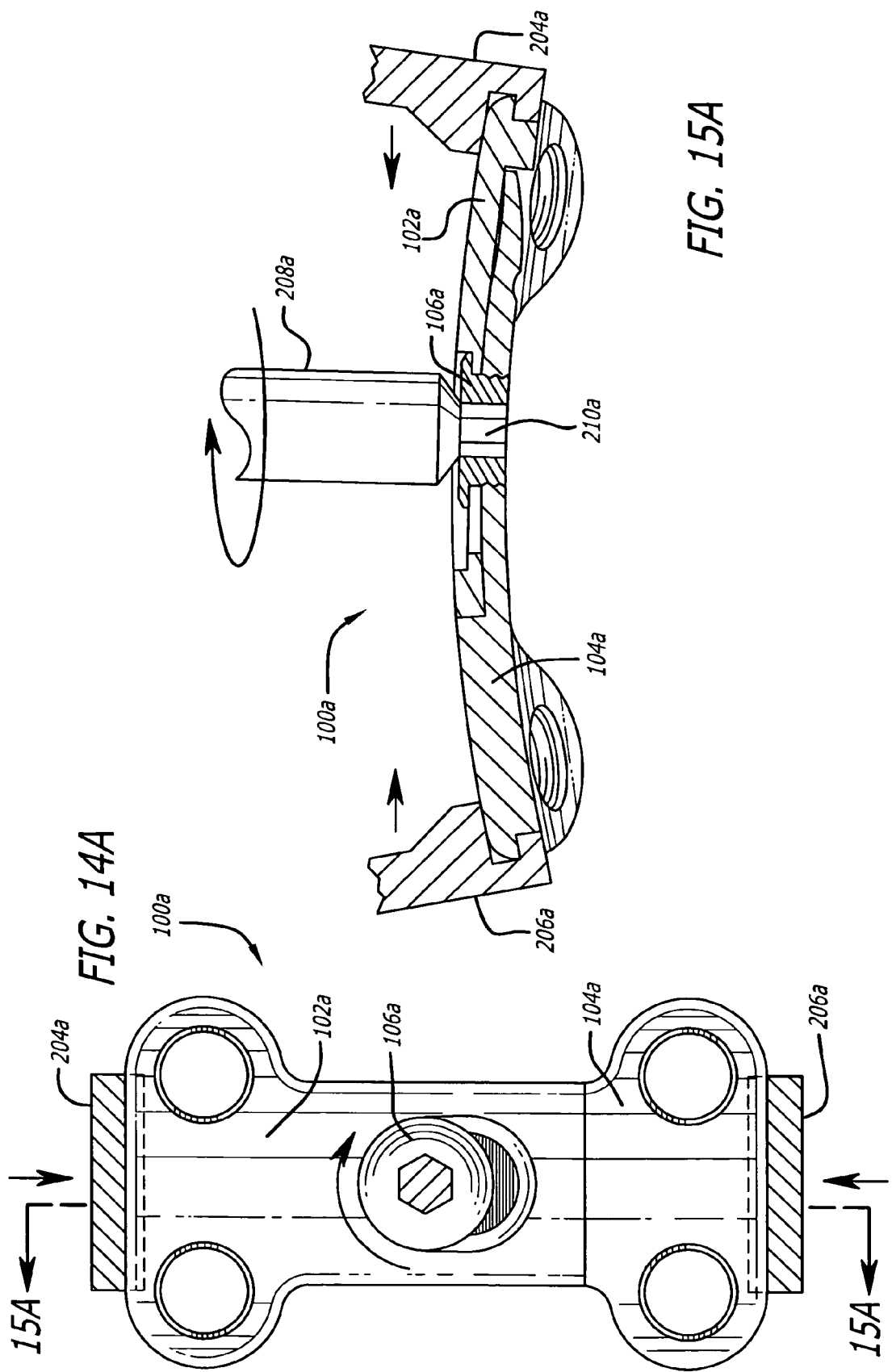

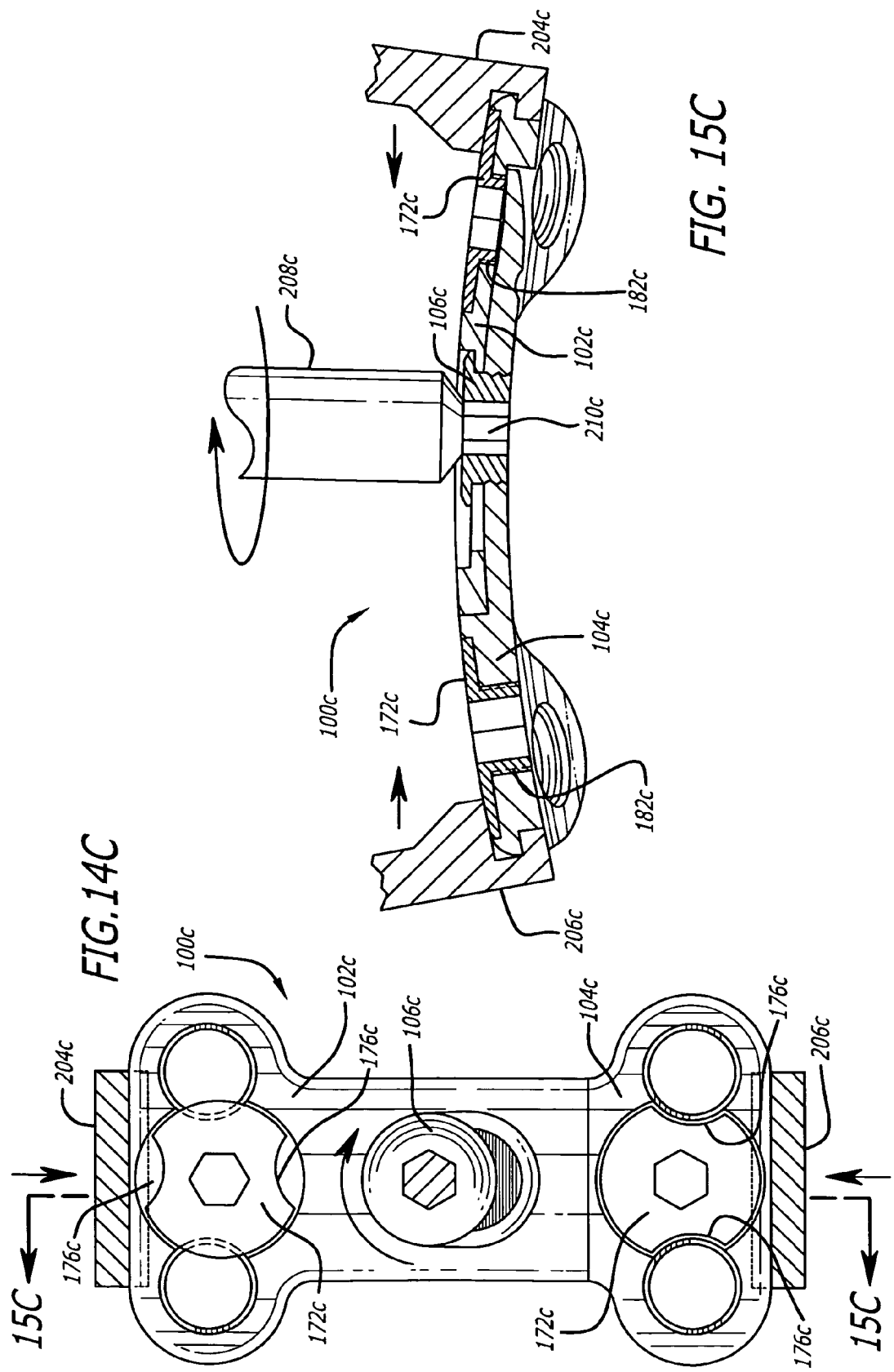

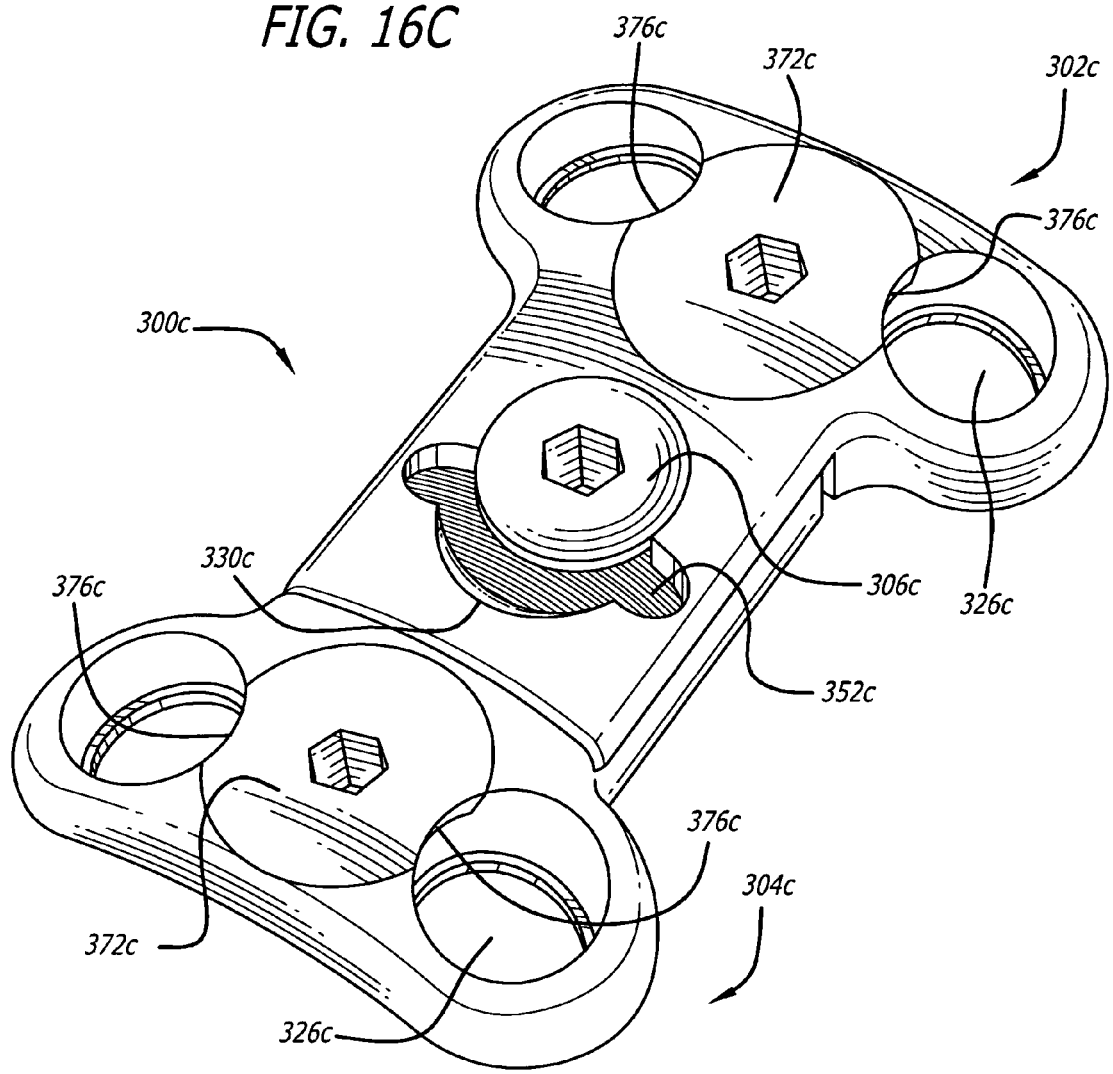

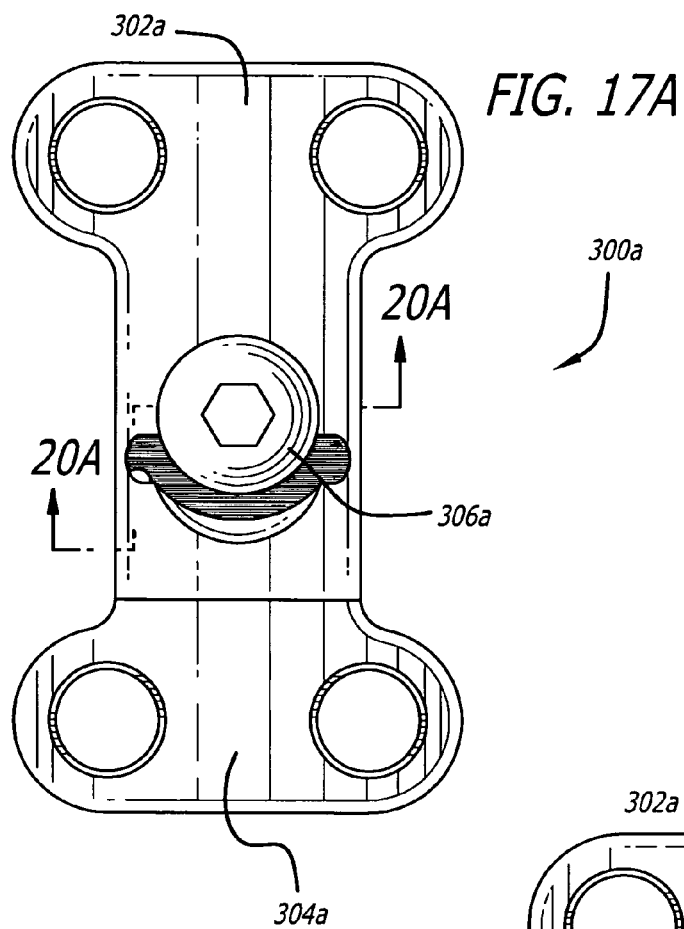
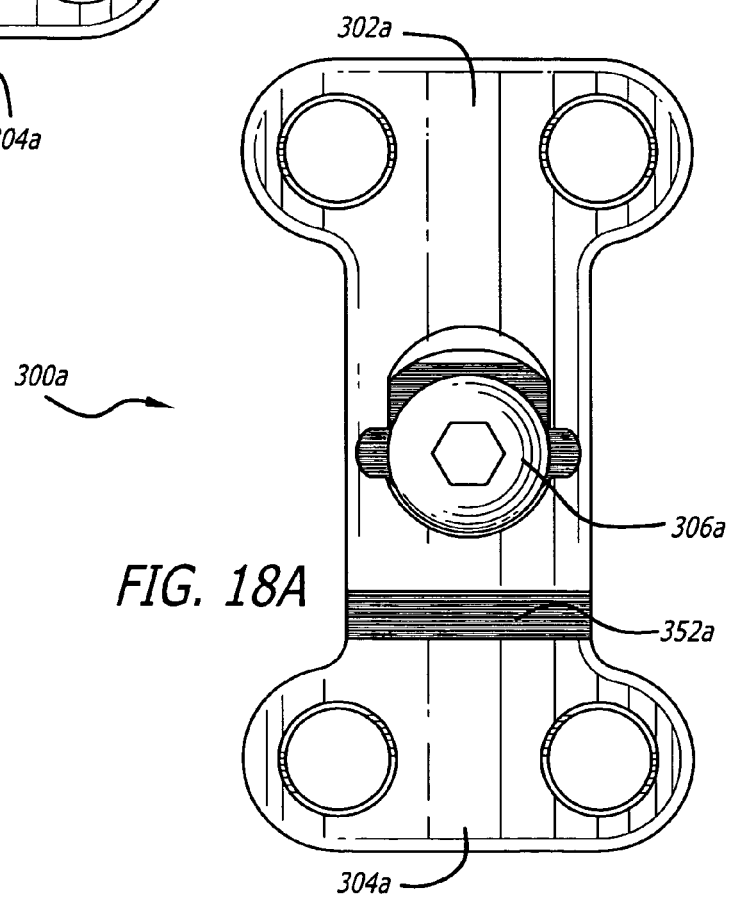

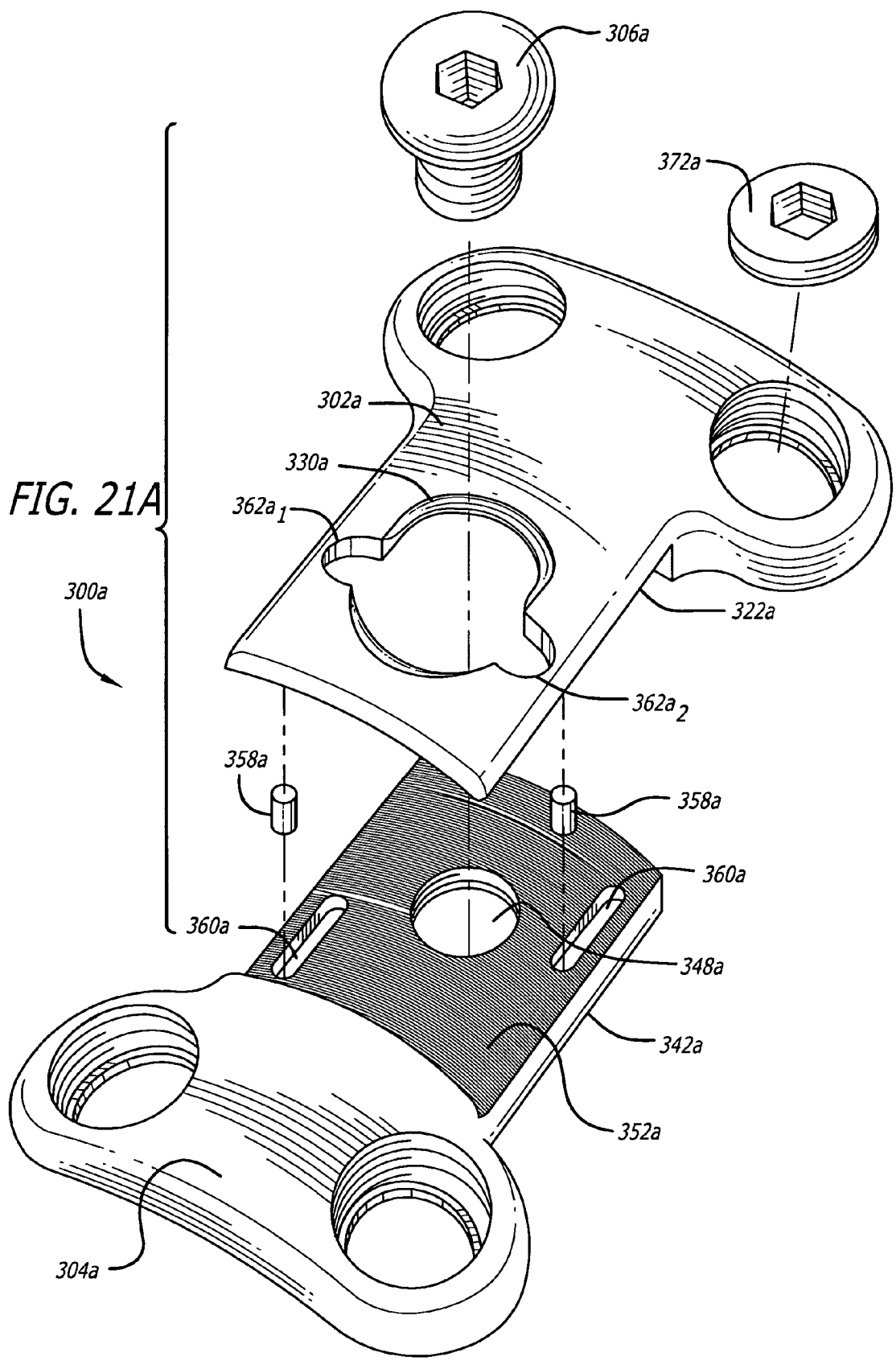

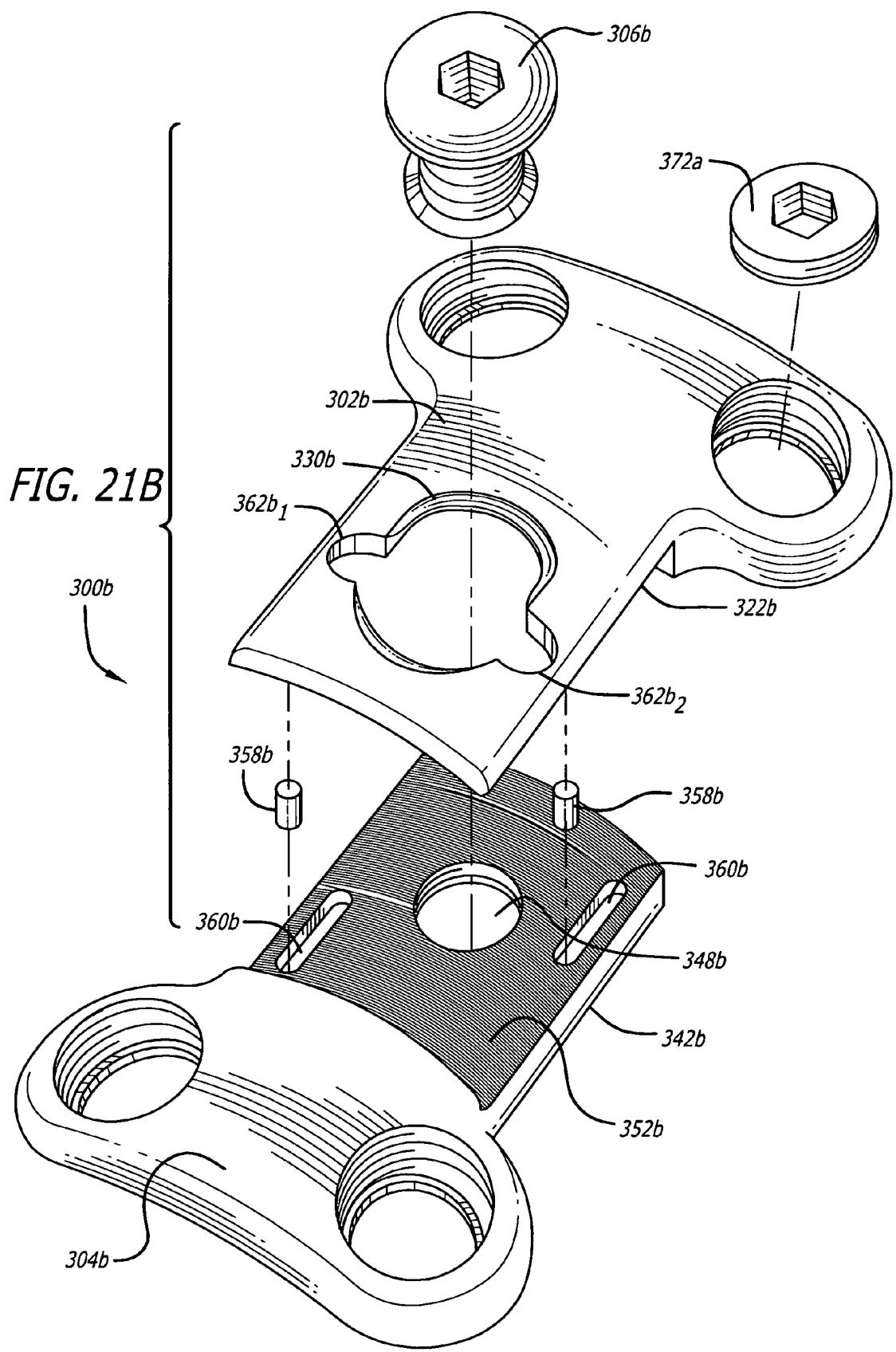

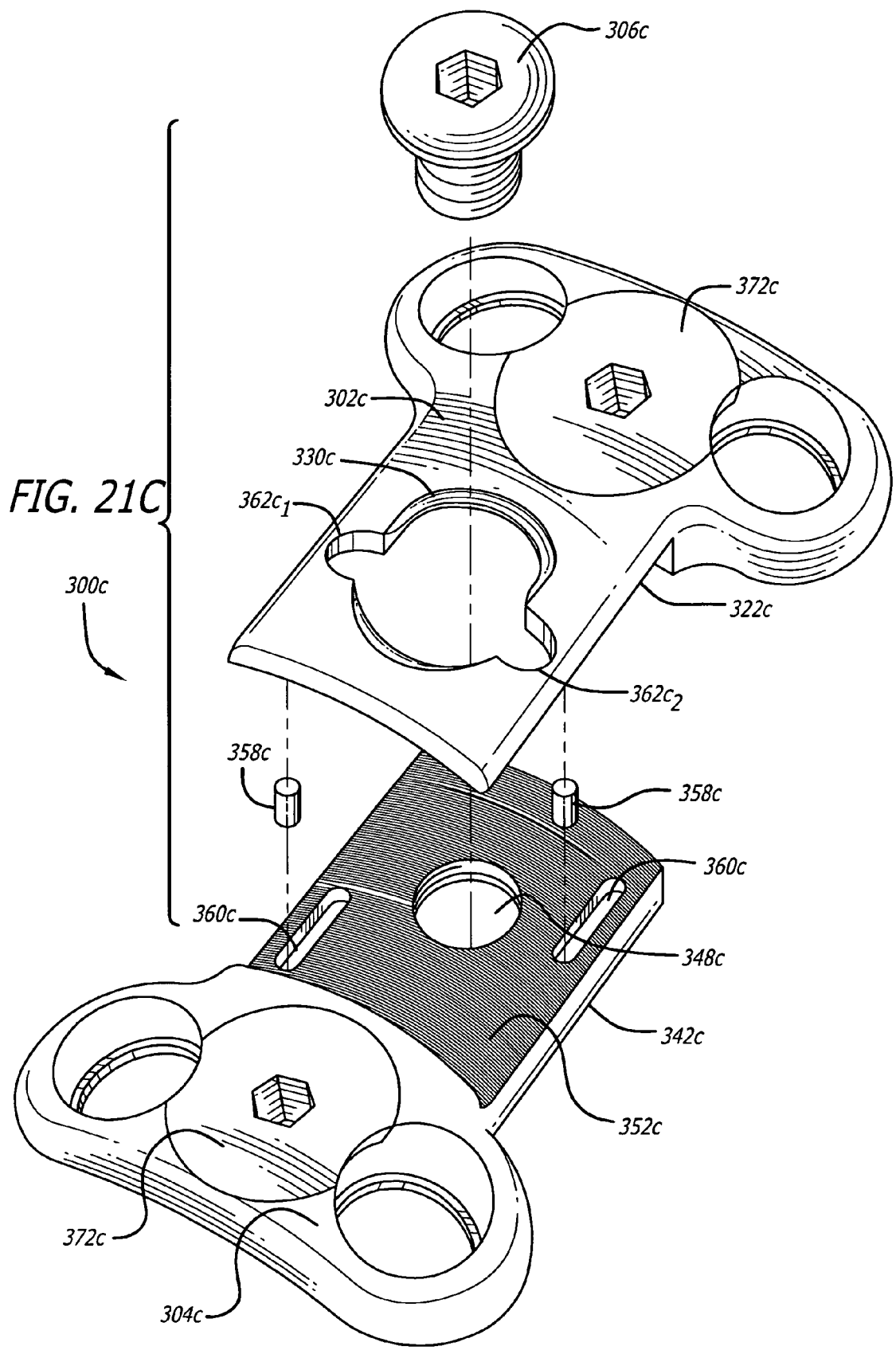

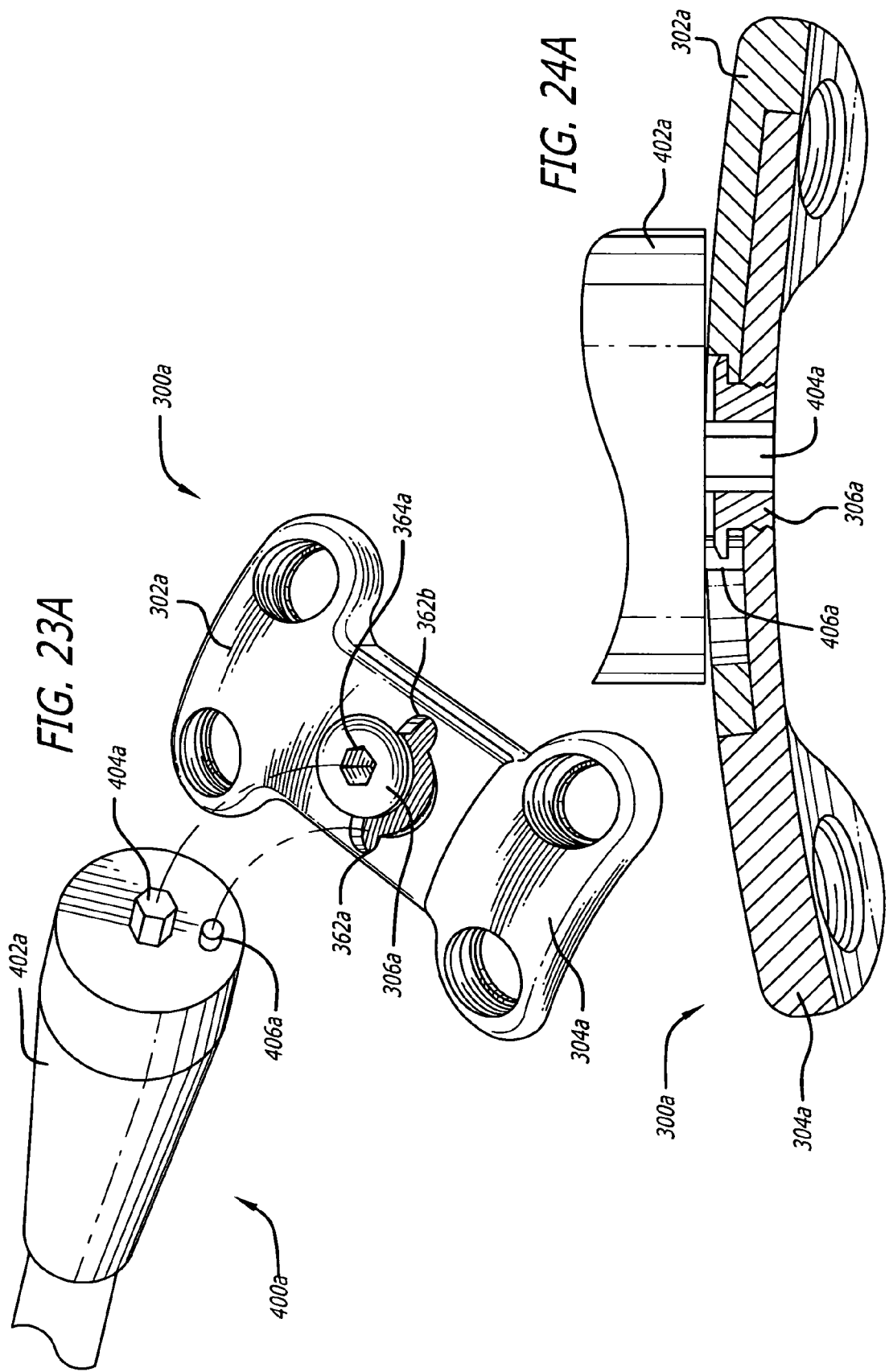

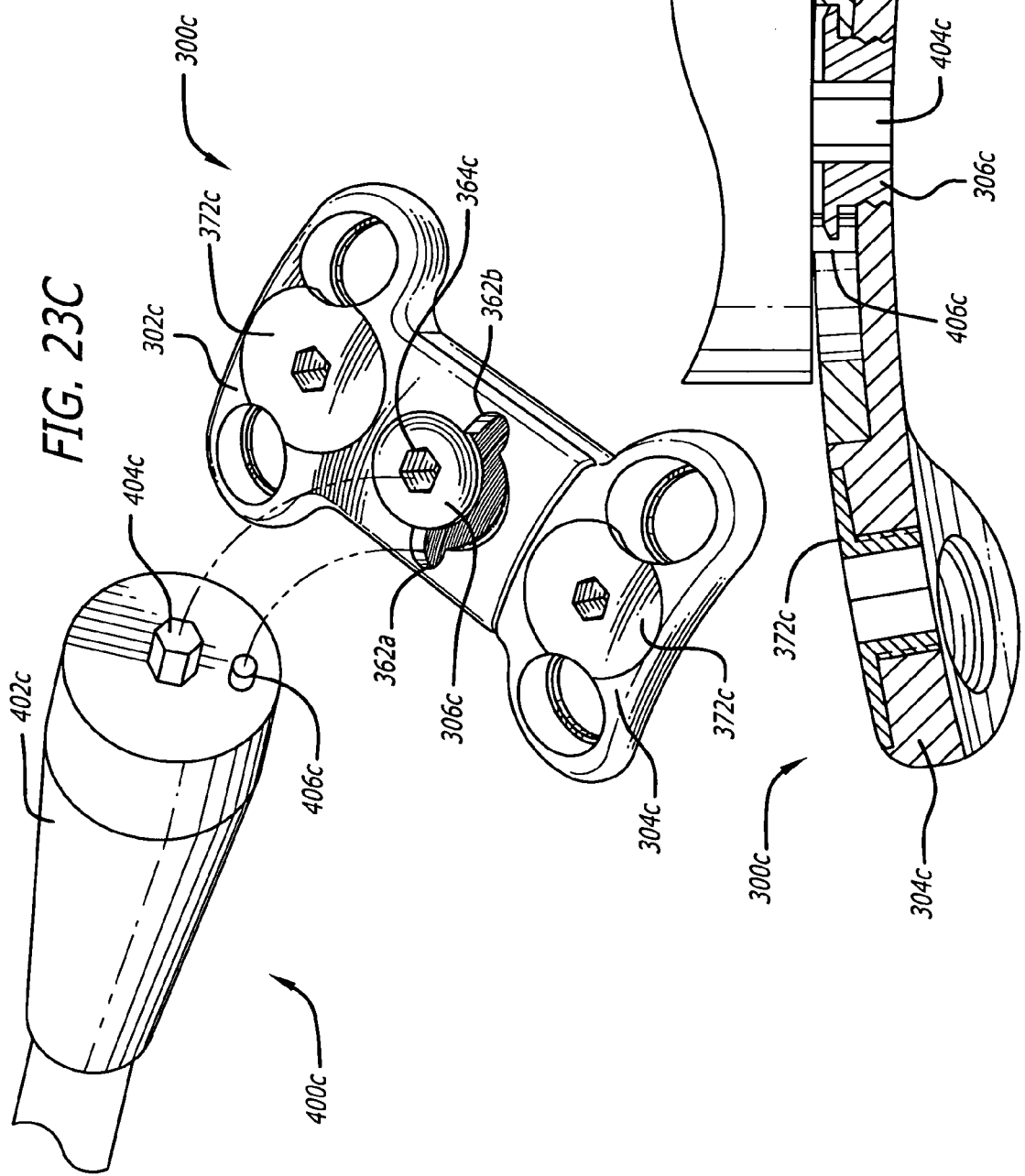

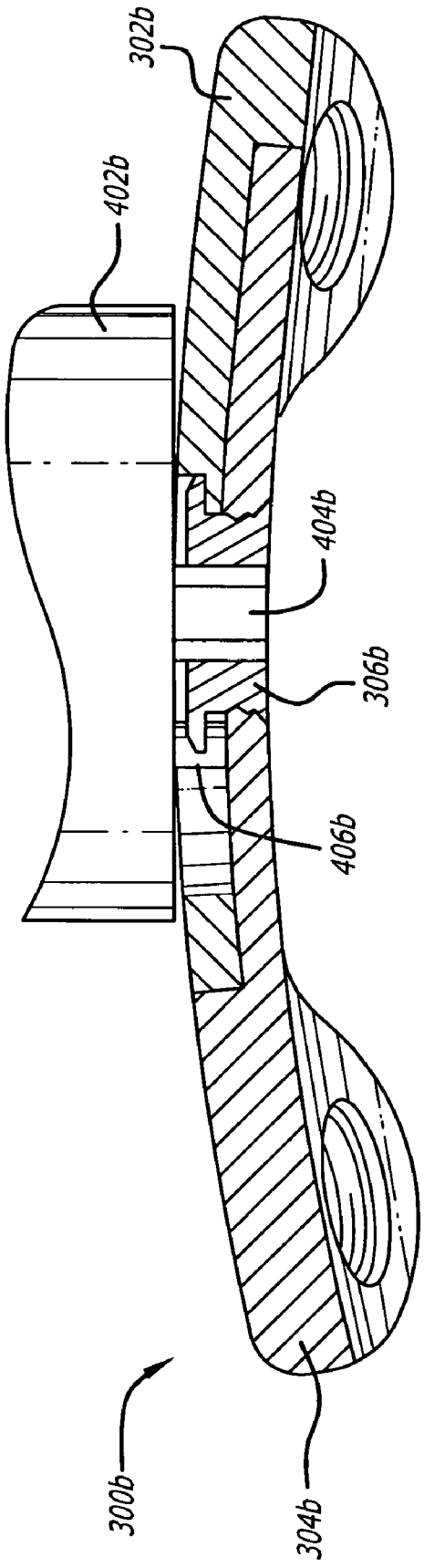

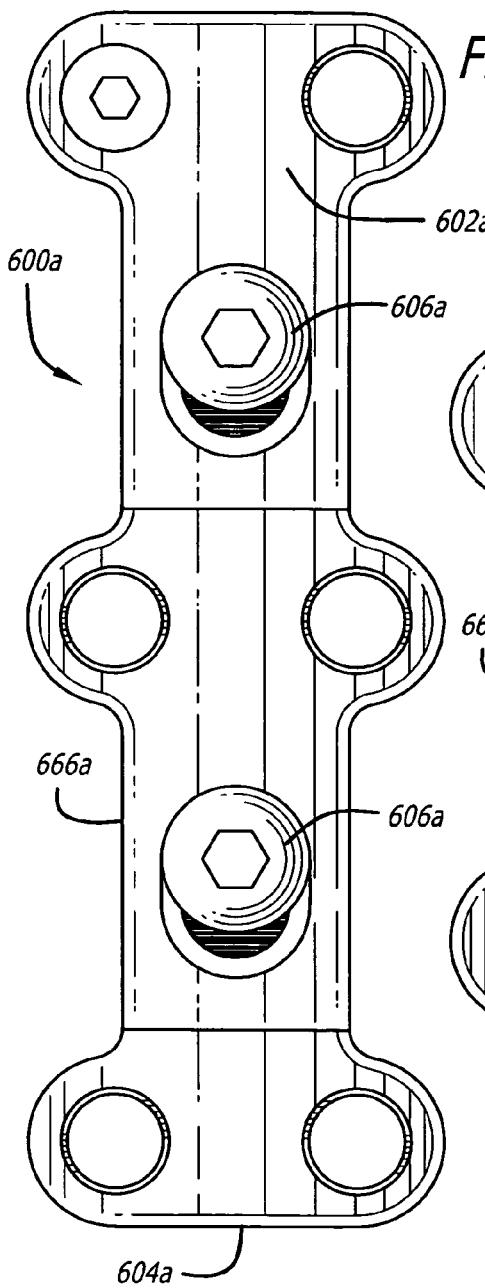
FIG. 32A
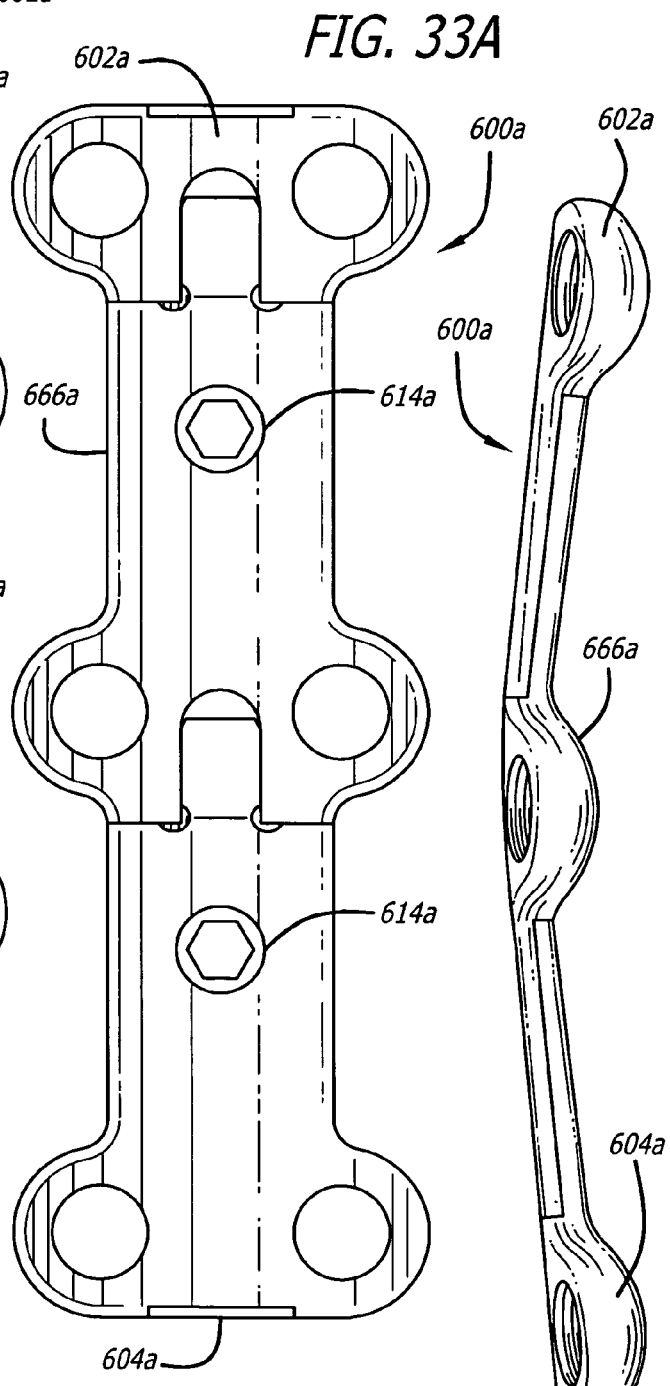
FIG. 33A
FIG. 34A

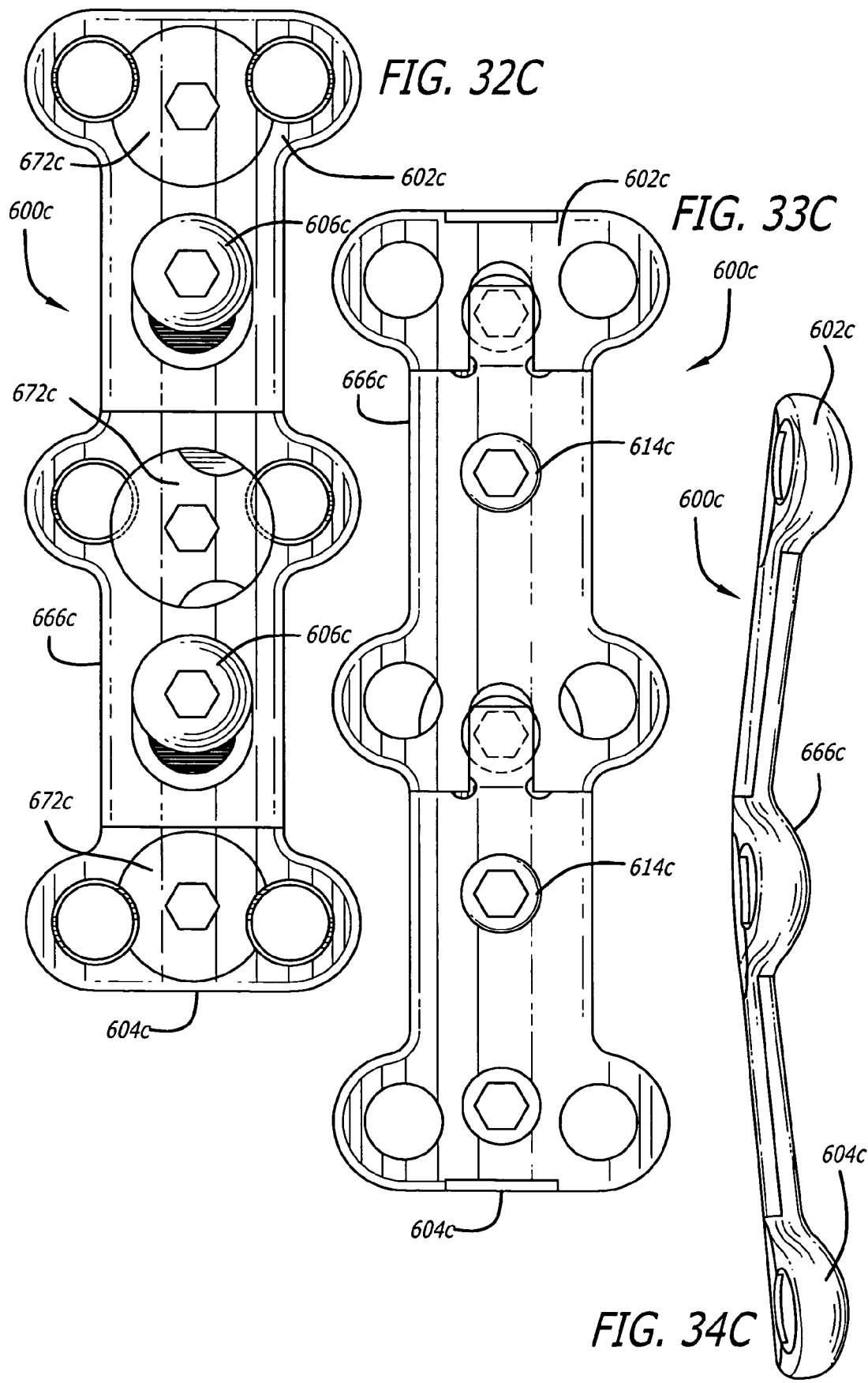

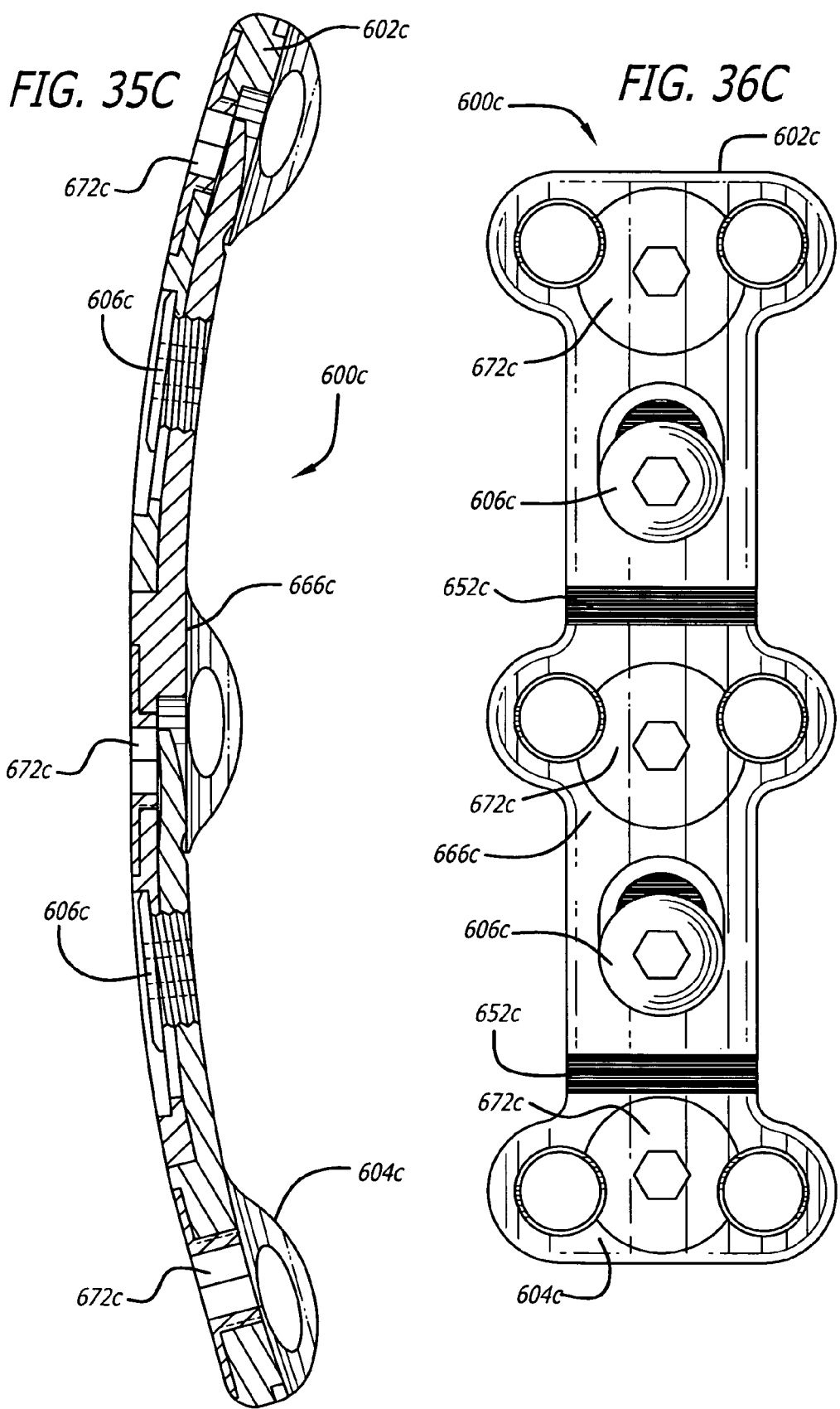

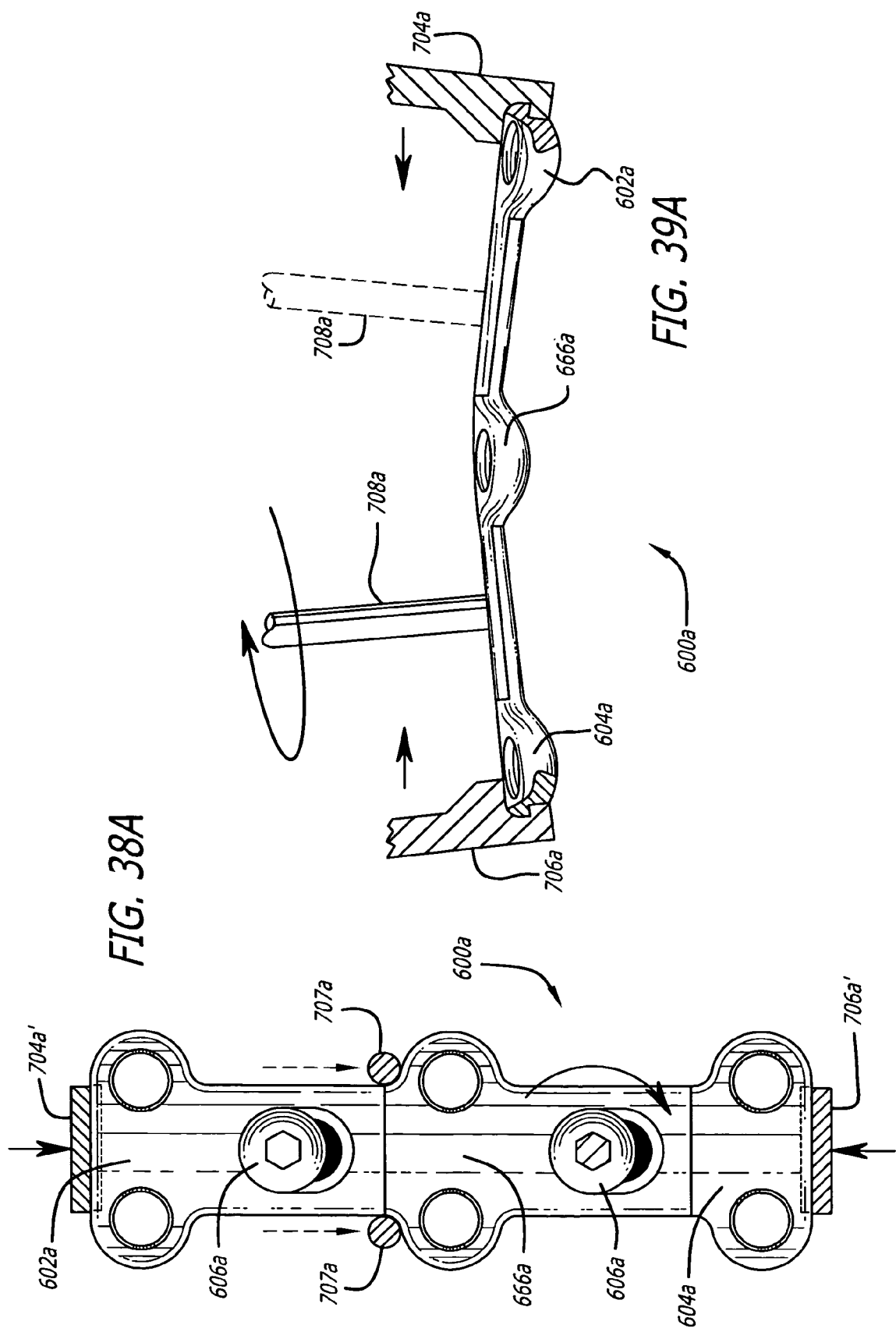

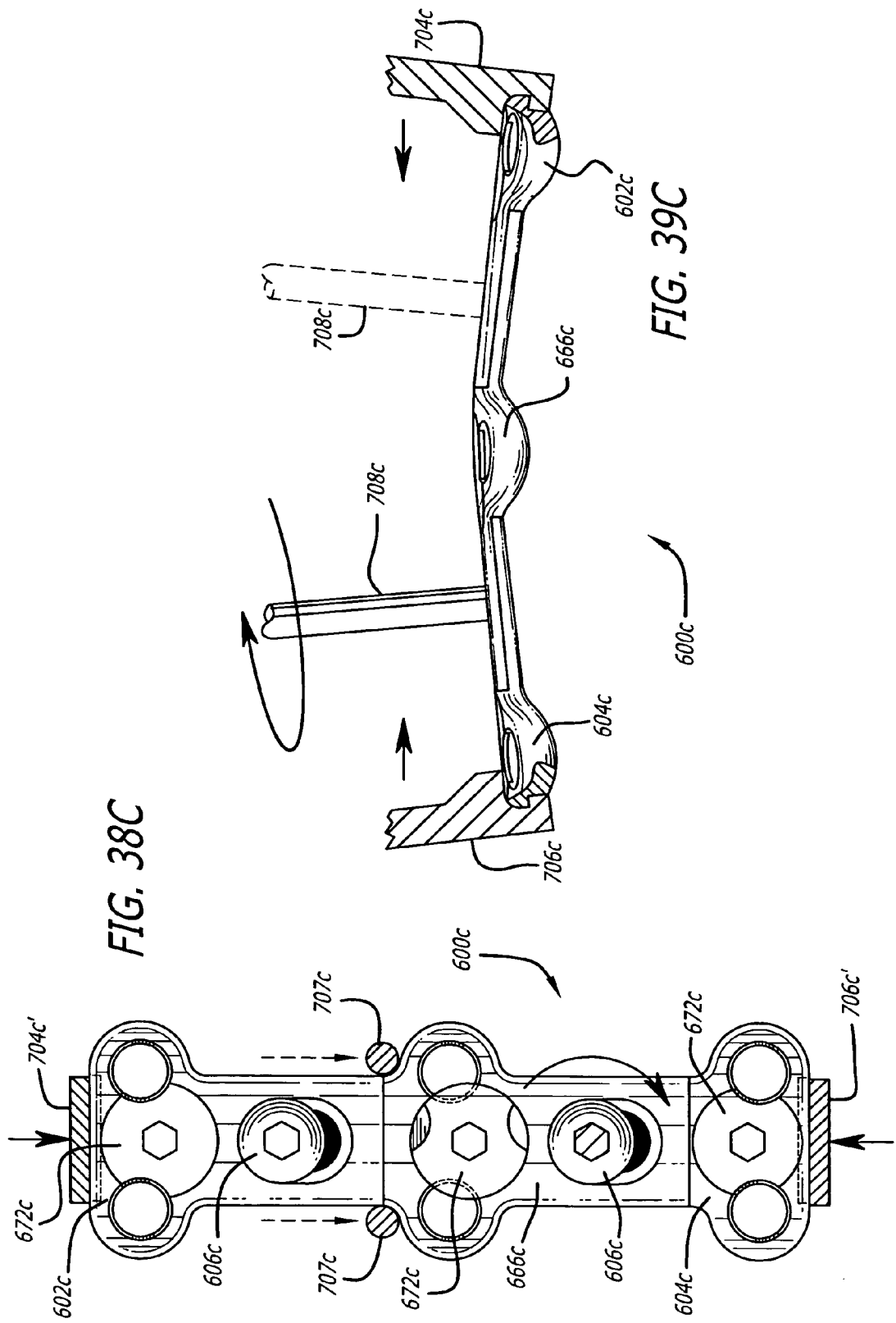

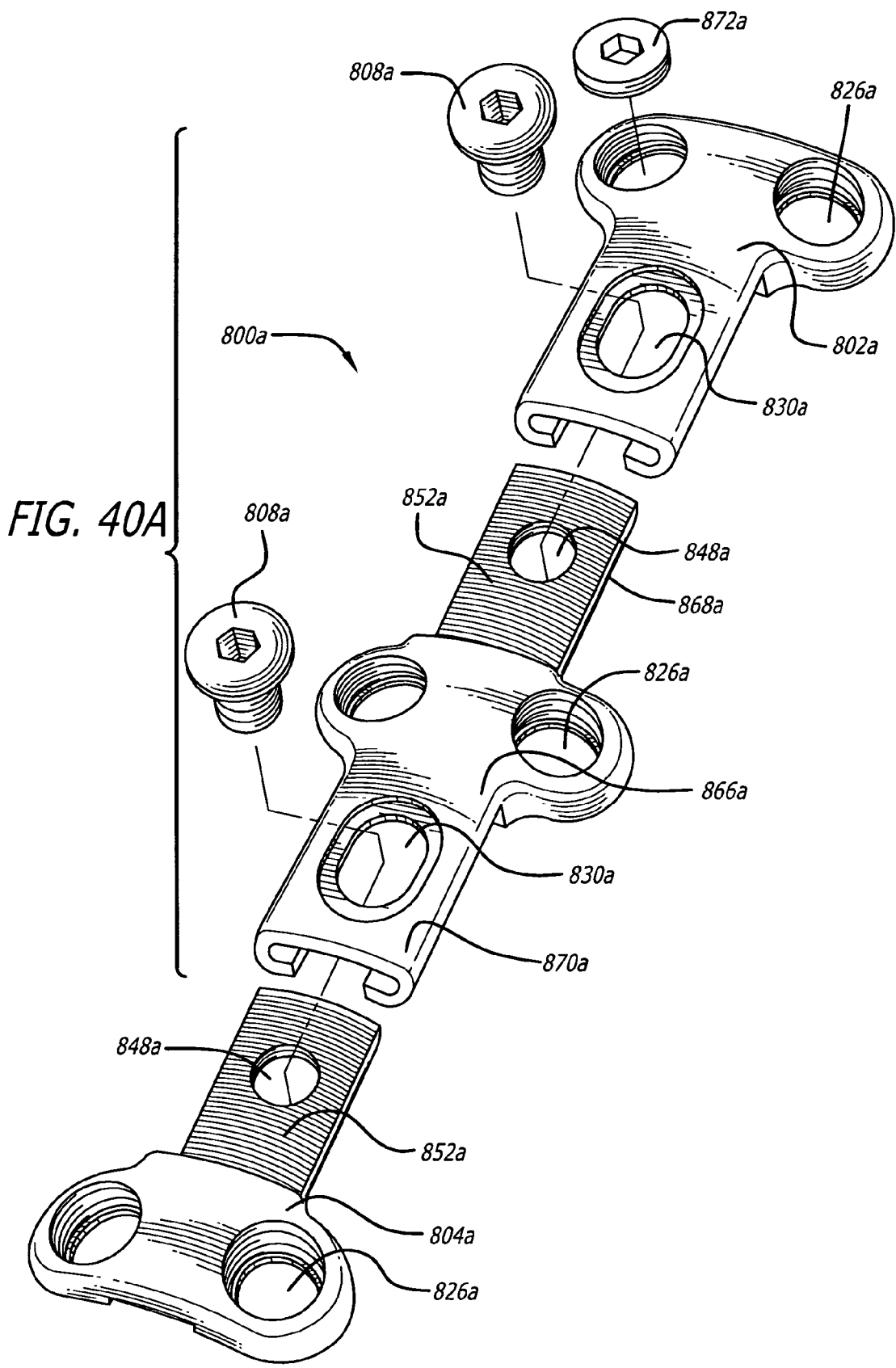

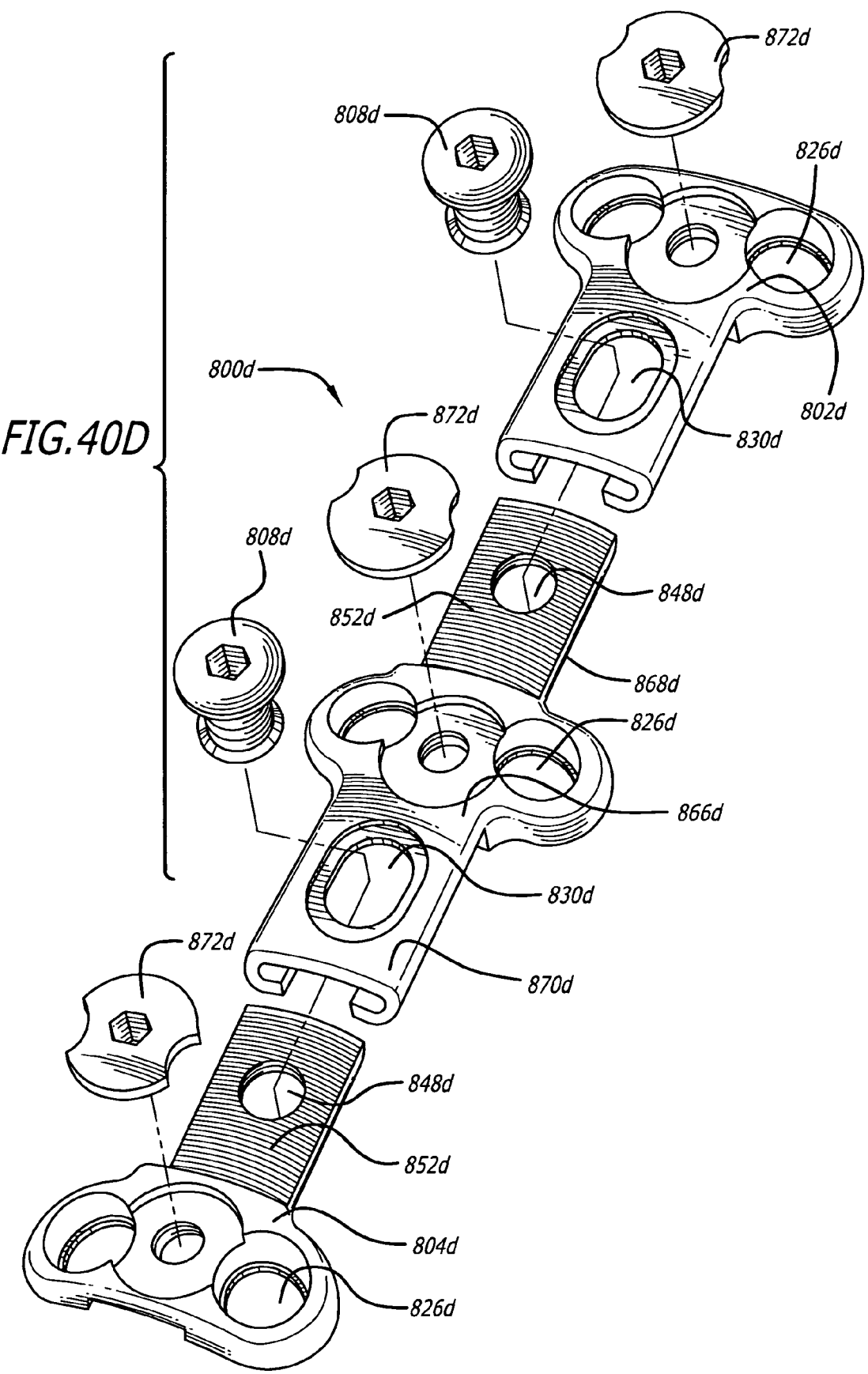

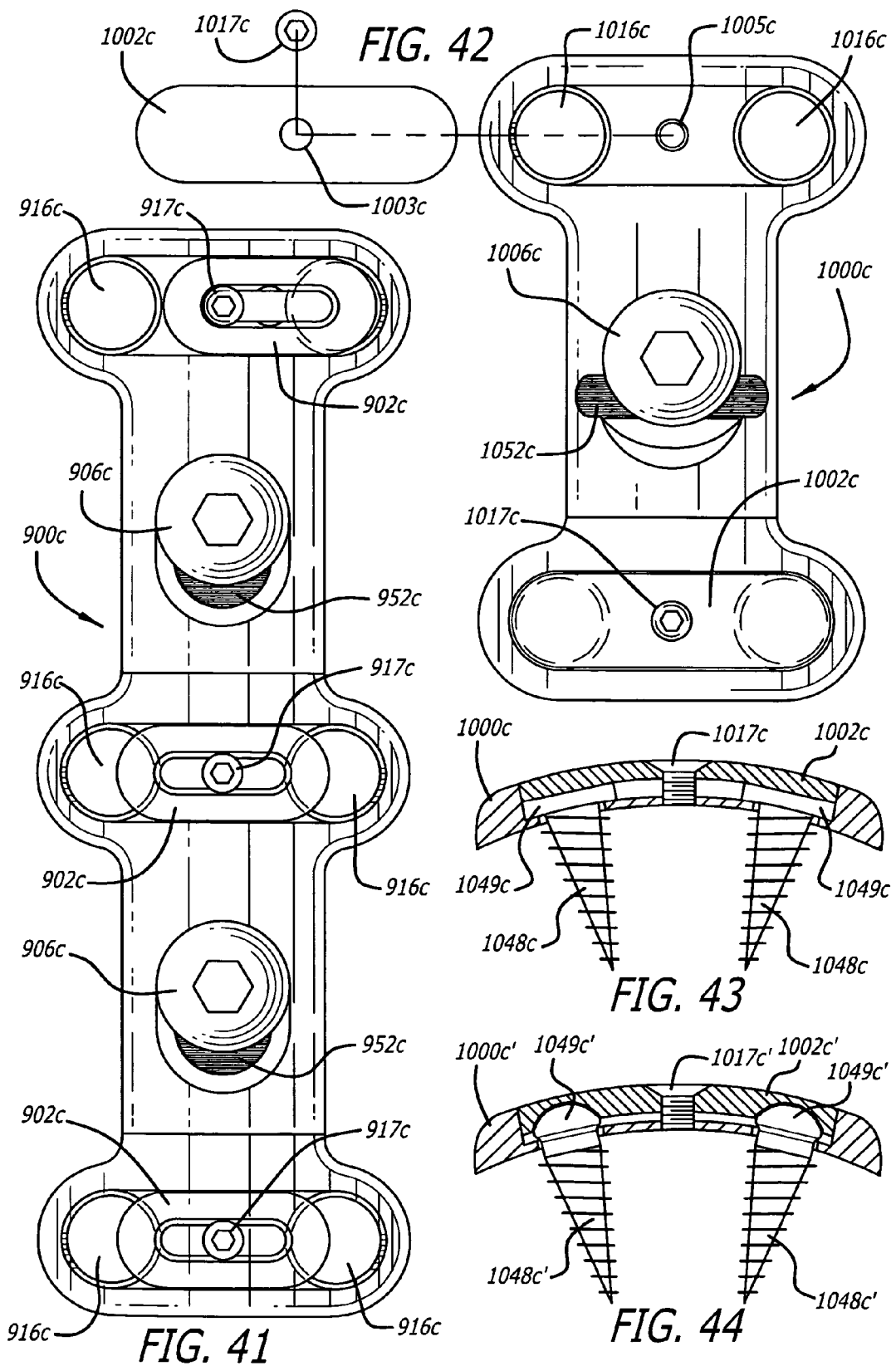

METHOD FOR INSTALLATION OF DYNAMIC ANTERIOR CERVICAL PLATE SYSTEM HAVING MOVEABLE SEGMENTS

RELATED APPLICATIONS

This application is a divisional of U.S. application Ser. No. 10/160,059, filed Jun. 4, 2002 now U.S. Pat. No. 7,118,573; which claims the benefit of U.S. Provisional Application No. 60/379,589, filed May 9, 2002; U.S. Provisional Application No. 60/377,916, filed May 3, 2002; U.S. Provisional Application No. 60/356,318, filed Feb. 12, 2002; U.S. Provisional Application No. 60/355,194, filed Feb. 8, 2002; U.S. Provisional Application No. 60/296,681, filed Jun. 6, 2001; U.S. Provisional Application No. 60/296,680, filed Jun. 6, 2001; U.S. Provisional Application No. 60/296,060, filed Jun. 4, 2001; and U.S. Provisional Application No. 60/296,059, filed Jun. 4, 2001; all of which are incorporated by reference herein.

BACKGROUND

The use of plates, screws, and locks to prevent separation and backing out of screws from the plate, for use on the anterior aspect of the cervical spine to provide alignment and stability as an adjunct to fusion of adjacent vertebral bodies is known in the art. Also known in the art is that compressive load, within a physiological range across a fusion site, is beneficial to the fusion process. Conversely, a failure to maintain a compressive load across a fusion site, or to have a gap in the fusion construct continuity may lead to a failure to achieve fusion called pseudoarthrosis. A primary purpose of the aforementioned cervical hardware is to provide stability during the healing and fusion process. The fusion process occurs in part through a process called "creeping substitution" by which new living bone replaces the dead bone such as that of a bone graft. The fusion process involves a phase of bone resorption as preliminary to the formation of the new bone. It is possible then for the bone resorption to result in gaps in the continuity of the fusion mass, such that if the hardware is sufficiently rigid, such as occurs as a result of increasing the strength of the components and constraining the relationship of the screws to the plate, those gaps may persist and increase in size as the hardware holds the bone portions separated rather than allowing those bone portions to move together to close those gaps. This holding apart of the bone portions (called distraction) can therefore lead to a failure of fusion (pseudoarthrosis). These rigid systems by a combination of not inducing compression at the fusion site and of holding the bone portions to be fused apart may cause a "distraction pseudoarthrosis."

Alternative cervical plating systems have attempted to prevent distraction pseudoarthrosis by allowing the vertebral bodies to collapse towards each other as needed during the fusion process. Generally this has been done by allowing the bone screws to be free to move relative to the plate, that is, movement such as sliding, swiveling, rotating, and angulating, independent of whether the screws are prevented from separating or backing out of the plates such as by the use of locks. Undesired multidirectional instability can occur in such plating systems that is counter to the very purpose of such hardware which is to increase or provide for stability.

Another approach to solving this problem has been to attach by screws a block to each of the vertebral bodies to be fused and then to allow those blocks to slide up and down on a pair of rods. Each of these constructs have in common that they sacrifice stability, the ability to hold the bones to be fused rigidly in place and prevent undesired motion; for the ability to allow, but not cause the vertebral bodies to collapse.

There exists therefore a need for an improved anterior cervical plating system that is: (1) sufficiently rigid to maintain the desired alignment of the vertebral bodies to be fused; (2) capable of inducing compressive load across the fusion site; and/or (3) capable of allowing for the motion of the vertebral bodies towards each other to prevent or to close any gaps in the continuity of the fusion construct, while still being capable of preventing motion in all other directions. When similar challenges have been faced at other skeletal locations, the solution involved anchoring the bone screws through the far cortex of the bone portions to be joined, in effect anchoring the screws in such a way as to make it possible for the screws to force movement of the plates. In the cervical spine anteriorly, however, it has been found to be highly undesirable to drive the bone screws through the far cortex of the vertebral bodies, as this is where the spinal cord is located. There remains therefore a need for an improved cervical plating system as just described that does not require that the bone screws penetrate the far cortex to achieve the desired purpose as described.

The size of the vertebral bodies and the spacing between the vertebral bodies varies from patient to patient. The height of the vertebral bodies and the discs therebetween may vary level by level even in the same person. Thus, a plate of correct length does not necessarily have bone screw receiving holes correctly positioned to overlie the vertebral bodies in accordance with the spacing of the vertebral bodies to which the plate is to be applied. As a result, conventional plating systems of the past had to be manufactured in many different lengths and spacing configurations which were nevertheless fixed in an attempt to provide plates for many, though still possibly not all, of the various sizes and spacings of the vertebral bodies to which the plate was to be applied. For example, in a multi-segment plate the length of the plate would need to correspond to the overall length of the vertebral bodies to be joined and actual distances therebetween and the screw holes of the plate arranged to overlie the vertebral bodies. In order to cover the possible range of sizes, health care facilities would need to carry a large inventory of different sizes of plates, in some cases as many as sixty different sized plates would be needed. Such a large inventory is an expensive undertaking and still worse, facilities with a high caseload need to invest in more than one of each plate size to provide for the possibility of overlapping demand for the same plate size. Facilities with lower caseloads may find it prohibitively expensive to stock an inventory of plates sufficient to cover the range of possible sizes and thus might not be able to afford to stock a set at all or have less than all sizes of plates needed for all cases. Manufactures cannot afford to place a set of plates on consignment in facilities with low caseloads as the number of sales would not cover the carrying costs of the plates.

There exists therefore a need for an improved anterior cervical plating system that (1) allows for the overall adjustability of the length of the plate; (2) allows for variations in spacing between the bone screw receiving holes of the plate portions corresponding to the attachment point of the plate to the vertebral bodies; (3) reduces the requisite plate inventory; and (4) can avoid or prevent distraction pseudoarthrosis without itself introducing multidirectional instability.

SUMMARY OF THE INVENTION

The present invention in one preferred embodiment is a dynamic anterior cervical plating system including a plate comprising segments in moveable relationship to each other adapted to allow for the overall adjustability of the length of the plate and for variations in the intersegmental spacing of the bone screw receiving holes, to create and/or store a compressive load across a disc space between two adjacent vertebral bodies to be fused, and/or to allow motion of the vertebral bodies toward each other to prevent or close gaps in the continuity of a fusion construct, while preferably preventing motion in all other directions when in use. As used herein, a spinal fusion segment is defined as two vertebral bodies with an intervertebral implant, made of bone or an artificial material, in the disc space therebetween. As used herein, a fusion construct is defined as a spinal fusion segment plus the hardware, such as a plate and screws for example.

The present invention in another preferred embodiment is a dynamic, modular, anterior cervical plating system including a plate comprising assembleable segments in moveable relationship to each other adapted to allow for the overall adjustability of the length of the plate and for variations in the intersegmental spacing of the bone screw receiving holes, to create and/or store a compressive load across a disc space between two adjacent vertebral bodies to be fused, and/or to allow motion of the vertebral bodies toward each other to prevent or close gaps in the continuity of a fusion construct, while preferably preventing motion in all other directions when in use.

The ability to permit the movement of adjacent vertebral bodies toward one another is referred to herein as "dynamization." Dynamization may be "passive" allowing the plate to shorten when a shortening force, such as a compressive load is applied. Dynamization may be "active" wherein the plating system stores energy to induce shortening of the fusion construct should the opportunity present. The present invention plating system may passively dynamize, actively dynamize, provide a combination of both, as well as convert and store certain compressive stresses encountered during the healing phase as will be more fully described herein.

The plate segments also can be moved to vary the spacing between the plate segments as well as the overall length of the plate so that the size of the plate may be adjusted to correspond to a range of sizes and spacing of the adjacent vertebral bodies to which the plate is being applied; thereby greatly reducing the inventory of plate sizes needed. The moveable plate segments combine to form the plate. Each plate segment is attached to a vertebral body to be fused by at least one bone screw and preferably a pair of bone screws, which when inserted, are preferably prevented from backing out of the plate by at least one locking element adapted to lock at least two bone screws to the plate. In an alternative embodiment, a locking element is adapted to lock a single bone screw to the plate.

The paths of the bone screws through the plate may be fixed or variable. If the paths are variable, they may be more or less stable depending on how resistant to motion the screws are relative to the plate when the screws are locked to the plate. To the extent that screws are sufficiently stable in relation to the plate to make use of the present inventive teaching, these screw, plate, and lock combinations or variations thereon are also within the broad scope of the present invention.

In a preferred embodiment of the present invention, after each of the segments of the plate are attached to a respective one of the vertebral bodies to be fused, the plate is capable of movement from a first or elongated position to a second or shorter position, a process generally referred to as "passive dynamization"—that is the ability of the system to allow the plated spinal segment to shorten in response to unmet compressive loads to allow for the bone portions to be fused to move close together to restore contact. A preferred embodiment of this present invention is capable of allowing for this passive dynamization while preventing undesirable motions along and around all axes other than the motion along the longitudinal axis of the plate.

In another preferred embodiment of the present invention, the plate segments are articulated in such a way that even the one freedom of movement that is along the longitudinal axis of the plate is selectively limited to the desired passive dynamization—that is shortening of the plate construct. This preferred embodiment of the present invention will shorten as required to maintain loaded contact of the bone portions to be fused, and if challenged, resist any forces such as those that would accompany cervical extension that would distract or destabilize the construct by elongating it. A further benefit of this embodiment is its ability to store and impart a compressive load across the fusion site referred to herein as "active dynamization" wherein energy stored in the system shortens the plate construct if conditions permit. This load can be applied by the surgeon at the time of surgery and/or be produced during the healing phase by harnessing the compressive loads such as occur randomly with neck motion. Compressive load within a physiological range has been shown to have a beneficial effect on the healing of bone. The induction of a compressive load across vertebral bodies to be fused, induces bone growth and when bone resorption occurs at the interface of the graft or implant and the vertebral bodies to be joined, those vertebral bodies are urged to move closer together, thus avoiding the formation of a gap therebetween and thereby acting to mitigate against pseudoarthrosis.

Alternatively, various embodiments of the present invention allow the surgeon to induce a desired amount of preload (compressive force) across the fusion site and to permit a desired amount of shortening of the construct—"active dynamization" should the opportunity occur; and yet lock the system to prevent any further shortening as might present a risk of deformity or be otherwise undesirable. Such a system urges the bone portions closer together.

In a preferred embodiment, a pre-load force can be applied to the plate segments such that while the plate segments may undergo no added motion initially, there is a selective force applied to the plate segments and the plate segments are capable of motion in only one direction, such that should resorption occur at one of the fusion interfaces then the plate segments are not only free to move in a direction toward one another, and only in that direction, but are also urged to do so to relieve that preload force. Such a system urges the vertebral bodies together over time as resorption permits.

Alternatively, in another embodiment of the plate of the present invention, a desired amount of preload (compressive force) may be induced across the fusion site to permit active dynamization should the opportunity occur, without locking the system such that after active dynamization is exhausted (if exhausted), then the plate will still allow passive dynamization to occur thereafter.

In another embodiment of the present invention, the plate includes a structural feature such as a groove, recess, slot, cam, or pivot, within its physical perimeter to engage a tool to cooperatively move segments of the plate towards each other. These embodiments of the present invention may be adapted to allow for passive, active, or active plus passive dynamization, and when used to store compressive load to allow for or prevent further motion thereafter. In a preferred version of this embodiment, the structural feature contained within the plate for generating the compressive load and/or shortening the plate, may also serve as the locking mechanism to limit the amount of further shortening possible.

Various embodiments of the plating system of the present invention provide one or more of the following advantages:

1. The requisite plate inventory is reduced as each plate may cover a range of sizes. The plate of the present invention includes multiple segments which may be of varying sizes wherein the segments are adapted to be assembled so as to be adjustable to provide for the size and spacing apart of the vertebral bodies to which the plate is to be applied. The plate may have its segments moved relative to one another so that the spacing between the plate segments may be adjusted so as to correspond to the actual distances between the vertebral bodies to be fused in a multi-segment construct for a more precise fit. The height of the discs and the vertebral bodies may vary level by level even in the same person. Thus, the ability to adjust the distances between the segments of the plates that correspond to the attachments to those vertebral bodies allows for a more precise fit of the plate to the spine with a reduced inventory of the number of plates required to do so.

2. It is possible to precisely contour each segment separately.

3. The plating system of the present invention reduces the risk that the plate construct will be discovered to be too short or too long after the attachment process has commenced.

4. It is possible to compress and dynamize levels selectively.

5. The fasteners that link the segments can be tightened to lock the segments after they are compressed or, alternatively, can allow for further motion of the plate segments together.

6. The same hardware can provide for passive dynamization or be rigidly fixed depending on the fasteners used to link plate segments.

7. The system can allow for passive dynamization, active dynamization, the combination of passive and active dynamization, or can convert body motion into active dynamization.

BRIEF DESCRIPTION OF THE DRAWINGS

FIG. 1B is an exploded top perspective view of a plate, a fastener, and a locking element in accordance with another preferred embodiment of the present invention.

FIG. 3A is a top plan view of the plate, fastener, and locking element of FIGS. 1A and 1B.

FIG. 3C is a top plan view of the plate, fastener, and locking elements of FIGS. 1C and 1D FIG. 4A is a bottom plan view of the plate, fastener, and locking element of FIG. 1A.

FIG. 4C is a bottom plan view of the plate, fastener, and locking elements of FIG. 1C.

FIG. 5A is an end view of the plates of FIGS. 1A-1D.

FIG. 6A is a side elevation view of the plates of FIGS. 1A and 1B.

FIG. 7A is a partial cross sectional view of the plates of FIGS. 1A and 1C.

FIG. 7B is a partial cross sectional view of the plates of FIGS. 1B and 1D.

FIG. 8A is an enlarged fragmentary view of the plates of FIGS. 1A and 1C and an alternative embodiment of a fastener in accordance with the present invention.

FIG. 8B is an enlarged fragmentary view of the plates of FIGS. 1B and 1D and an alternative embodiment of a fastener in accordance with the present invention.

FIG. 14A is a top plan view of the plates and fasteners of FIGS. 1A and 1B in a compressed state with the instrumentation of FIG. 13A shown in cross section engaging the ends of the plate to compress the plate in the direction of the arrows and with the instrumentation engaging the fastener.

FIG. 14C is a top plan view of the plates and fasteners of FIGS. 1C and 1D in a compressed state with the instrumentation of FIG. 13C shown in cross section engaging the ends of the plate to compress the plate in the direction of the arrows and with the instrumentation engaging the fastener.

FIG. 15A is a partial cross sectional view along line 15A-15A of FIG. 14A for the plate of FIG. 1A.

FIG. 15C is a partial cross sectional view along line 15C-15C of FIG. 14C for the plate of FIG. 1C.

FIG. 16C is a top perspective view of a plate, a fastener, and locking elements in accordance with another preferred embodiment of the present invention.

FIG. 17A is a top plan view of the plate and fastener of FIG. 16A.

FIG. 18A is a top plan view of the plate of FIG. 16A in an elongated state with fastener.

FIG. 21A is an exploded top perspective view of the plate, fastener, and locking element of FIG. 16A.

FIG. 21B is an exploded top perspective view of the plate, fastener, and locking element of FIG. 16A in accordance with another preferred embodiment of the present invention.

FIG. 21C is an exploded top perspective view of the plate, fastener, and locking elements of FIG. 16C.

FIG. 23A is a top plan view of the plate and fastener of FIG. 16A and a partial fragmentary perspective view of an instrument for compressing the plate and securing the fastener in accordance with another preferred embodiment of the present invention.

FIG. 23C is a top plan view of the plate, fastener, and locking elements of FIG. 16C and a partial fragmentary perspective view of an instrument for compressing the plate and securing the fastener in accordance with another preferred embodiment of the present invention.

FIG. 24A is an enlarged cross sectional view of the plate of FIG. 16A with the instrument of FIG. 23A engaging the fastener and positioned within the plate.

FIG. 24B is an enlarged cross sectional view of another preferred embodiment of the plate of FIG. 16A with the instrument of FIG. 23A engaging the fastener and positioned within the plate.

FIG. 24C is an enlarged cross sectional view of the plate of FIG. 16C with the instrument of FIG. 23C engaging the fastener and positioned within the plate.

FIG. 32A is a top plan view of the plates, fasteners, and locking element of FIGS. 30A and 30B.

FIG. 32C is a top plan view of the plates, fasteners, and locking elements of FIGS. 30C and 30D.

FIG. 33A is a bottom plan view of the plate and fasteners of FIG. 30A.

FIG. 33C is a bottom plan view of the plate, fasteners, and locking elements of FIG. 30C.

FIG. 34A is a side elevation view of the plates of FIGS. 30A and 30B.

FIG. 34C is a side elevation view of the plates of FIGS. 30C and 30D.

FIG. 35C is a partial cross sectional view along the longitudinal axis of the plate of FIG. 30C.

FIG. 36C is a top plan view of the plates in an elongated position, fasteners, and locking elements of FIGS. 30C and 30D.

FIG. 38A is a top plan view of one of the plates of FIGS. 30A and 30B in a compressed state with the instrumentation of FIG. 37A shown in cross section engaging the ends of the plate to compress the plate in the direction of the arrows, an alternative embodiment of instrumentation for engaging an intermediary portion of the plate to compress the plate in the direction of the arrows in dotted line, and instrumentation engaging the fastener and positioned within the plate.

FIG. 38C is a top plan view of one of the plates of FIGS. 30C and 30D in a compressed state with the instrumentation of FIG. 37C shown in cross section engaging the ends of the plate to compress the plate in the direction of the arrows, an alternative embodiment of instrumentation for engaging an intermediary portion of the plate to compress the plate in the direction of the arrows in dotted line, and instrumentation engaging the fastener and positioned within the plate.

FIG. 39A is a side elevation view of the plate of FIG. 38A with the instrumentation shown in partial fragmentary, hidden line, and cross sectional views.

FIG. 39C is a side elevation view of the plate of FIG. 38C with the instrumentation shown in partial fragmentary, hidden line, and cross sectional views.

FIG. 40A is an exploded top perspective view of a plate, fasteners, and a locking element in accordance with another preferred embodiment of the present invention.

FIG. 40D is an exploded top perspective view of a plate, fasteners, and locking elements in accordance with another preferred embodiment of the present invention.

FIG. 41 is a top plan view of a plate, fasteners, and locking elements in accordance with another preferred embodiment of the present invention.

FIG. 42 is an exploded top plan view of a plate, fasteners, and locking elements in accordance with another preferred embodiment of the present invention.

FIG. 43 is an enlarged fragmentary cross sectional view of the plate, locking element, and bone screws of FIG. 42.

FIG. 44 is an enlarged fragmentary cross sectional view of a plate, locking element, and bone screws in accordance with another embodiment of the present invention.

DETAILED DESCRIPTION OF THE DRAWINGS

Figure 1A:
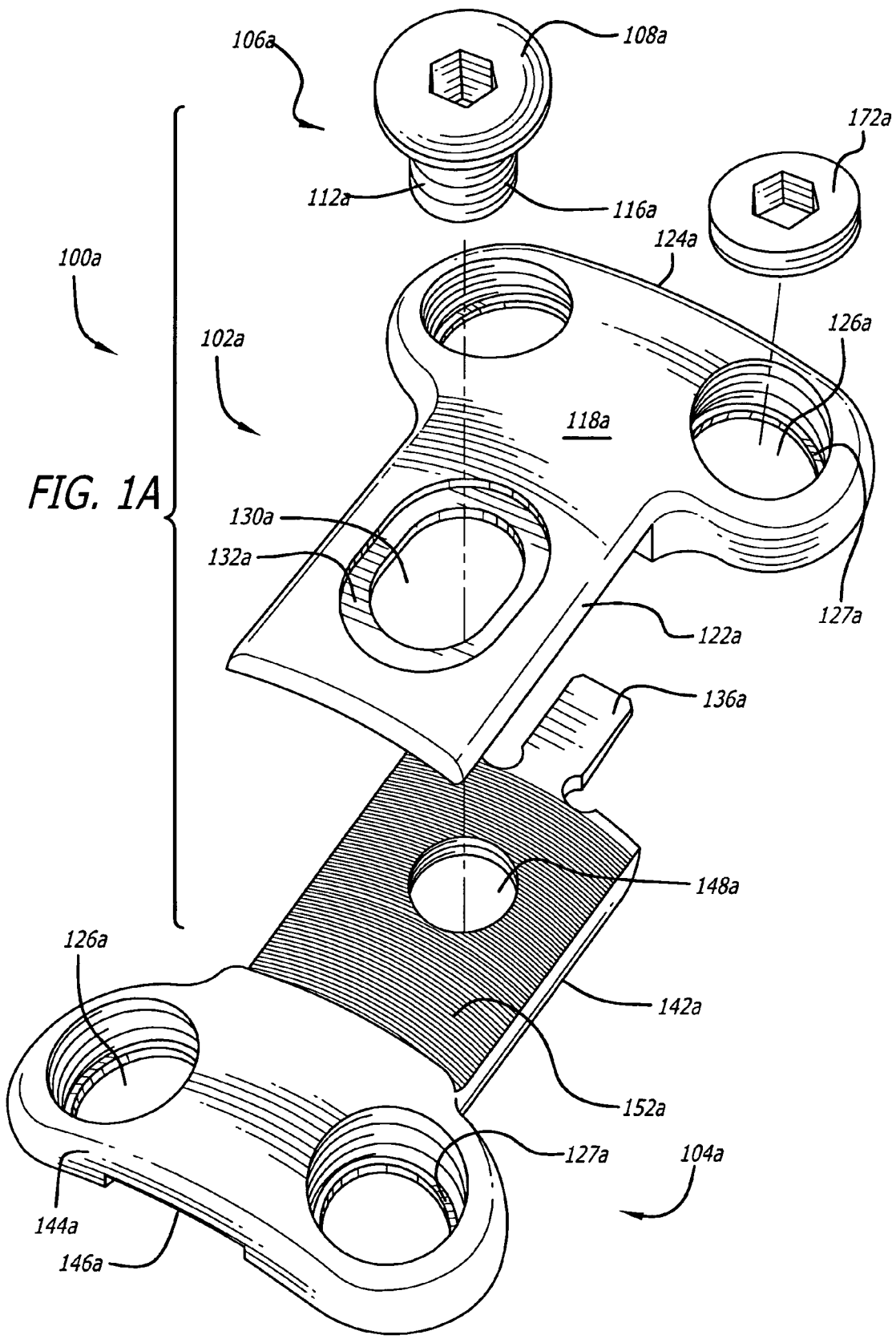
FIG. 1A is an exploded top perspective view of a plate, a fastener, and a locking element in accordance with a preferred embodiment of the present invention.
Figure 1C:
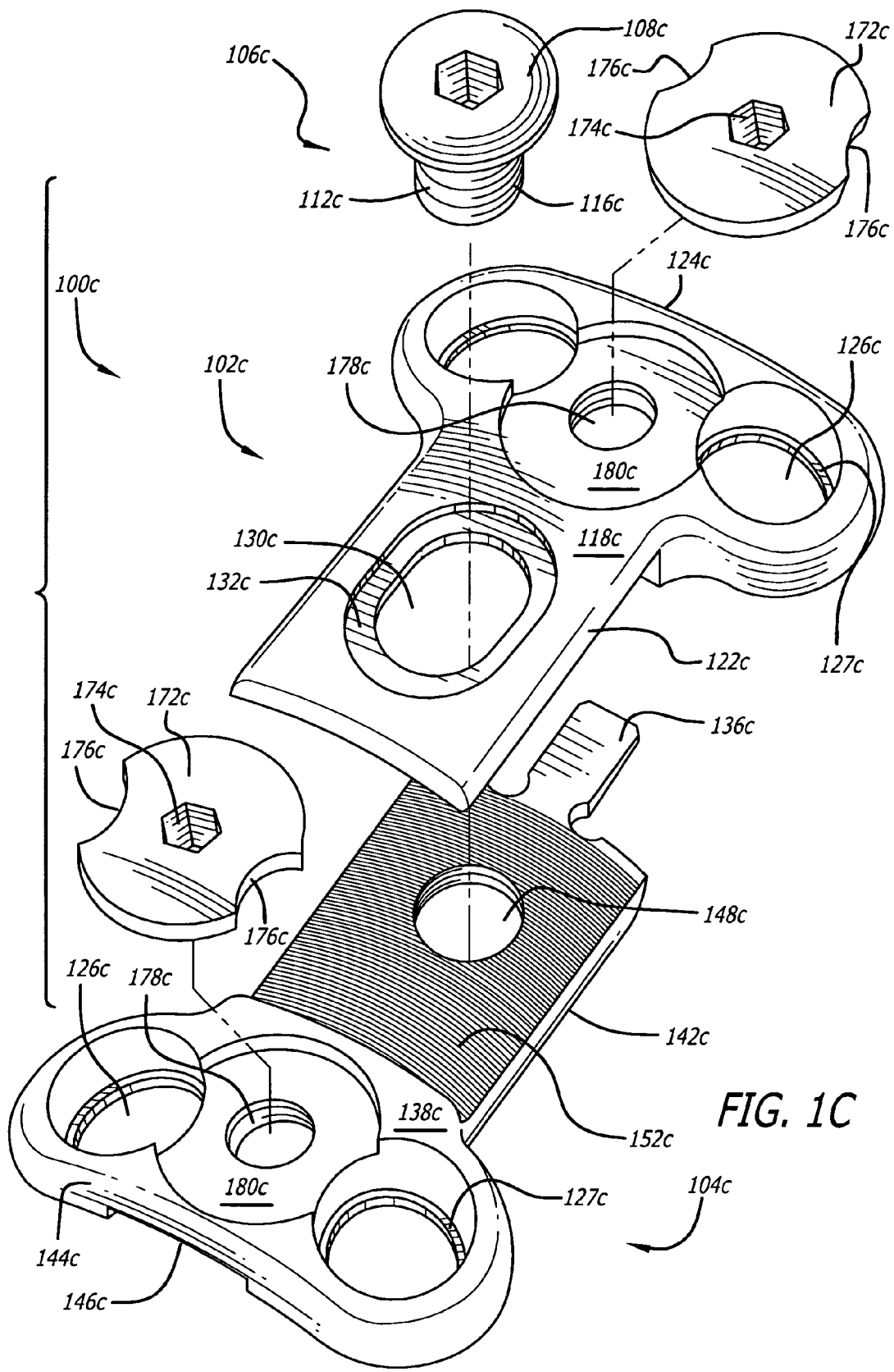
FIG. 1C is an exploded top perspective view of a plate, a fastener, and locking elements in accordance with another preferred embodiment of the present invention.
Figure 1D:
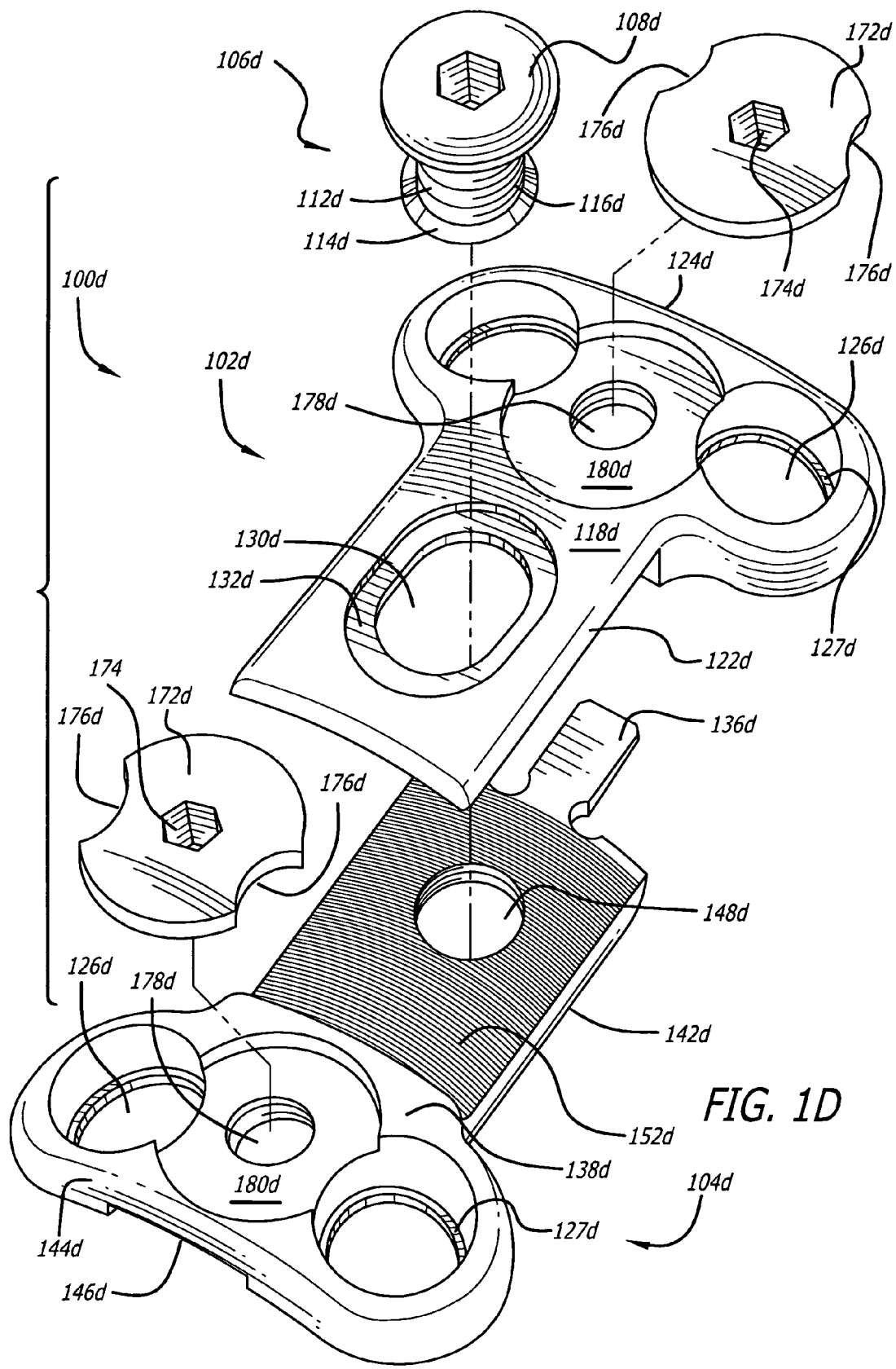
FIG. 1D is an exploded top perspective view of a plate, a fastener, and locking elements in accordance with another preferred embodiment of the present invention.

Reference will now be made in detail to the present preferred embodiments (exemplary embodiments) of the invention, examples of which are illustrated in the accompanying drawings. Wherever possible, the same reference numbers will be used throughout the drawings to refer to the same or like parts.

The present invention is for use in the cervical spine where dynamization is highly desired to prevent distraction pseudoarthrosis and to maintain a compressive load across the fusion interfaces. The present invention in one preferred embodiment is directed to a cervical plate generally having at least two movable segments that are attached to the vertebral bodies to be fused and connected in such a way as to permit dynamization of the vertebral bodies preferably along the longitudinal axis of the plate. The movement of the segments relative to one another may be accompanied by a reduction in the overall length of the plate.

Where possible, the reference numerals in the figures are followed by a letter "a", "b", "c", or "d" corresponding to preferred embodiments of the present invention, respectively. For example, a description of a feature identified by a reference numeral followed by the reference letter "a" and also applicable to a feature identified by a reference numeral followed by a letter "b", "c", or "d" will not be repeated for each of the corresponding reference numerals.

FIGS. 1A, 2A, 3A, 4A, 5A, 6A and 7A show a preferred embodiment of a cervical plate 100a in accordance with the present invention. Plate 100a is preferably formed of a first segment 102a and a second segment 104a in moveable relationship to one another. First and second segments 102a, 104a can be of various lengths and/or configurations such that when the segments are assembled preferably overlapping at least in part, plates of various lengths and/or configurations can be formed to cover a range of sizes. First and second segments 102a, 104a can be of the same or different lengths and can be coupled to each other or to an intermediate segment as shown in FIGS. 29A, 30A, 31A, 32A, 33A, 34A, 35A, 36A, 37A, 38A, 39A, and -40A and described below in connection with other preferred embodiments of the present invention. The overall length of plate 100a and the spacing of segments 102a, 104a can be adjusted by moving segments 102a, 104a relative to one another.

In this preferred embodiment of the present invention, a detachable fastener 106a couples together first and second segments 102a, 104a. Fastener 106a is configured to be detachably attached to at least one of first and second segments 102a, 104a, to permit the assembly of two or more plate segments. Fastener 106a is detachable to permit for the assembly of the plate segments by the surgeon and allows for the complete uncoupling of first and second segments 102a, 104a from one another. As used herein, "detachable fastener" is defined as a fastener that can be assembled by the surgeon at the time of use and once attached is meant to still be removable and then reattachable by the surgeon. As shown in FIG. 7A, fastener 106a, for example, may be embodied in the form of a screw having a head 108a, a shaft 112a, and a thread 116a.

As shown in FIG. 8A, in another preferred embodiment fastener 106a' may be configured to be tightened to only one of first and second plate segments 102a, 104a so as to permit movement of first and second segments 102a, 104a relative to one another when fastener 106a' is fully tightened. For example, fastener 106a' may have a shoulder 110a adapted to bear upon second segment 104a as indicated by arrow C. Shoulder 110a is dimensioned so as to create a gap 111a between head 108a' and first segment 102a so as to still permit a specific and desired motion of first and second segments 102a, 104a relative to one another when fastener 106a' is fully tightened. The limited motion of first and second segments 102a, 104a relative to one another provides for dynamization of the spinal segment to be fused in that those vertebral bodies are allowed to move closer together to maintain contact.

Figure 2A:
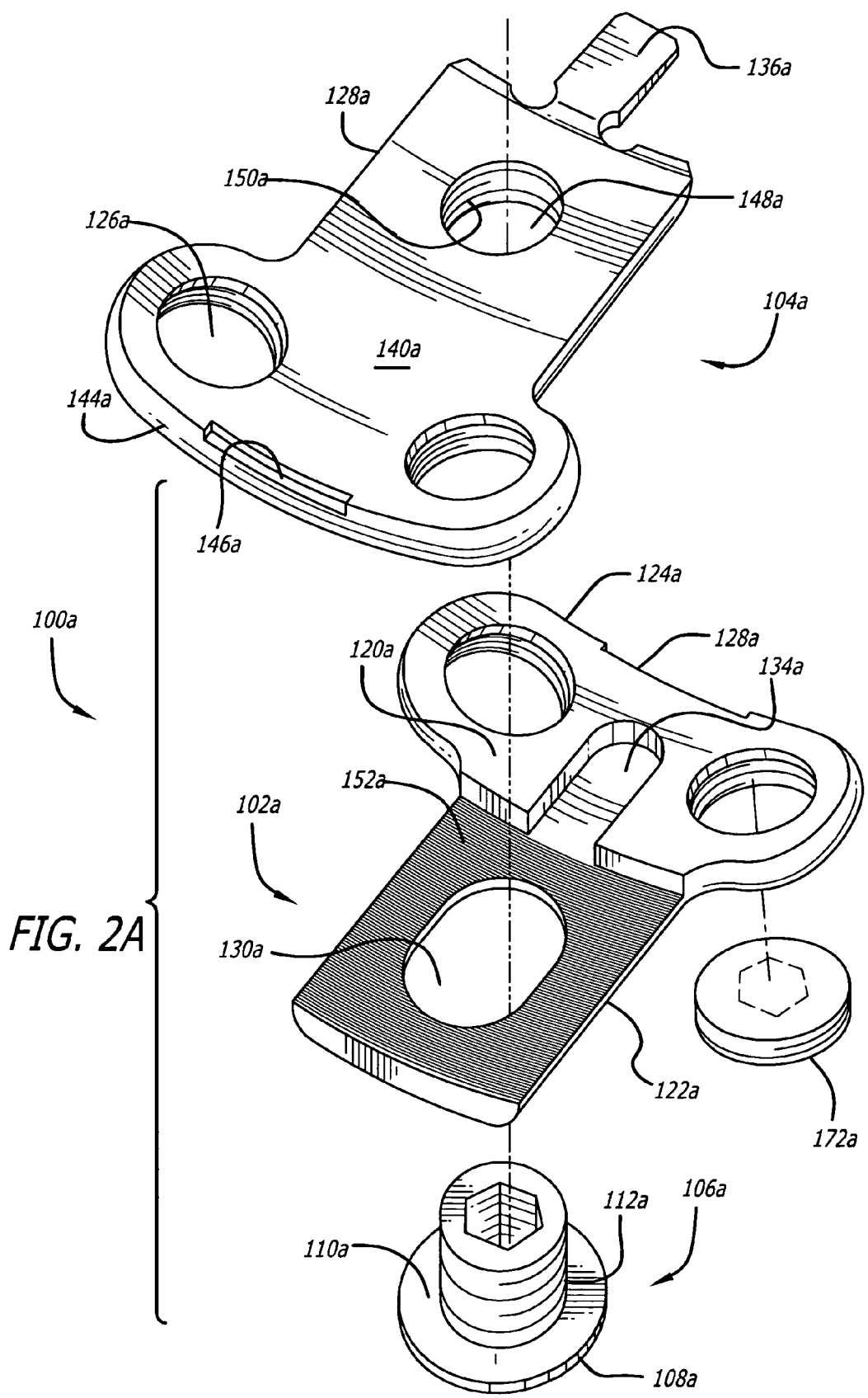
FIG. 2A is an exploded bottom perspective view of the plate, fastener, and locking element of FIG. 1A.

As shown in FIGS. 1A and 2A, first segment 102a preferably has an upper surface 118a, a lower surface 120a, a medial portion 122a, and an end 124a. First segment 102a preferably includes bone screw receiving holes 126a proximate end 124a. Bone screw receiving hole 126a is preferably configured to receive a single bone screw or the bone screw receiving holes also may be configured to receive more than one bone screw. By way of example only and not limitation, a bone screw receiving hole may be in the form of a slot sized to receive at least two bone screws.

Preferably, at least two of bone screw receiving holes 126a may be oriented in plate 100a to overlie the anterior aspect of a single cervical vertebral body adjacent a disc space to be fused, though the invention is not so limited. For example, a first pair of bone screw receiving holes 126a may be configured to overlie the anterior aspect of a first cervical vertebral body adjacent a disc space to be fused and at least a second pair of bone screw receiving holes 126a may be oriented in plate 100a to overlie the anterior aspect of a second cervical vertebral body adjacent the disc space to be fused.

Bone screw receiving hole 126a may, though need not be, configured to form an interference fit with at least a portion of the trailing end of a properly dimensioned bone screw to be received therein. Bone screw receiving holes 126a may be configured, for example only, so that at least one of bone screw receiving holes 126a may hold a bone screw in a fixed relationship to the plate or may hold a bone screw in a moveable relationship, such as a variable angular relationship, described below. By way of example only and not limitation, bone screw receiving hole 126a may have a reduced dimension proximate lower surface 120a of segment 102a to form a seat 127a. Seat 127a may have a surface adapted to contact at least a portion of a bone screw inserted therein. The surface may be at least in part planar, at least in part curved, or have any other configuration suitable for contacting at least a portion of a bone screw.

End 124a of first segment 102a may also include a tool engagement area 128a adapted to cooperatively engage instrumentation for holding plate 100a and instrumentation for moving first and second segments relative to one another to induce a desired amount of compressive force across the fusion sites and to permit a desired amount of shortening of plate 100a. Medial portion 122a preferably has a fastener receiving opening 130a adapted to accommodate fastener 106a to couple first and second segments 102a, 104a to one another.

Fastener receiving opening 130a is preferably configured to permit selected movement of fastener 106a therein and to permit selected motion of first and second segments 102a, 104a along the longitudinal axis of plate 100a. Fastener receiving opening 130a may include a shoulder 132a recessed from upper surface 118a of first segment 102a adapted to contact the underside of head 108a of fastener 106a in the tightened position to prevent movement of first and second segments 102a, 104a relative to one another. Alternatively, if a fastener 106a' is used, shoulder 110a contacts second segment 104a and the underside of head 108a' is positioned relative to shoulder 132a to permit movement of first and second segments 102a, 104a relative to each other along the longitudinal axis of the plate when in the tightened position providing for dynamization of the vertebral bodies to be fused to occur, if needed. Fastener 106a and fastener receiving opening 130a cooperate to prevent complete uncoupling of first and second segments 102a, 104a from one another when fastener 106a is installed. For example, fastener receiving opening 130a may be configured to prevent head 108a of fastener 106a from passing therethrough.

Lower surface 120a of first segment 102a includes a tab receiving recess 134a for receiving a tab 136a described below.

Second segment 104a has an upper surface 138a, a lower surface 140a, a medial portion 142a, and an end 144a. Second segment 104a preferably has bone screw receiving holes 126a proximate end 144a. End 144a may also include a tool engagement area 146a adapted to cooperatively engage instrumentation for holding plate 100a and instrumentation for moving first and second segments 102a, 104a relative to one another to induce a desired amount of compressive force across the fusion site and to permit a desired amount of shortening of plate 100a. Medial portion 142a preferably includes a fastener receiving opening 148a for receiving a portion of fastener 106a. As first and second segments of plate 100a are modular and assembleable, fastener receiving opening 148a is configured to permit detachable attachment of fastener 106a.

Fastener receiving opening 148a preferably has a thread 150a adapted to engage with thread 116a of fastener 106a. The threaded engagement of fastener 106a to fastener receiving opening 148a permits first segment 102a and second segment 104a to be attached to each other when fastener 106a is sufficiently rotated and tightened. As fastener 106a is rotated further, first and second segments 102a, 104a are secured together and locked and do not move relative to each other. Alternatively, if fastener 106a' shown in FIG. 8A is used in the tightened position, first and second segments 102a, 104a are capable of moving relative to each other.

Lower surfaces 120a, 140a of first and second segments 102a, 104a are preferably at least in part concave along at least a portion of the longitudinal axis of the plate, may be biconcave at least in part, that is, concave along the longitudinal axis of plate 100a and concave transverse to the longitudinal axis of the plate, or may have any shape suitable for the intended purpose transverse to the longitudinal axis of the plate. A person skilled in the art will appreciate that plate 100a may be adapted for other curvatures or have no curvature without departing from the intended purpose within the broad scope of the present invention. Lower surfaces 120a, 140a are preferably adapted to contact at least a portion of the vertebral bodies to be fused and may be configured to conform to the anterior aspect of at least a portion of the vertebral bodies.

Second segment 104a preferably includes a tab 136a extending from medial portion 142a. Tab 136a is configured to cooperatively engage a tab receiving recess 134a in the lower surface 120a of first segment 102a. Tab 136a acts as a spring to maintain first and second segments 102a, 104a aligned along the longitudinal axis of plate 100a. Tab 136a also functions to limit movement of first segment 102a in a direction transverse to longitudinal axis of plate 100a to prevent end 124a from dropping down beyond a desired position. This limited movement of first segment 100a prevents medial portion 122a of first segment 102a from lifting away from medial portion 142a beyond a desired position, so that ratchetings 150a are not overly separated and rendered less effective as described in more detail below. It is appreciated that other configurations of segments 102a, 104a are possible to hold apart segments 102a, 104a and to limit movement of the segments in a direction transverse to the longitudinal axis of the plate. For example, the longitudinal curvatures of first and second segments 102a, 104a can be slightly different to spring apart segments 102a, 104a. For example, the radius of curvature of the lower surface of segment 102a may be different than the radius of curvature of the upper surface of segment 104a.

At least a portion of lower surface 120a of first segment 102a and upper surface 138a of second segment 104a are preferably configured to interdigitate with one another to permit selected adjustment of the length of plate 100a. For example, lower surface 120a and upper surface 138a may include a surface configuration, such as ratchetings 152a, configured to cooperatively interdigitate to permit selected and sequential movement along the longitudinal axis of plate 100a. The ratchetings are preferably biased to allow movement in one preferred direction along the longitudinal axis of the plate so as to allow shortening of the plate and resist lengthening of the plate.

Figure 9A:
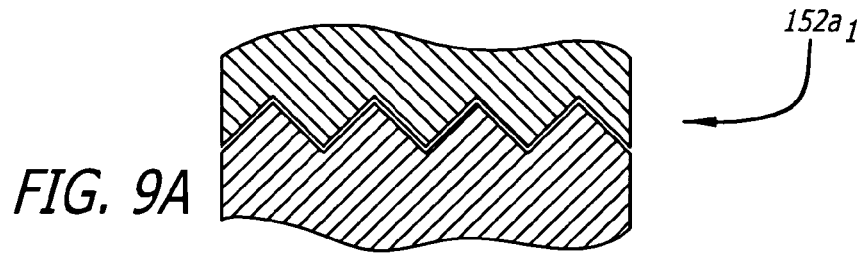
FIG. 9A is an enlarged fragmentary cross sectional view of an embodiment of the ratchetings in the upper and lower portions of the plates of FIGS. 1A-1D in a first position.
Figure 10A:
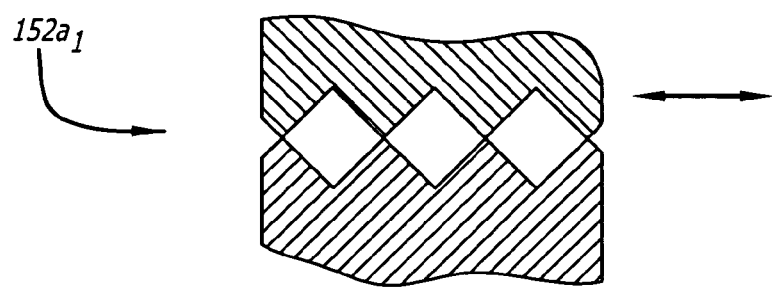
FIG. 10A is a fragmentary cross sectional view of FIG. 9A in a second position.

FIGS. 9A and 10A show an embodiment of ratchetings having a configuration that is useful if no movement of first and second segments 102a, 104a is desired after fastener 106a is tightened. A preferred angular relationship of the cross section of ratchetings $152a_1$ is a 45-45-90 degree triangular relationship. As shown in FIG. 9A, in a first position, the peaks and valleys of ratchetings $152a_1$ are cooperatively mating. Ratchetings $152a_1$ permit for the fixed positioning of first and second segments 102a, 104a relative to one another to create a selected length of plate 100a. As shown in FIG. 10A, the peaks and valleys are separated to permit movement of the first and second segments in the directions of the arrows along the longitudinal axis of plate 100a. In order for first and second segments 102a, 104a to move relative to one another, there must be sufficient freedom of movement for the segments to move apart in order to clear the height of the peaks of ratchetings $152a_1$. Accordingly, in a preferred embodiment fastener 106a is configured to have at least one position that permits movement of the first and second segments along the longitudinal axis of plate 100a as well as along an axis transverse to the longitudinal axis of plate 100a such that ratchetings 152a can move apart. Fastener 106a can be tightened to a second position to resist or prevent movement of segments 102a, 104a relative to one another. For example, movement of segments 102a, 104a can be resisted in a direction along at least a portion of the longitudinal axis of plate 100a.

Figure 11A:
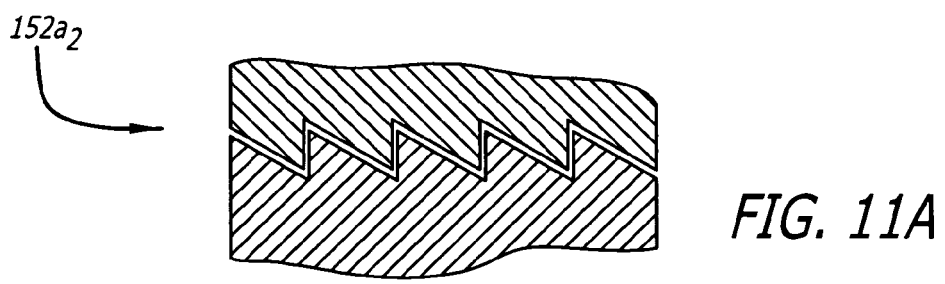
FIG. 11A is an enlarged fragmentary cross sectional view of a preferred embodiment of the ratchetings in the upper and lower portions of the plates of the present invention in a first position.
Figure 12A:
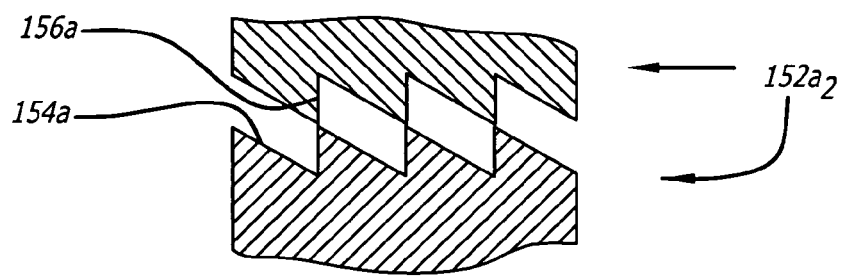
FIG. 12A is a fragmentary cross sectional view of FIG. 11A in a second position.

FIGS. 11A and 12A show another preferred embodiment of ratchetings $152a_2$ having a forward-facing configuration for permitting movement in a single direction. The configuration of ratchetings $152a_2$ is useful when movement of first and second segments 102a, 104a is desired to permit further shortening of the plate. A preferred angular relationship of the triangular cross section of ratchetings $152a_2$ is a 30-60-90 degree triangular relationship. As shown in FIG. 12A, due to the forward facing angle of ratchetings $152a_2$, sliding movement of first and second segments 102a, 104a in the direction, as indicated by the arrow, along the longitudinal axis of plate 100a is facilitated by the ramped surface 154a. In contrast, sliding movement in the opposite direction is restricted by vertical wall 156a. Movement of segments 102a, 104a is limited to a single direction with ratchetings $152a_1$ and by limiting the separation of segments 102a, 104a along an axis transverse to the longitudinal axis of plate 100a with fastener 106a or 106a'.

In a preferred embodiment, fastener 106a or 106a' is configured to have at least one position that permits movement of first and second segments 102a, 104a in both directions along the longitudinal axis of plate 100a as well as along an axis transverse to the longitudinal axis of plate 100a such that ratchetings $152a_2$ can move apart. For example, in a first position fastener 106a can be less than fully tightened to plate 100a as desired by the surgeon to permit movement of first and second segments relative to each other. Fastener 106a' can further have a second position that permits movement of segments 102a, 104a relative to one another only in a single direction along the longitudinal axis of plate 100a and limits movement along an axis transverse to the longitudinal axis of plate 100a. Therefore, plate 100a can be shortened if the distance between the two adjacent vertebral bodies decreases, even after plate 100a is installed, so that the vertebral bodies are not held apart by plate 100a, to prevent the occurrence of pseudoarthrosis. One of the benefits of a forward-facing configuration of ratchetings $152a_2$ is the ability to store and impart a compressive load across the fusion site. The compressive load stored may be applied by the surgeon and/or compressive loads that occur randomly with neck motion during the healing phase. First and second segments 102a, 104a may be pre-adjusted to correspond to the appropriate size and spacing of the adjacent vertebral bodies to be fused prior to placement of plate 100a against the vertebral bodies by moving first and second segments 102a, 104a relative to one another while fastener 106a is only partially tightened for the purpose of appropriately adjusting the length of the plate. Then, fastener 106a may be further tightened to secure first and second segments 102a, 104a in the desired position.

Plates 100a and 100b preferably include at least one bone screw lock adapted to lock to the plate only a single bone screw inserted into one of the bone screw receiving holes. The plates of the present invention may include more than one bone screw lock, each lock being adapted to lock to the plate only a single bone screw inserted into one of the bone screw receiving holes. Preferably, the bone screw lock physically blocks the bone screw from unwanted loosening or unwanted backing out from the plate.

FIGS. 47a-47d show preferred embodiments of locking elements for locking bone screws in accordance with the present invention. For example, the bone screw locks may be in the form of a screw, a rivet, a cap, or a cover. It is appreciated that any locking element for locking a single one of the bone screws known to one of ordinary skill in the art would be within the scope of the present invention.

Figure 47A:
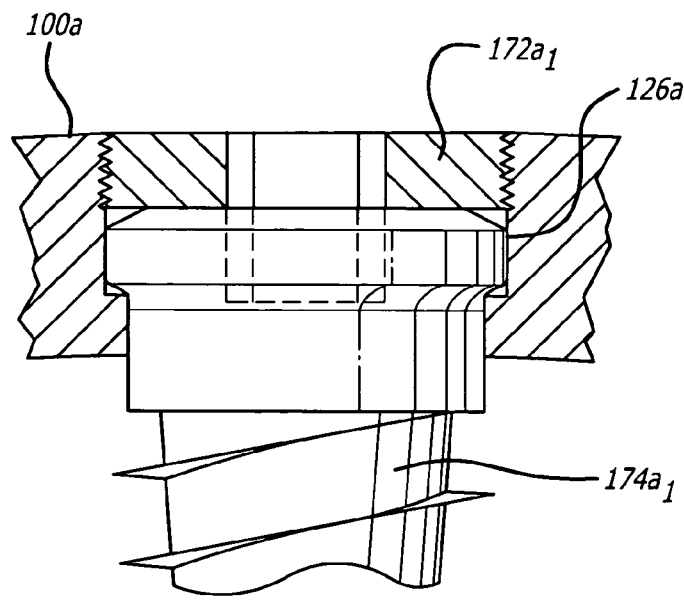
FIG. 47a is an enlarged fragmentary cross sectional view of a locking element and bone screw in accordance with a preferred embodiment of the present invention.

FIG. 47a shows an enlarged fragmentary cross sectional view of a locking element $172a_1$ and a bone screw $174a_1$. Locking element $172a_1$ threadably engages bone screw receiving hole 126a to prevent bone screw $174a_1$ from backing out. In this embodiment, locking element $172a_1$ locks bone screw $174a_1$ in a fixed relationship to plate 100a.

Figure 47B:
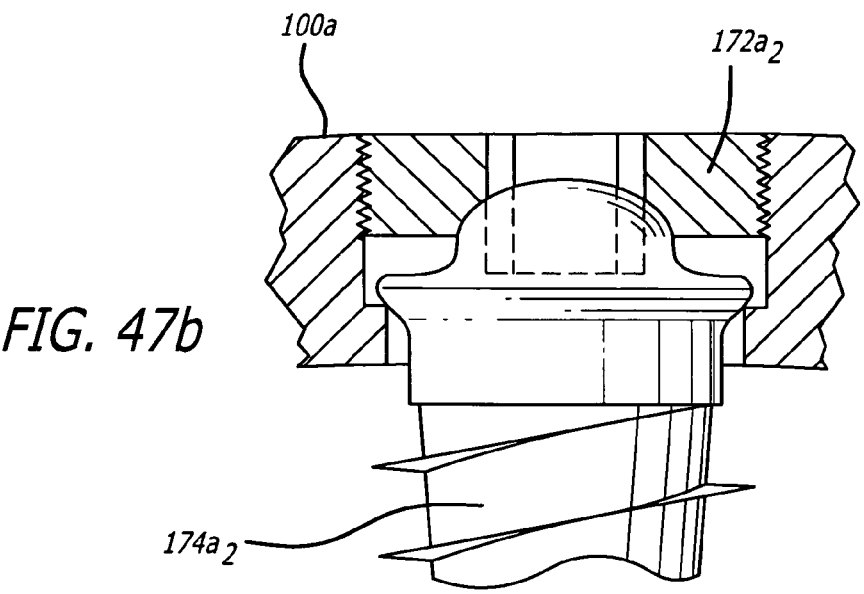
FIG. 47b is an enlarged fragmentary cross sectional view of a locking element and bone screw in accordance with another preferred embodiment of the present invention.

FIG. 47b is an enlarged fragmentary cross sectional view of a locking element $172a_2$ and a bone screw $174a_2$. Locking element $172a_2$ threadably engages bone screw receiving hole $126a$ to prevent bone screw $174a_2$ from backing out. In this embodiment, locking element $172a_2$ is adapted to hold bone screw $174a_2$ in an angular relationship to plate $100a$. Examples of preferred fixed-angled single locking elements are taught by Michelson in U.S. Pat. No. 6,139,550, (the '550 patent) entitled "Skeletal Plating System," the disclosure of which is hereby incorporated by reference herein. Locking element $172a_2$ may also permit movement of bone screw $174a_2$ relative to plate $100a$.

Figure 47C:
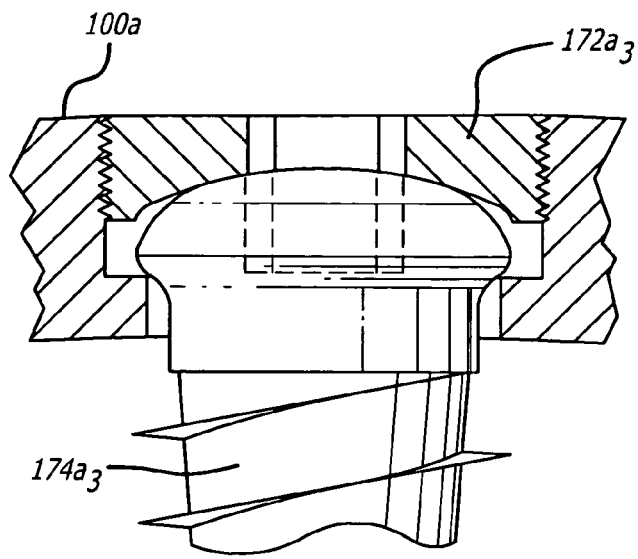
FIG. 47c is an enlarged fragmentary cross sectional view of a locking element and bone screw in accordance with yet another embodiment of the present invention.
Figure 47D:
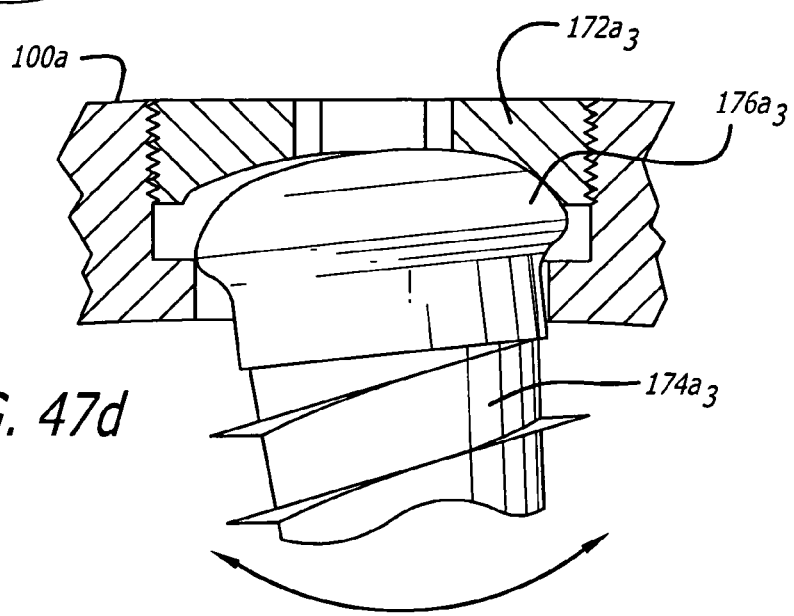
FIG. 47d is an enlarged fragmentary cross sectional view of the locking element and bone screw of FIG. 47c in an angled position.

FIGS. 47c and 47d are enlarged fragmentary cross sectional views of a locking element $172a_3$ and bone screw $174 a_3$ in accordance with another embodiment of the present invention. Locking element $172 a_3$ threadably engages bone screw receiving hole $126a$ to prevent bone screw $174 a_3$ from backing out. In this embodiment, locking element $172 a_3$ is adapted to hold bone screw $174 a_3$ in an angular relationship to plate $100a$. Locking element $172 a_3$ may also permit movement of bone screw $174 a_3$ relative to plate $100$. Locking element $172 a_3$ is adapted to adjustably lock bone screw $174 a_3$ in a variable angle relationship relative to plate $100a$. Bone screw $174 a_3$ preferably has a rounded head $176 a_3$ that cooperates with the bottom surface of single locking element $172 a_3$, thus allowing screw $174 a_3$ to move relative to plate $100a$. Examples of preferred variable-angled single locking elements are taught by Michelson in the '550 patent the disclosure of which is hereby incorporated by reference herein.

Figure 47E:
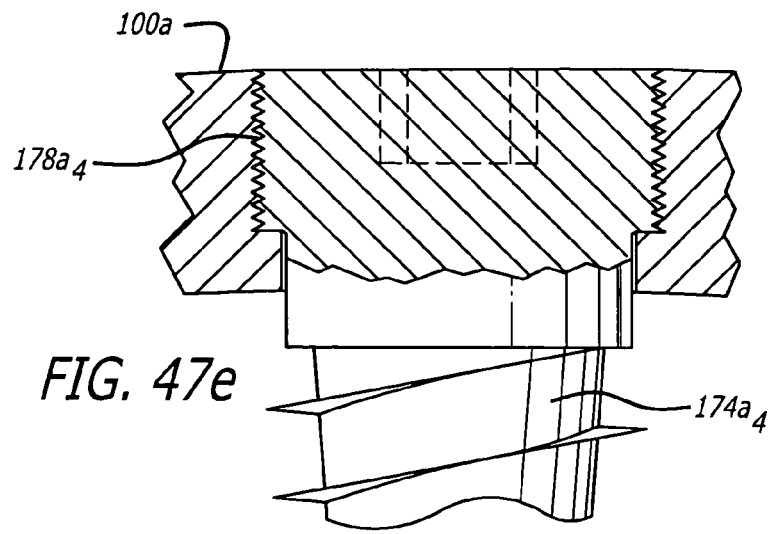
FIG. 47e is an enlarged fragmentary cross sectional view of a self-locking bone screw in accordance with a further embodiment of the present invention.

FIG. 47e is an enlarged fragmentary cross sectional view of a self-locking bone screw $174a_4$ in accordance with another embodiment of the present invention. Bone screw $174a_4$ has thread $178a_4$ adapted to threadably engage bone screw receiving hole $126a$. The thread pattern of thread $178a_4$ is has a tighter pitch than the thread pattern of the bone engaging thread of bone screw $174a_4$. The different thread pitches prevent bone screw $174a_4$ from backing out after installation is completed.

It is appreciated that various types of bone screws and single lock systems may be utilized with the plates of the present invention.

With appropriate embodiments of the plates described herein, the surgeon may induce a desired amount of "preload," or compressive force across the fusion site after plate attachment by moving first and second segments $102a$, $104a$ toward one another to shorten the length of plate $100$ as desired. Inducing a preload enhances fusion by maintaining a compressive force between adjacent vertebral bodies and reducing the chance that gaps might develop as new living bone replaces the dead bone during the fusion process.

Figure 13A:
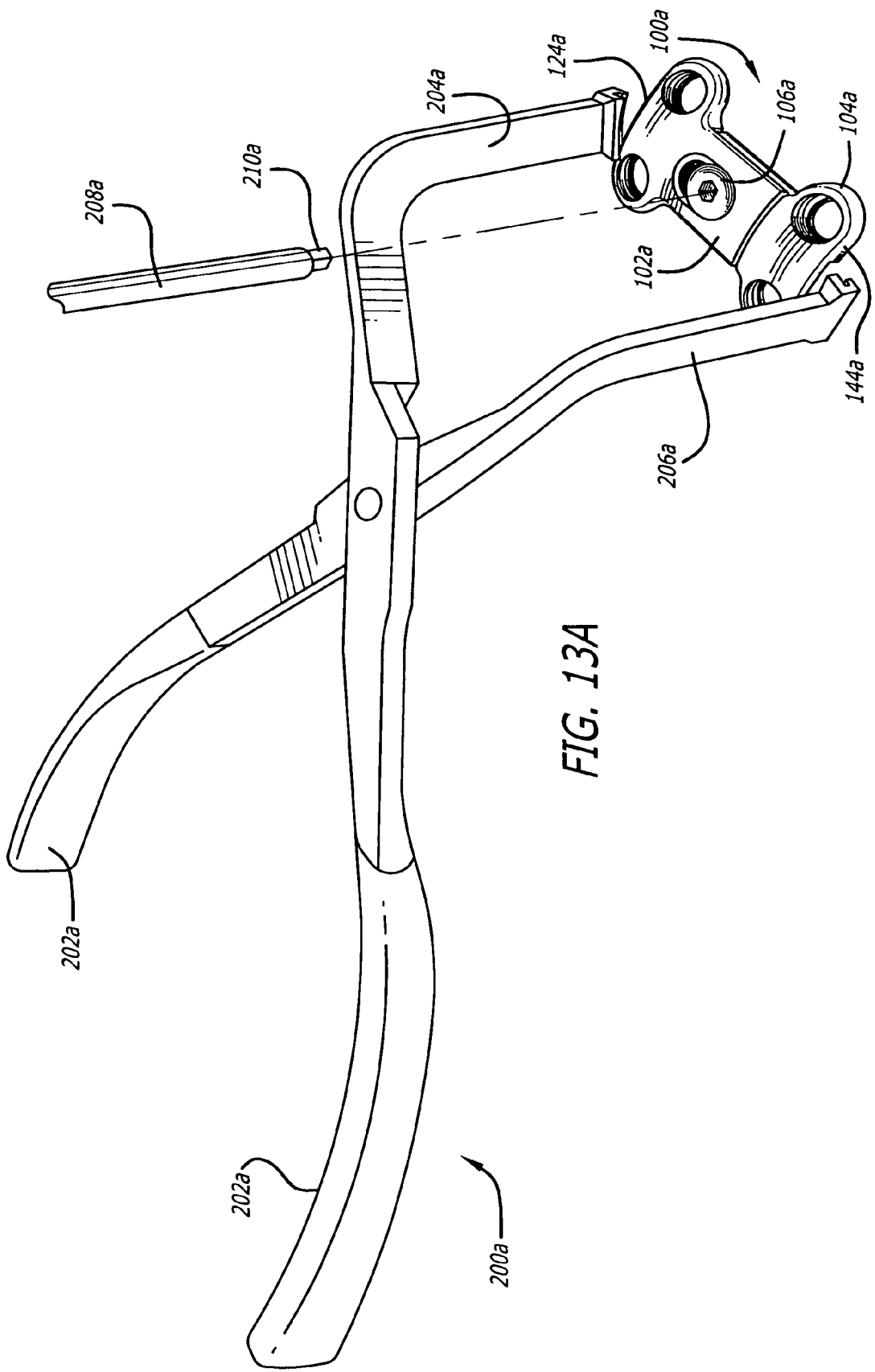
FIG. 13A is a top perspective view of the plates and fasteners of FIGS. 1A and 1B and instrumentation for compressing the plates and instrumentation for locking the fasteners in accordance with a preferred embodiment of the present invention.
Figure 13C:
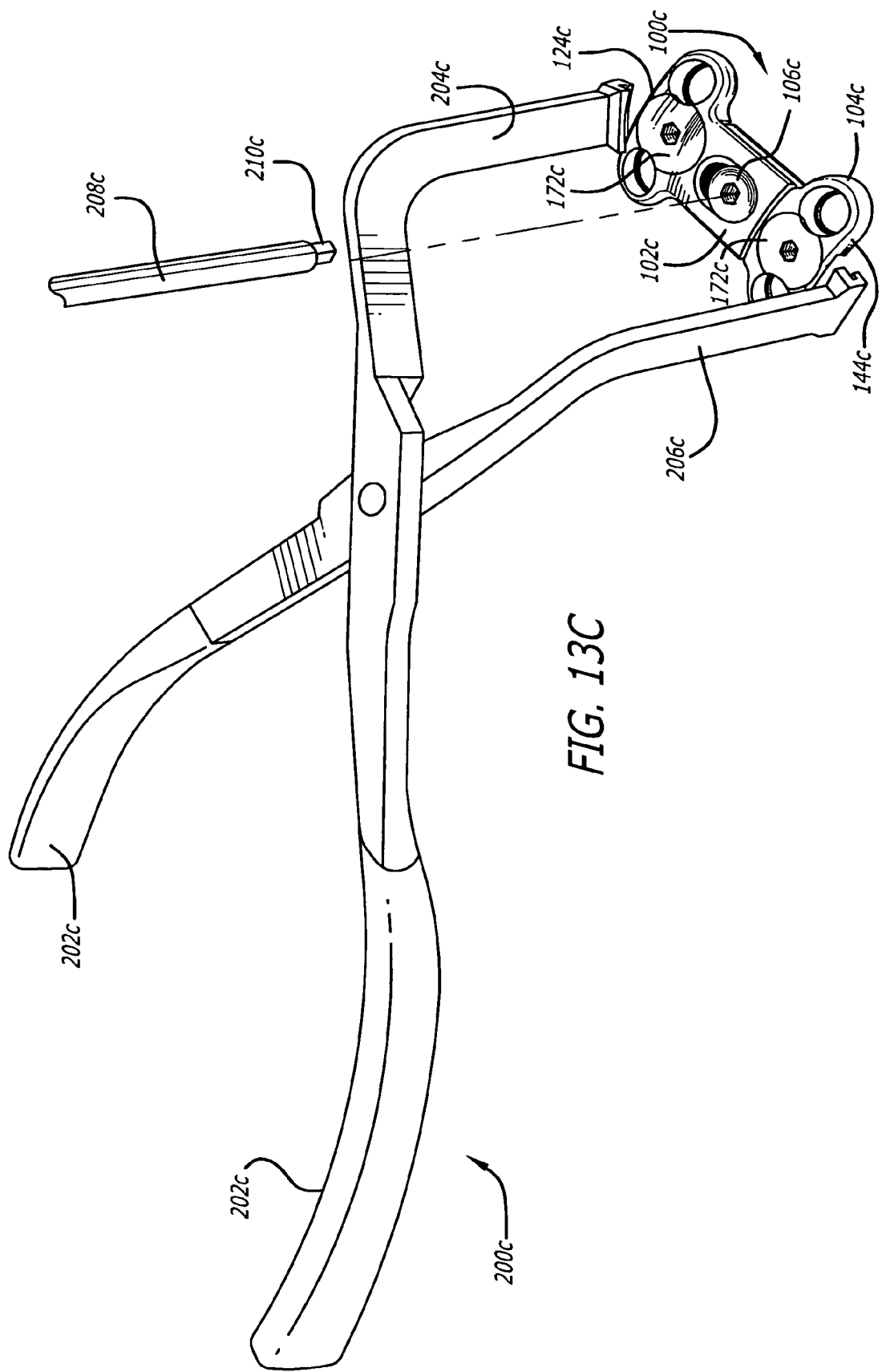
FIG. 13C is a top perspective view of the plates and fasteners of FIGS. 1C and 1D and instrumentation for compressing the plates and instrumentation for locking the fasteners in accordance with a preferred embodiment of the present invention.
Figure 15B:
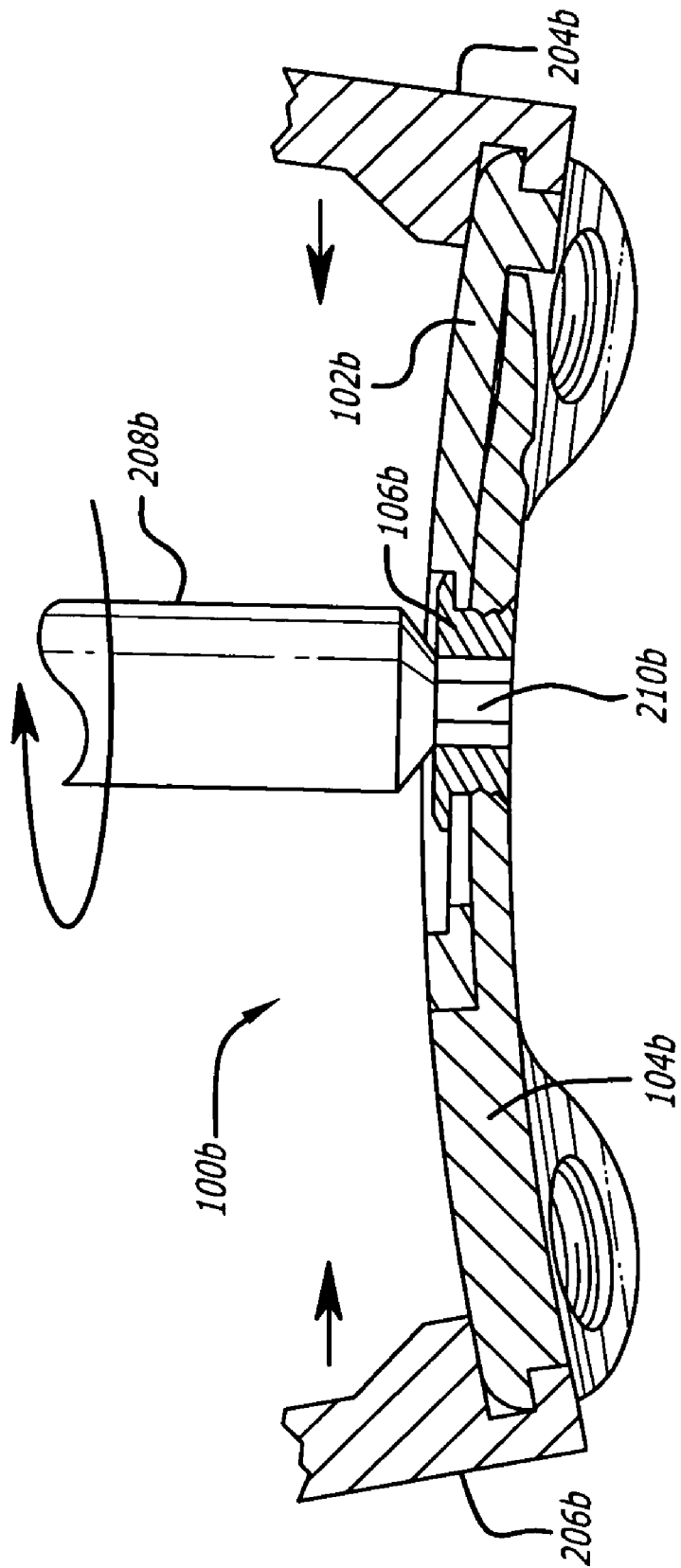
FIG. 15B is a partial cross sectional view along line 15A-15A of FIG. 14A for the plate of FIG. 1B.
Figure 15D:
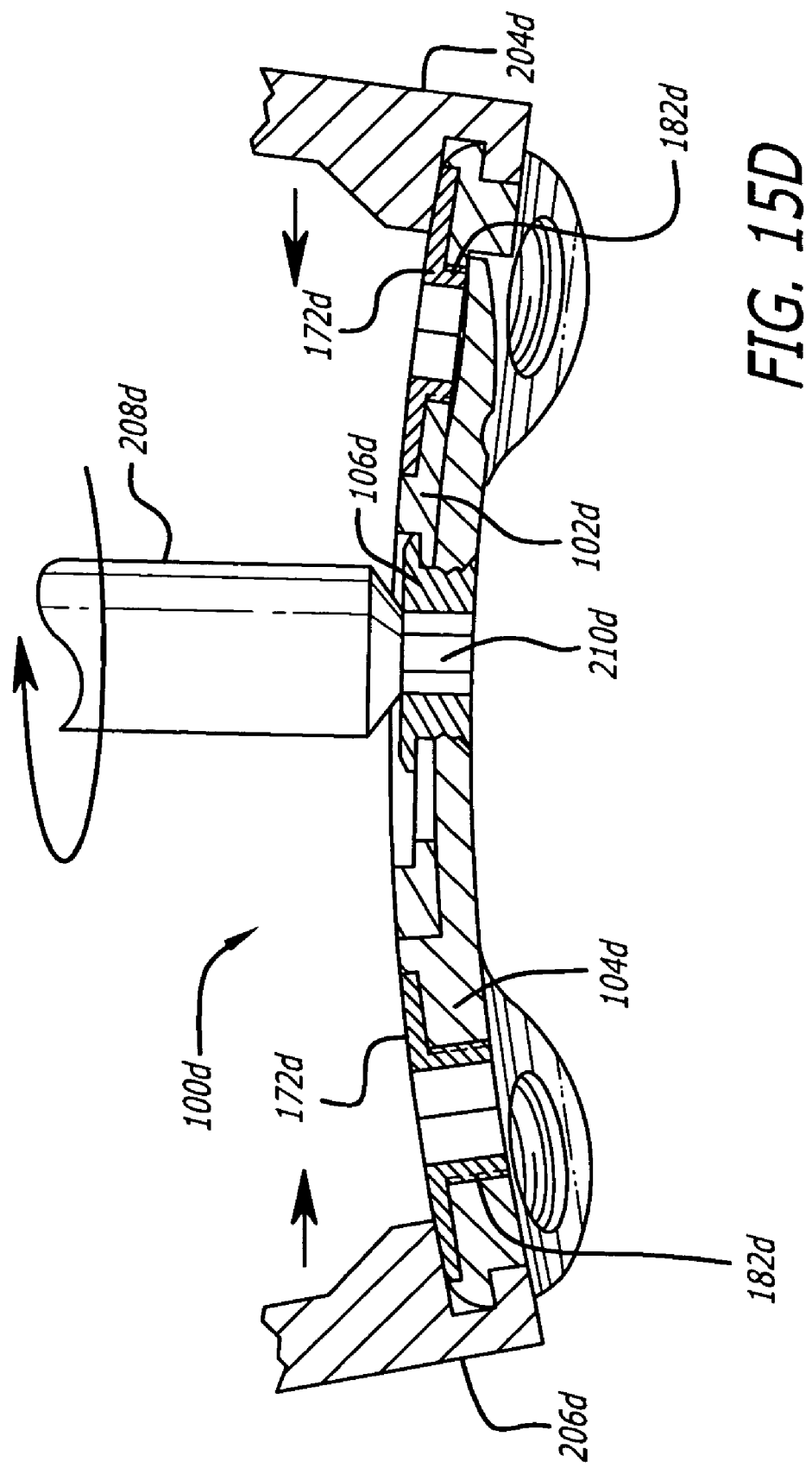
FIG. 15D is a partial cross sectional view along line 15C-15C of FIG. 14C for the plate of FIG. 1D.
Figure 16A:
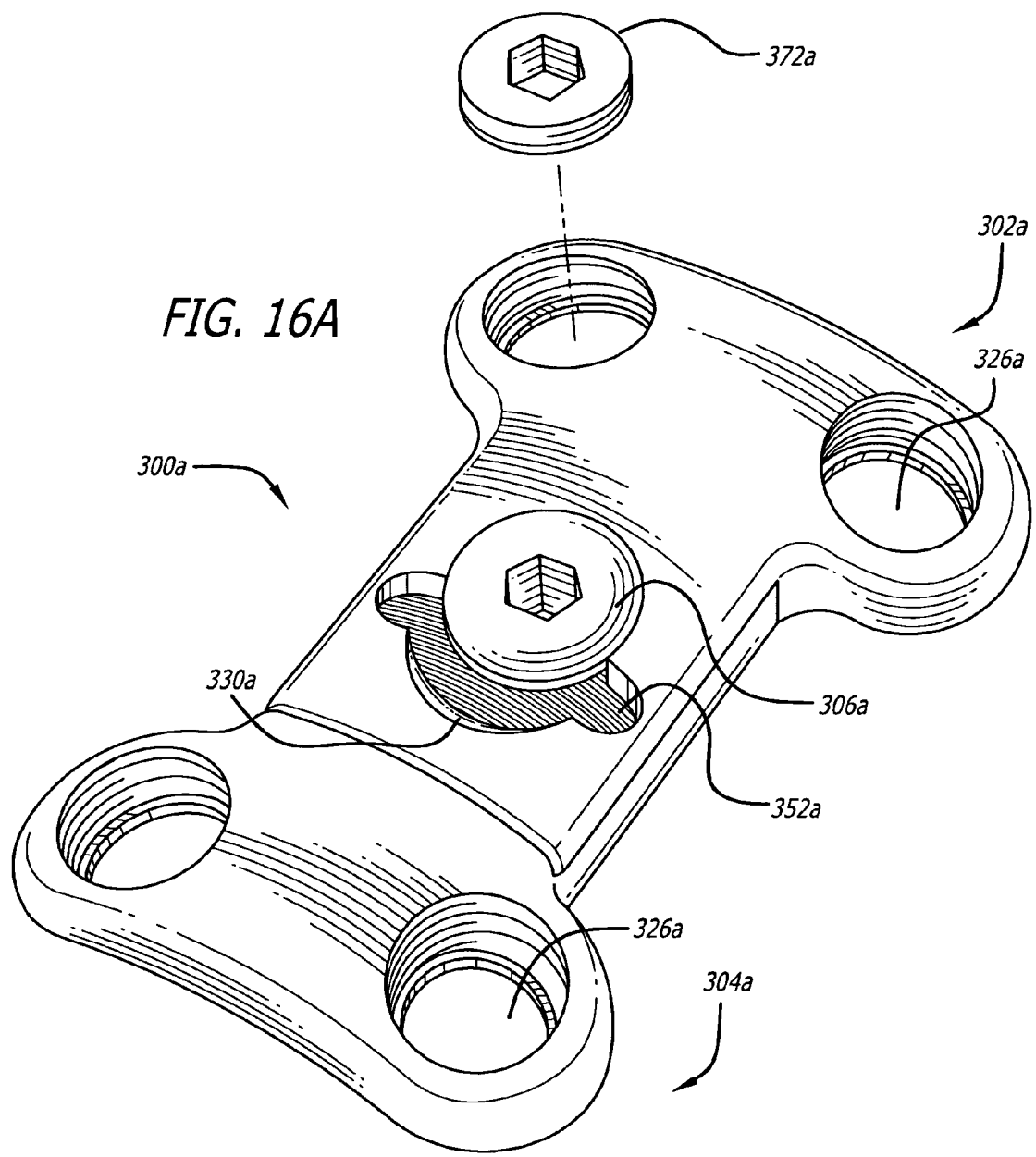
FIG. 16A is a top perspective view of a plate, a fastener, and locking element in accordance with another preferred embodiment of the present invention.
Figure 17C:
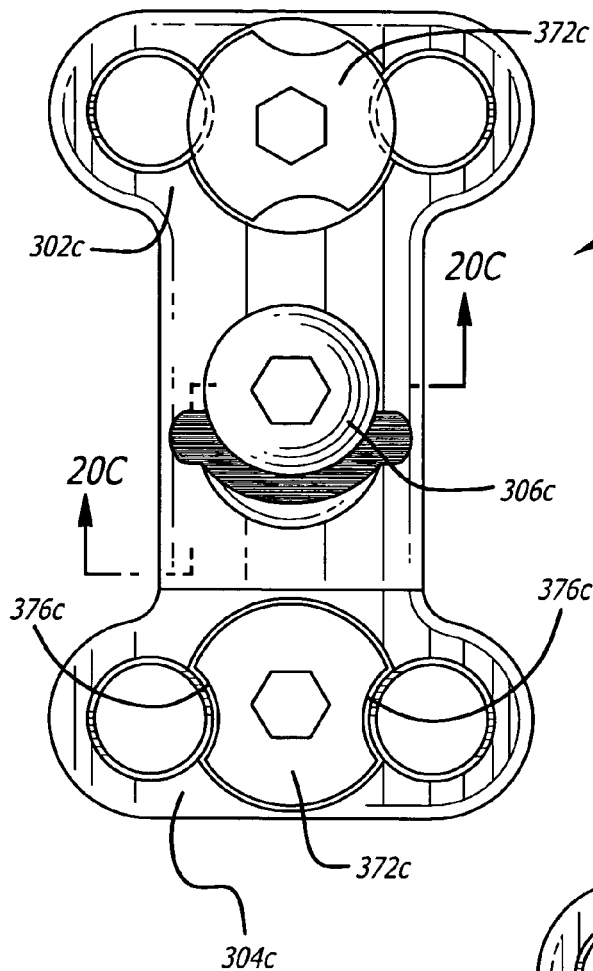
FIG. 17C is a top plan view of the plate, fastener, and locking elements of FIG. 16C.
Figure 18C:
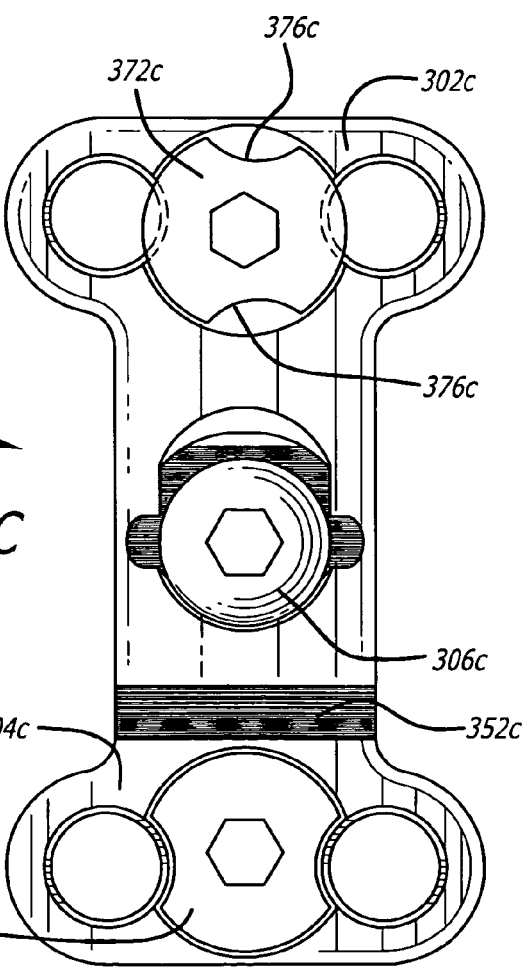
FIG. 18C is a top plan view of the plate of FIG. 16C in an elongated state, fastener, and locking elements.
Figure 19A:
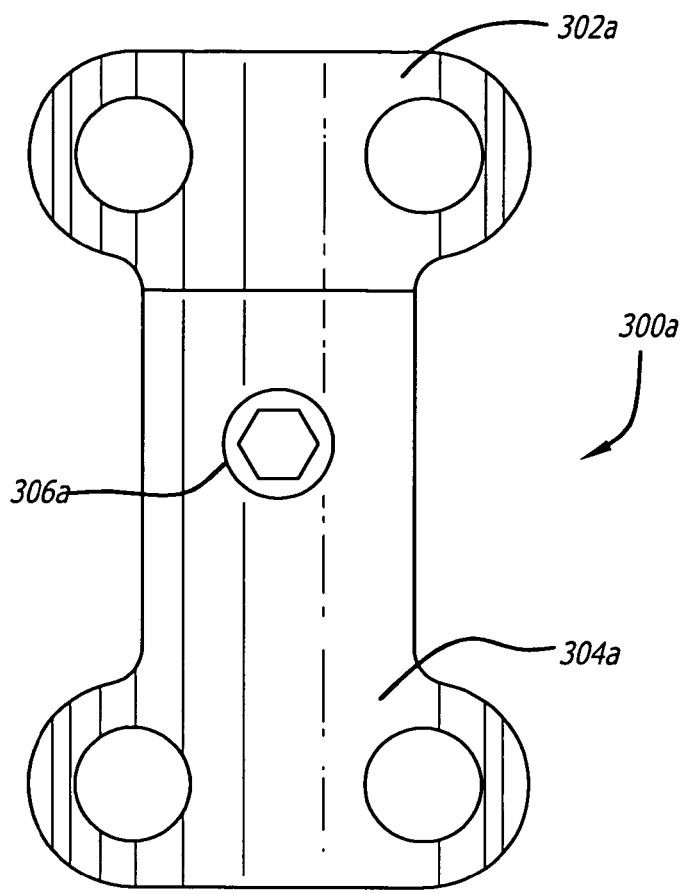
FIG. 19A is a bottom plan view of the plate and fastener of FIG. 16A.

FIGS. 13A, 14A, and 15A show a preferred embodiment of instrumentation $200a$ for compressing and locking plate $100a$. Instrumentation $200a$ has a handle $202a$ with a pair of tongs $204a$, $206a$ in moveable relationship to each. Tongs $204a$, $206a$ are configured to cooperatively engage ends $124a$, $144a$ of first and second segments, $102a$, $104a$, respectively. Instrumentation $200a$ may be used to hold and position plate $100a$ in a desired position at the fusion site during at least a portion of the procedure for installing plate $100a$. Any instrument capable of engaging the plate so as to serve the intended purpose would be within the scope of the instrumentation and method of the present invention. As an example only, methods and instrumentation for installing plates to the cervical spine, including a pilot hole forming punch to create bone screw receiving holes in the vertebral bodies coaxially aligned with the bone screw receiving holes with the plate, are taught and described by Michelson in the '721 patent, incorporated by reference herein. After segments $102a$, $104a$ have been attached to the adjacent vertebral bodies with an appropriate fastening element, such as bone screws, instrument $200a$ can be used to move segments $102a$, $104a$ toward one another to shorten the length of plate $100a$ and create a compressive load across the disc space. After the desired length of plate $100a$ is achieved, an instrument $208a$ having a head $210a$ configured to cooperatively engage fastener $106a$ is used to tighten fastener $106a$ to secure first and second segments $102a$, $104a$ in a desired position. When in a secured position, segments $102a$, $104a$ may maintain a compressive load across the disc space if desired. Head $210a$ of instrument $208a$ may have a hex-shaped configuration.

FIGS. 1B, 2B, 4B, 7B, 8B, and 15B show another preferred embodiment of a cervical plate $100b$ in accordance with the present invention. In this preferred embodiment of the present invention, plate $100b$ may include at least one bone screw lock adapted to lock to the plate only a single bone screw inserted into one of bone screw receiving holes $126b$ such as described above in relation to plate $100a$ and a non-detachable fastener $106b$ configured to couple together first and second segments $102b$, $104b$. Fastener $106b$ is configured to be non-detachably attached to at least one of first and second segments $102b$, $104b$ to couple together two or more plate segments. Fastener $106b$ is non-detachable to prevent non-destructive complete uncoupling of first and second segments $102b$, $104b$ from one another during normal use. As used herein, "non-detachable fastener" is defined as a fastener that once attached is not meant to be removed and then reattached. As shown in FIG. 7B, fastener $106b$, for example, may be embodied in the form of a rivet having a head $108b$, a shaft $112b$, and a base $14b$. By way of example only and not limitation, base $114b$ may be coupled to second segment $104b$ so that it is permanently attached, but is still capable of an element of rotation about its longitudinal axis. Shaft $112b$ of fastener $106b$ preferably has a thread $116b$.

Figure 2B:
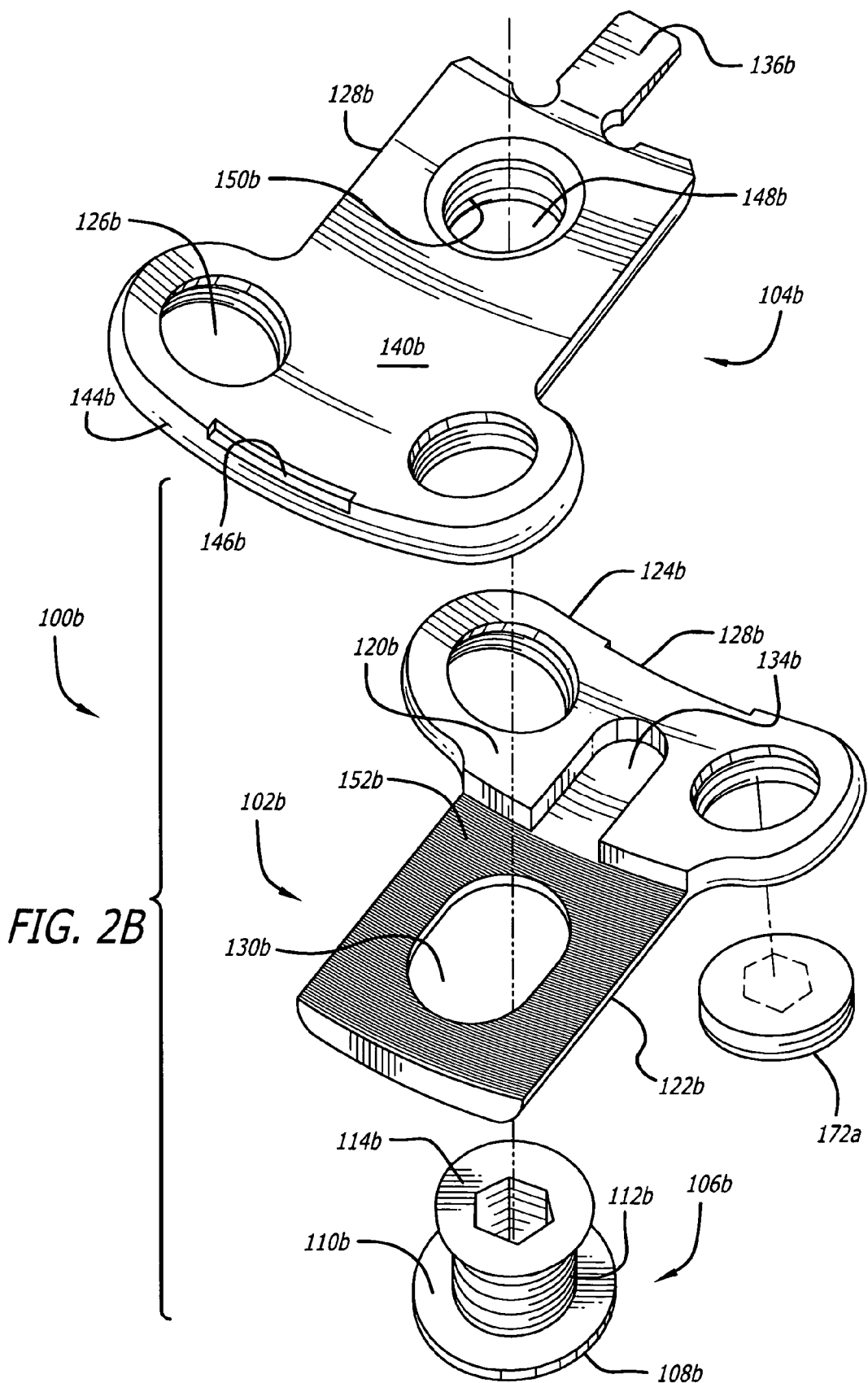
FIG. 2B is an exploded bottom perspective view of the plate, fastener, and locking element of FIG. 1B.
Figure 2C:
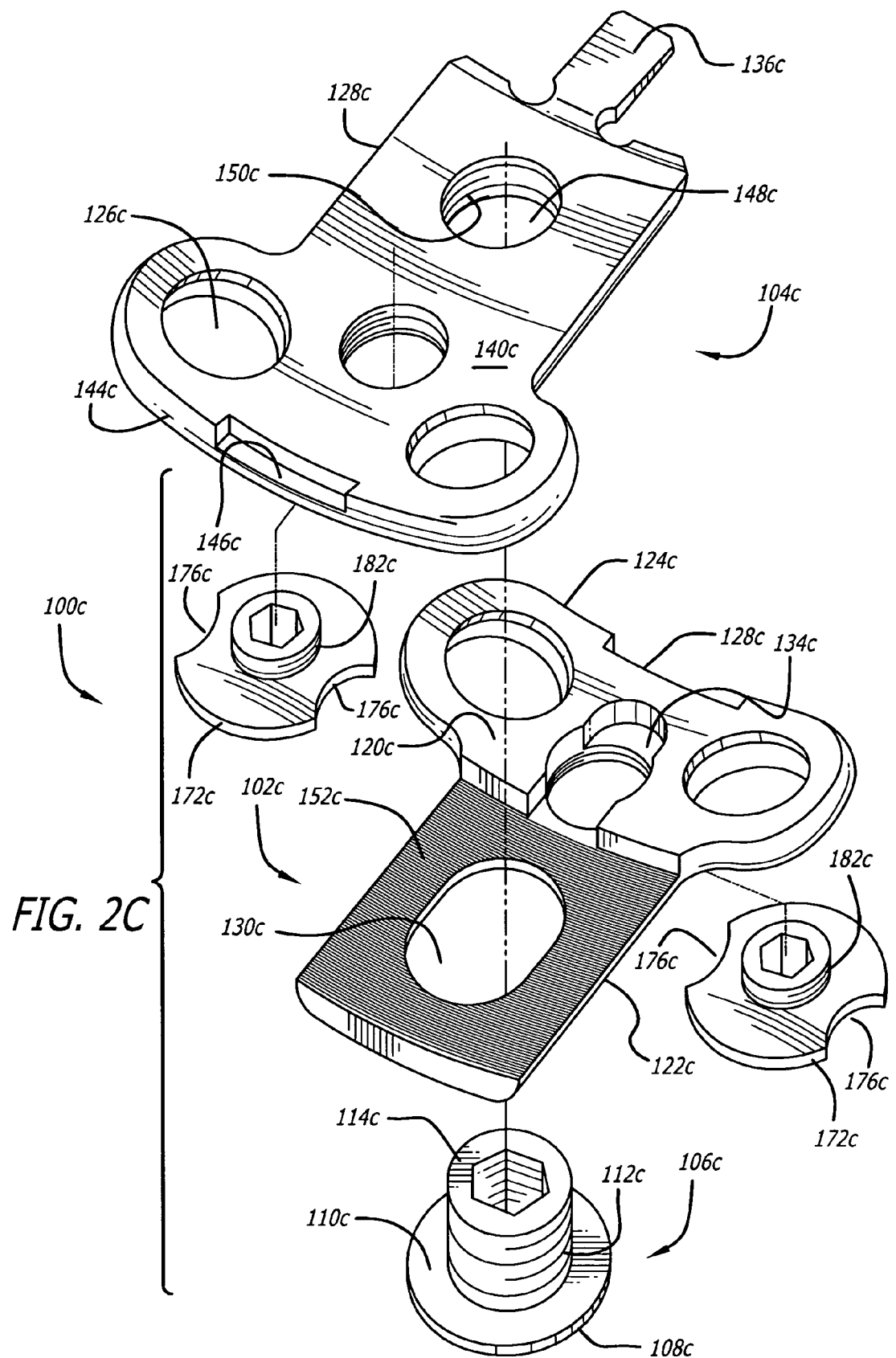
FIG. 2C is an exploded bottom perspective view of the plate, fastener, and locking elements of FIG. 1C.
Figure 2D:
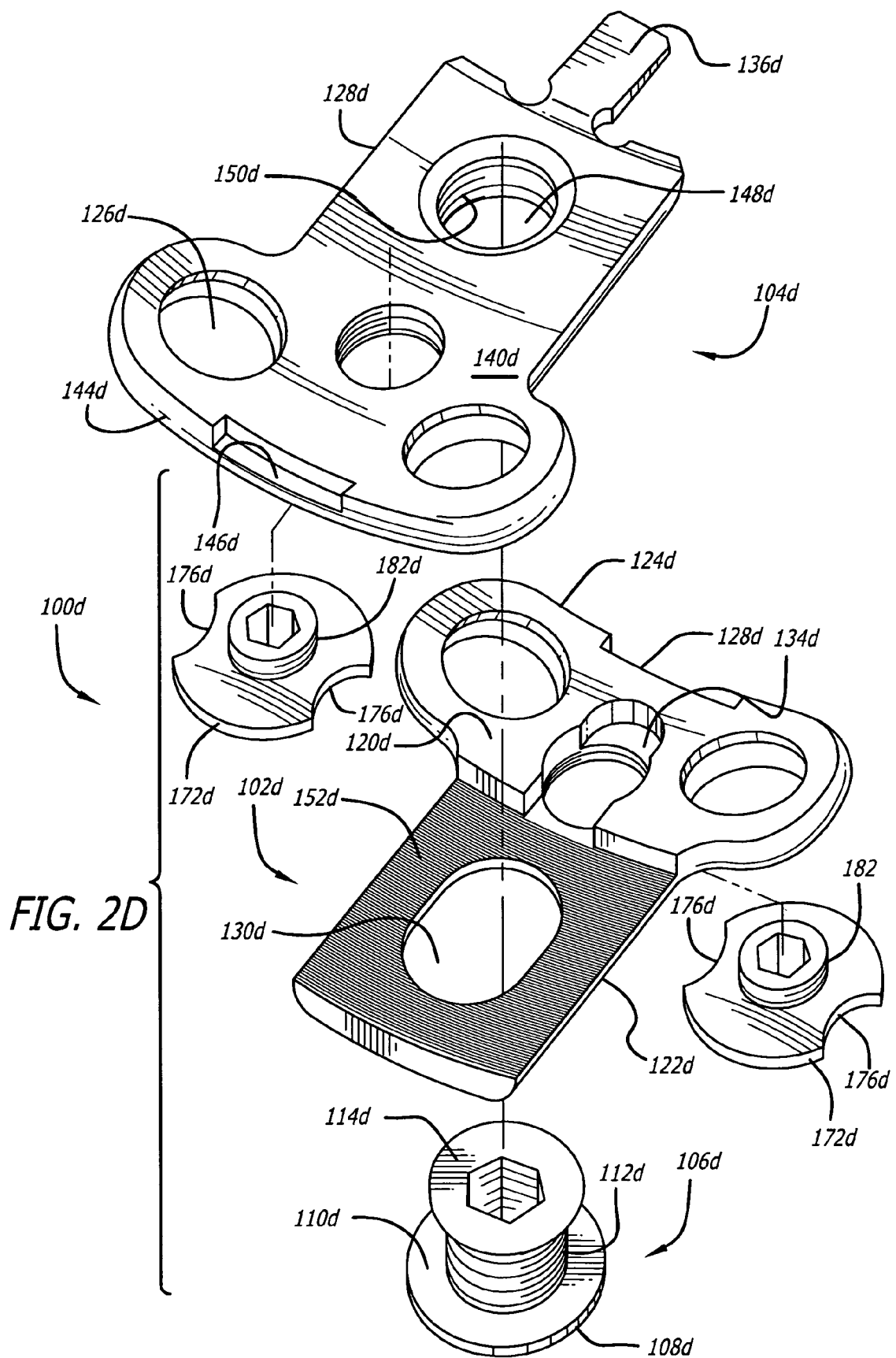
FIG. 2D is an exploded bottom perspective view of the plate, fastener, and locking elements of FIG. 1D.
Figure 4B:
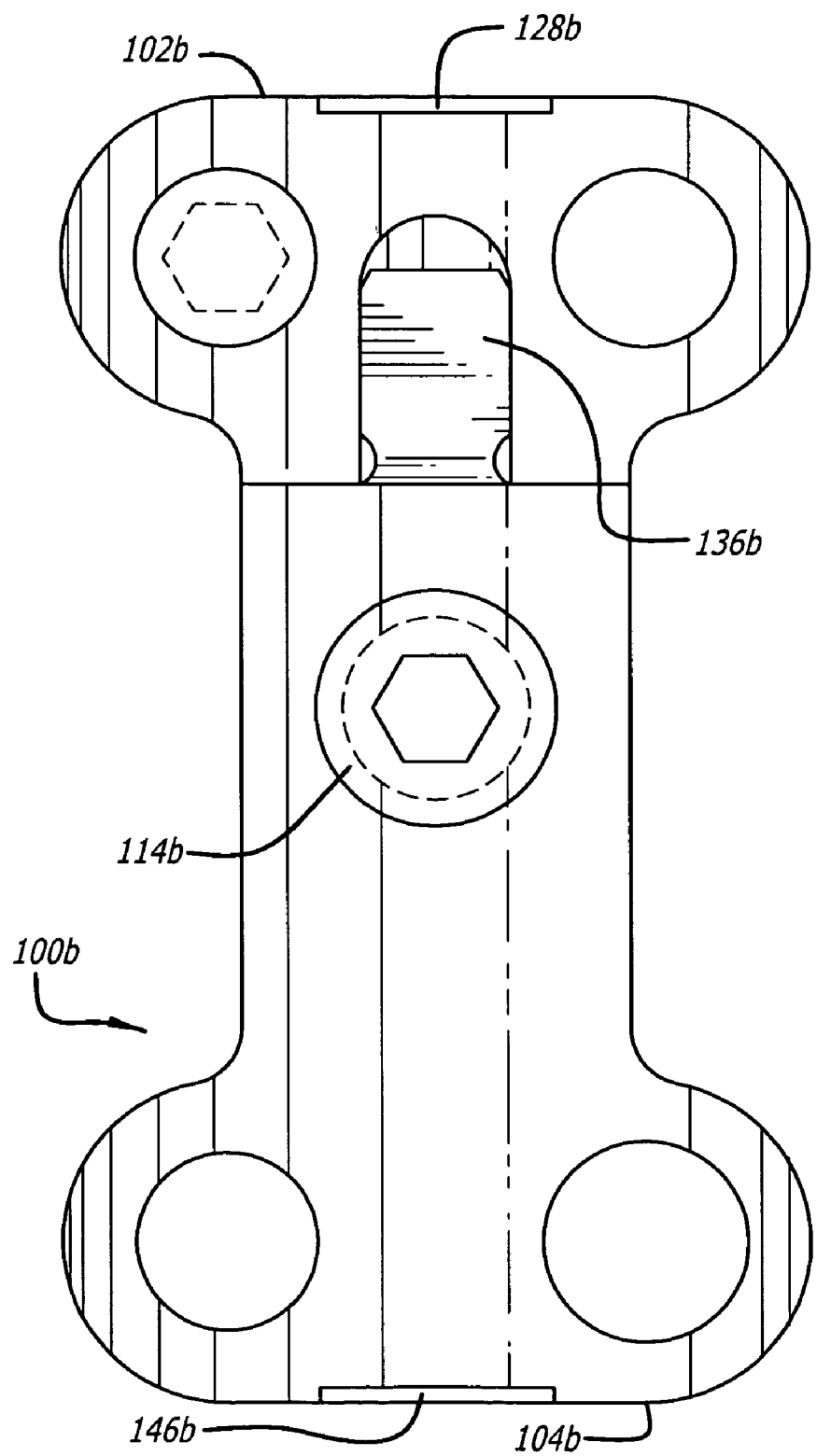
FIG. 4B is a bottom plan view of the plate, fastener, and locking element of FIG. 1B.
Figure 4D:
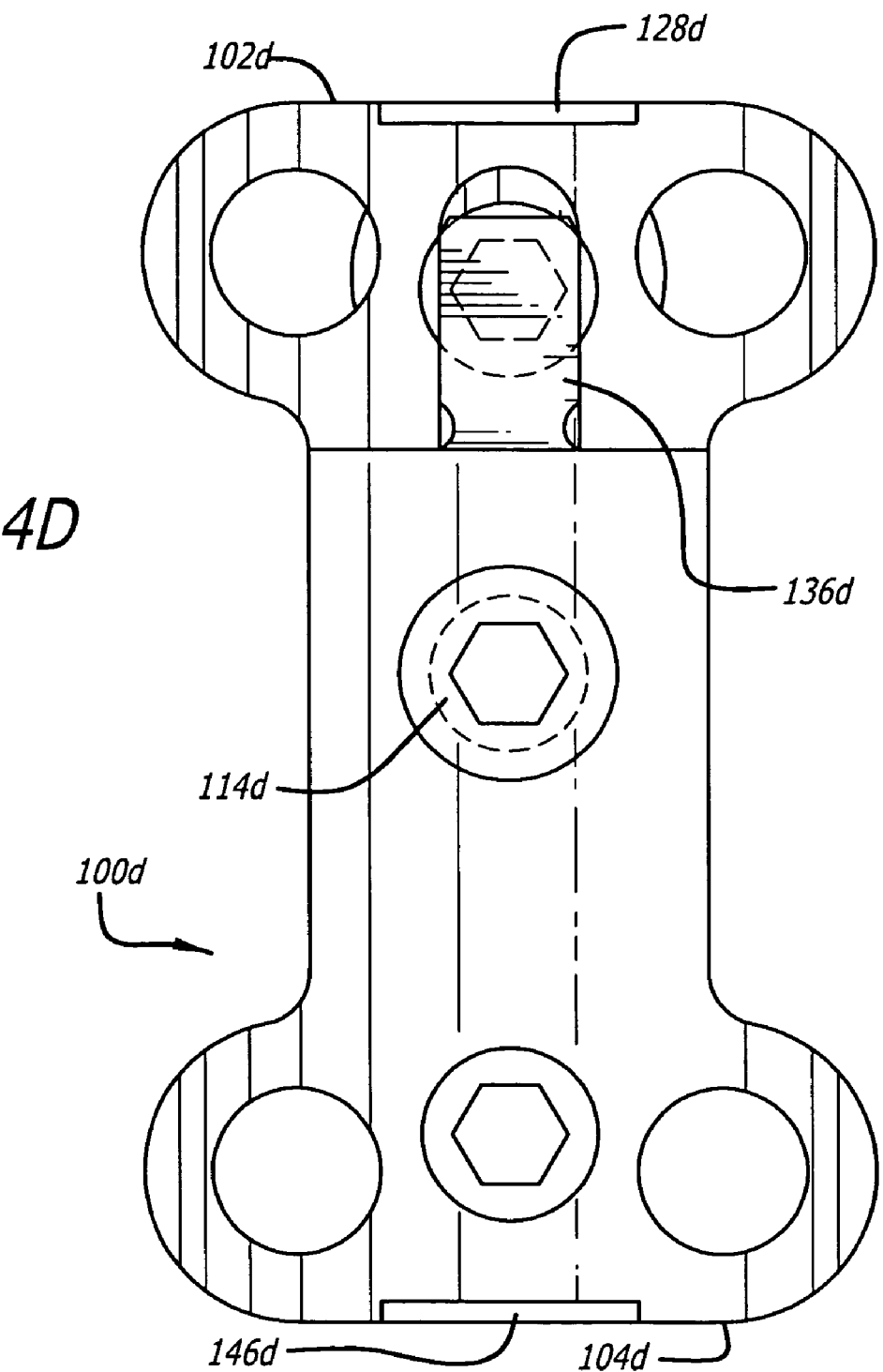
FIG. 4D is a bottom plan view of the plate, fastener, and locking elements of FIG. 1D.
Figure 6C:
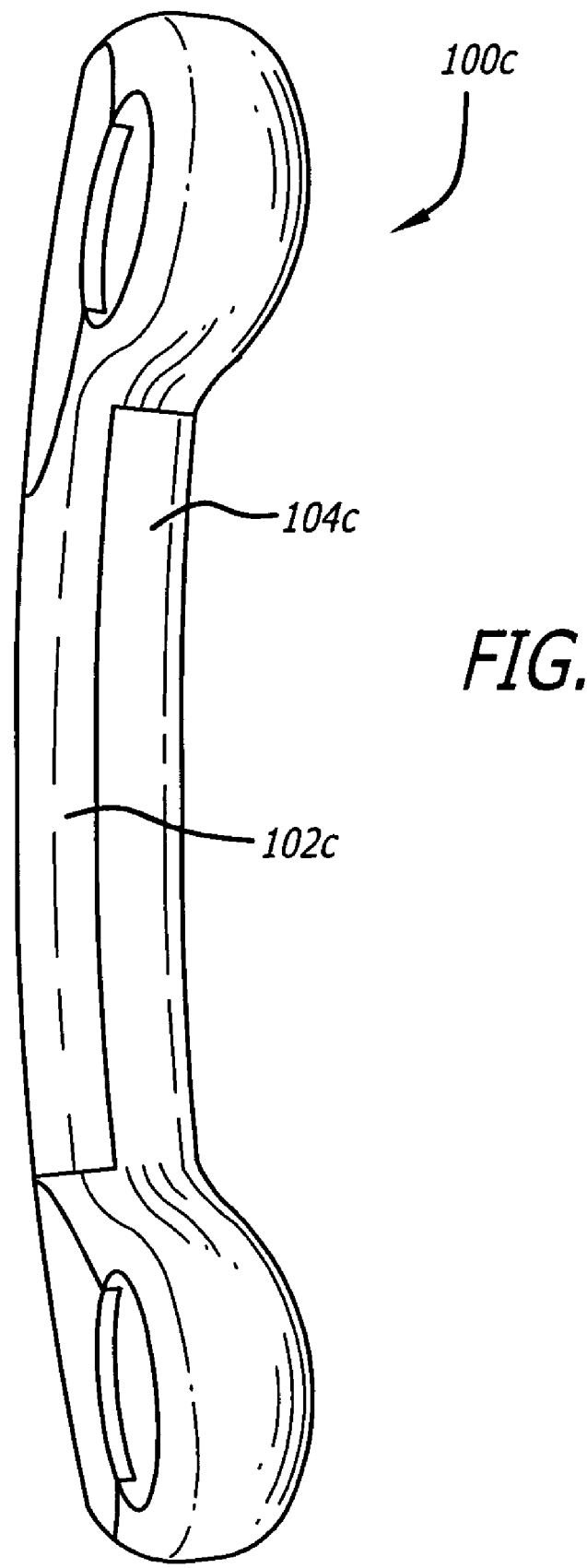
FIG. 6C is a side elevation view of the plates of FIGS. 1C and 1D.

Fastener receiving opening $148b$ of plate $100b$ is configured to permit non-detachable attachment of fastener $106b$ while permitting an element of rotation of fastener $106b$ about its longitudinal axis. For example as shown in FIG. 2B, the bottom portion of fastener receiving opening $148b$ proximate lower surface $140b$ of second segment $104b$ may have a smaller dimension than the maximum dimension of base $114b$ (e.g. flared portion of a rivet) of fastener $106b$ so as to prevent passage of the end portion therethrough. Moreover, the bottom portion of fastener receiving opening $148b$ may be beveled to accommodate base $114b$ (e.g. flared portion) of fastener $106b$ so that it is generally flush or recessed to the bottom surface and preferably does not impede close contact of lower surface $140b$ with the surface of the vertebral bodies. The first and second plate segments may be modular components of various configurations assembled by the manufacturer of the plate and provided to the surgeon in an assembled state. In the assembled state, the plate has a non-detachable fastener that prevents non-destructive complete uncoupling of the first and second segments during normal use.

FIGS. 1C, 2C, 3C, 4C, 6C, 13C, 14C, and 15C show another preferred embodiment of a cervical plate $100c$ in accordance with the present invention. In this preferred embodiment of the present invention, plate $100c$ may include a detachable fastener configured to couple together first and second segments $102c$, $104c$ such as described above in relation to plate $100a$ and a bone screw lock adapted to lock at least two bone screws inserted in bone screw receiving holes $126c$. Bone screw locks $172c$ are coupled to plate $100c$ and may be removable or may be non-detachably attached to plate $100c$. Bone screw locks $172c$ may be coupled to plate $100c$ prior to the insertion of the bone screws into bone screw receiving holes $126c$. Alternatively, the bone screw locks may be coupled to the plate after the insertion of the bone screws into the bone screw receiving holes.

As shown in FIGS. 1C, 2C, 3C, 4C, 14C, and 15C, by way of example only and not limitation, bone screw lock 172c may have a tool engagement portion 174c adapted to cooperatively engage an instrument used for coupling bone screw lock 172c to plate 100c and at least one cutout 176c. Each cutout 176c is oriented so as to permit introduction of a bone screw into an adjacent bone screw receiving hole when bone screw lock 172c is coupled to plate 100c and in the appropriate orientation. It is appreciated that other configurations of the bone screw lock are possible so as to permit introduction of a bone screw into a bone screw receiving hole adjacent to the bone screw lock without interference from the bone screw lock.

Plate 100c may have an opening 178c for receiving at least a portion of locking element 172c and may, but need not, include a recess 180c for receiving at least a portion of locking element 172c therein. Bone screw lock 172c may have a stem 182c configured to fit at least in part within opening 178c in plate 100c. Stem 182c and opening 178c may be threaded to threadably engage bone screw lock 172c to plate 100c. Alternatively, at least a portion of the interior perimeter of recess 180c and at least a portion of the perimeter of the bone screw lock may be threaded to threadably engage the bone screw lock to the plate.

In a preferred embodiment, bone screw locks 172c are configured to move from an initial position, that permits the insertion of bone screws into the bone screw receiving holes, to a final position that is adapted to extend over at least a portion of at least two of the bone screws to retain the bone screws to the plate. The bone screw lock may be adapted to be rotated from the initial position to the final position, and preferably, less than a full rotation of the bone screw lock rotates the bone screw lock from the initial position to the final position. In a preferred embodiment, the bone screw lock in the final position covers at least a portion of at least two of the bone screw receiving holes.

In another preferred embodiment, at least a portion of the bone screw lock slides from the initial position to the final position. The bone screw lock can slide over at least a portion of at least two of the bone screw receiving holes and/or slide over at least a portion of at least two bone screws in the bone screw receiving holes. The bone screw lock may be in the form of a screw, a rivet, a cap, a cover, or have any other configuration suitable for its intended purpose. The bone screw lock may have a head that is at least in part circular.

Where it is desired to lock more than one bone screw to the plate with one bone screw lock, any lock suitable for locking a plurality of bone screws to an anterior cervical plate known to those of ordinary skill in the art may be utilized, including but not limited to, the bone screw locks taught by Michelson in U.S. Pat. No. 6,193,721 (the '721 patent), incorporated by reference herein.

FIGS. 1D, 2D, 4D, and 15D show another preferred embodiment of a cervical plate 100d in accordance with the present invention. In this preferred embodiment of the present invention, plate 100d may include a non-detachable fastener configured to couple together first and second segments 102d, 104d such as described above in relation to plate 100b and a bone screw lock adapted to lock at least two bone screws inserted into bone screw receiving holes 126d such as described above in relation to plate 100c.

FIGS. 16A, 17A, 18A, 19A, 20A, 21A, and 22A show another preferred embodiment of a cervical plate 300a having an internal compression mechanism in accordance with the present invention. Plate 300a is similar to plate 100a except that fastener receiving opening 330a and fastener 306a function as part of a mechanism to move first and second segments 302a, 304a relative to one another to change the length of plate 300a to generate a compressive load across the disc space between two adjacent vertebral bodies to be fused. Fastener receiving opening 330a includes instrument pin receiving recesses $362a_1$ and $362a_2$ for cooperating with the pin of an instrument 400a (described below) for moving first and second segments 302a, 304a relative to one another. In addition, instead of a tab 136a, plate 300a has pins 358a and tracks 360a to maintain first and second segments 302a, 304a aligned along the longitudinal axis of plate 300a. Bone screw lock 372a is adapted to lock to plate 300a at least two bone screws inserted in bone screw receiving holes 326a.

Figure 20A:
FIG. 20A is a partial cross sectional view along line 20A-20A of the plate of FIG. 17A.
Figure 19B:
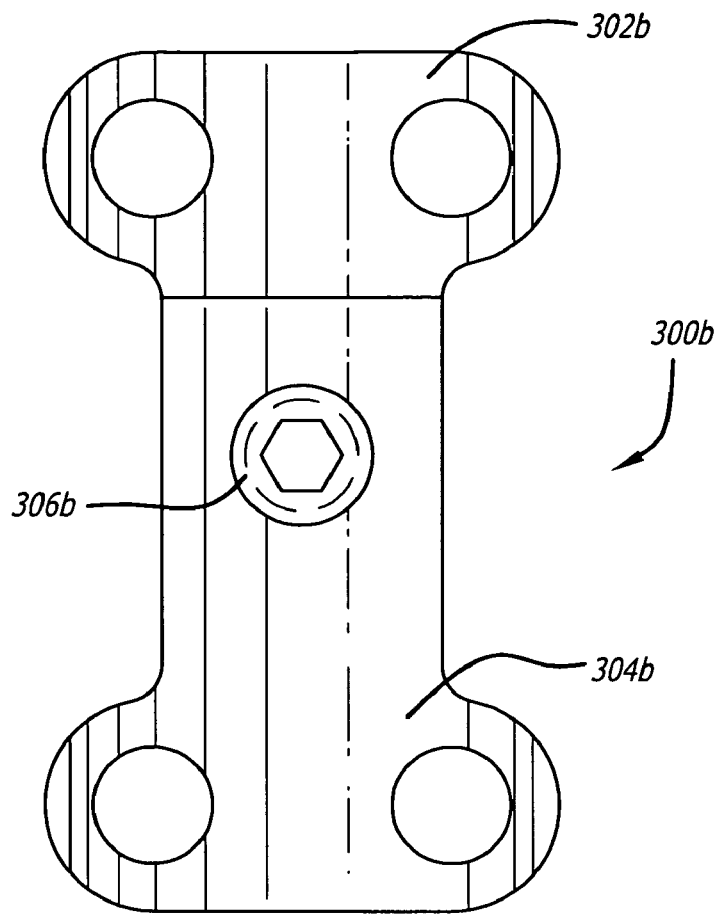
FIG. 19B is a bottom plan view of another preferred embodiment of the plate and fastener of FIG. 16A.
Figure 20B:
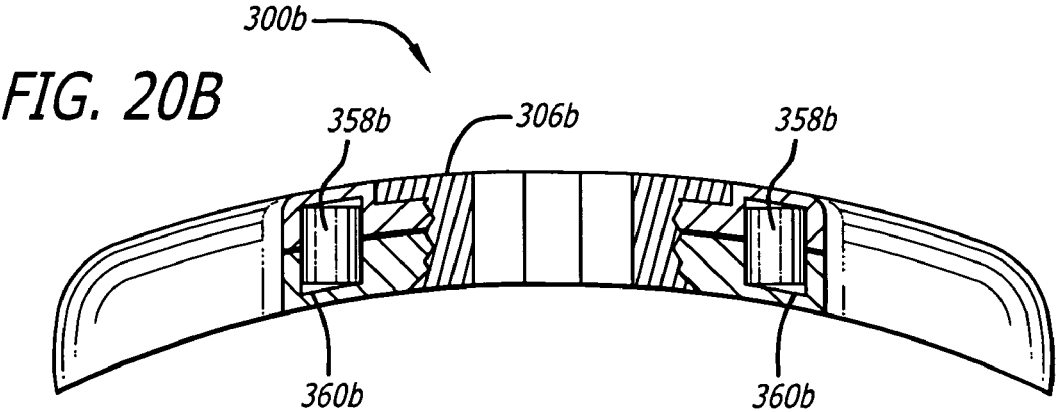
FIG. 20B is a partial cross sectional view along line 20A-20A of FIG. 17A of a plate and fastener in accordance with another preferred embodiment of the present invention.
Figure 19C:
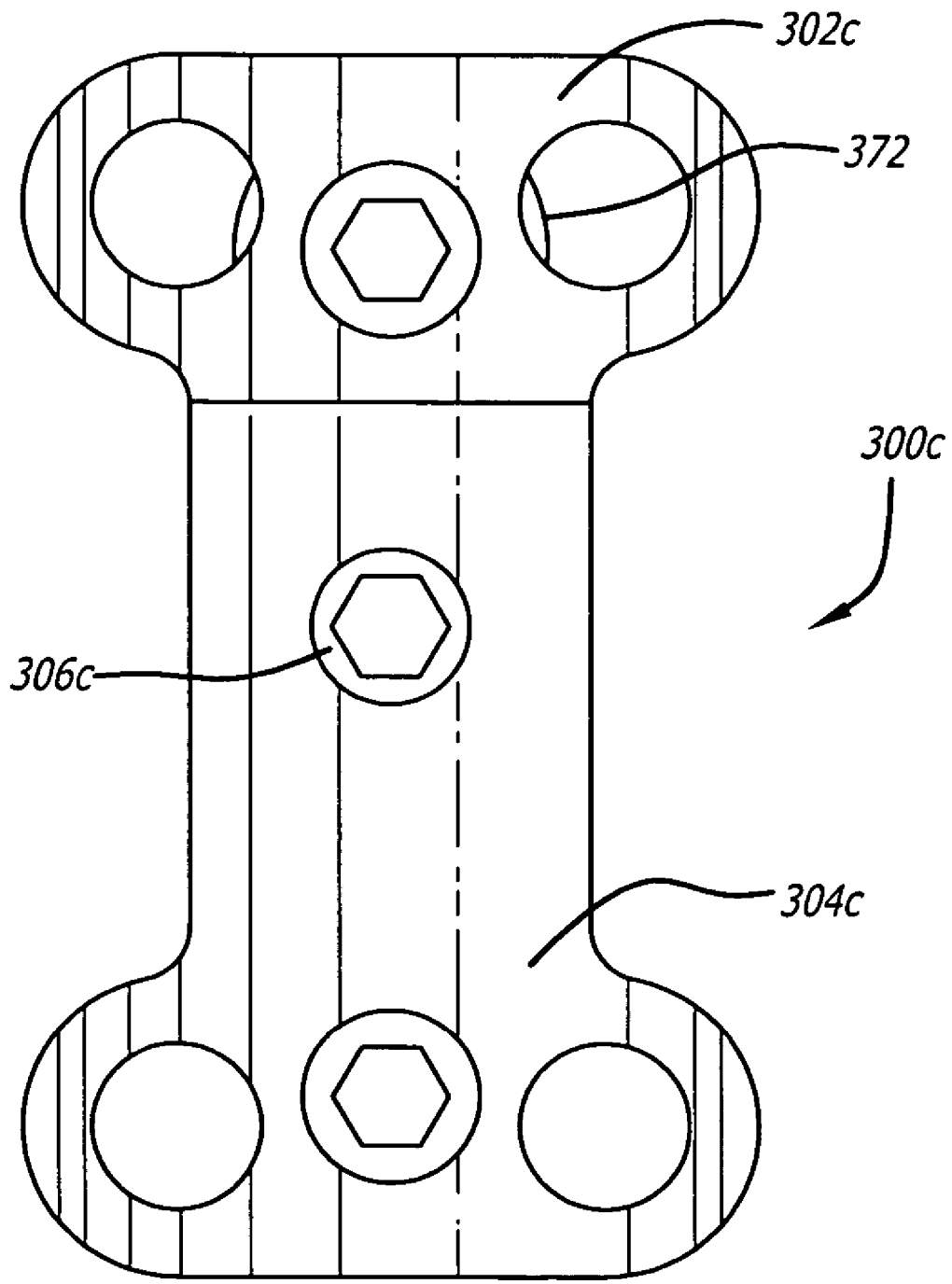
FIG. 19C is a bottom plan view of the plate and fastener of FIG. 16C.
Figure 19D:
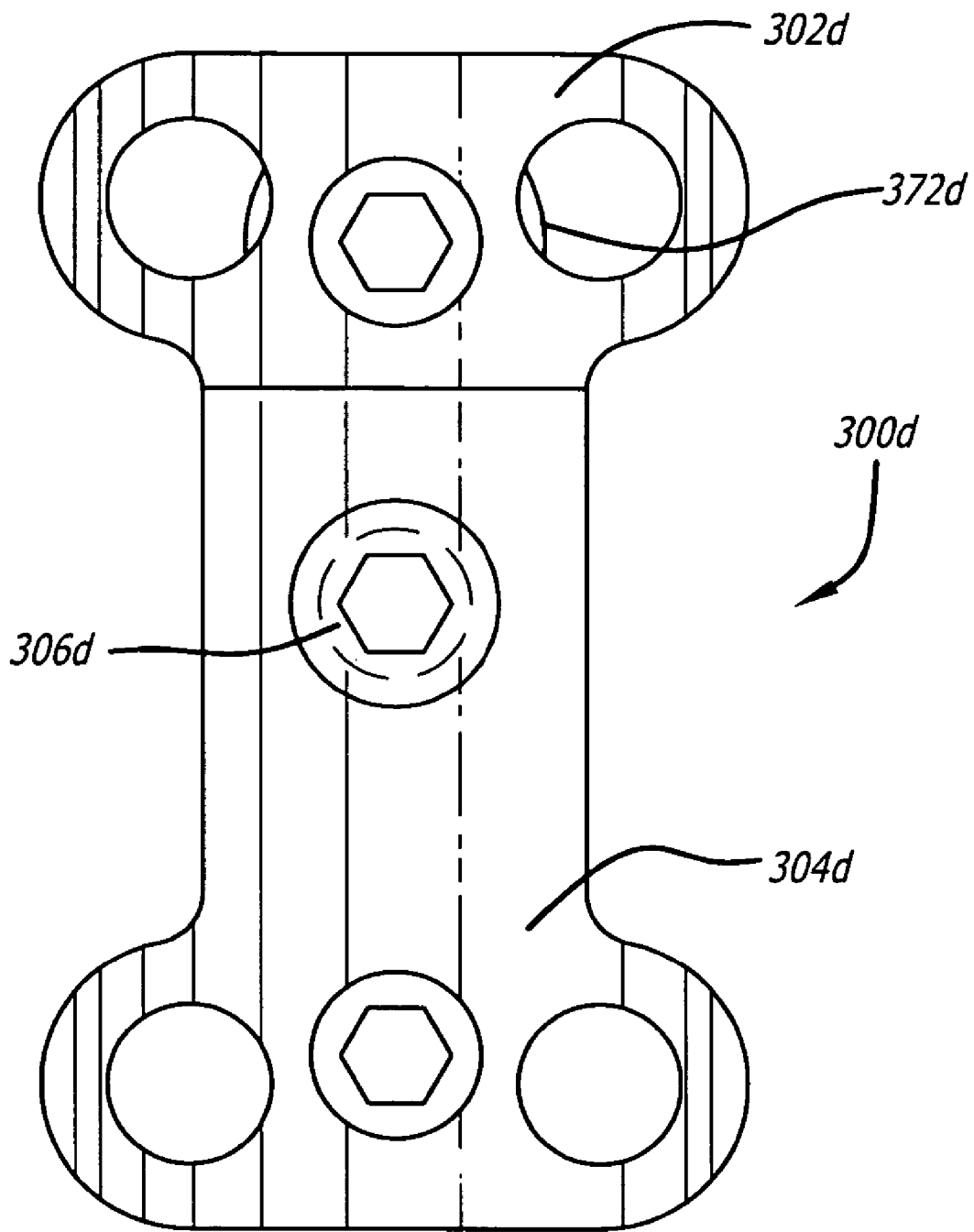
FIG. 19D is a bottom plan view of another preferred embodiment of the plate and fastener of FIG. 16C.
Figure 21D:
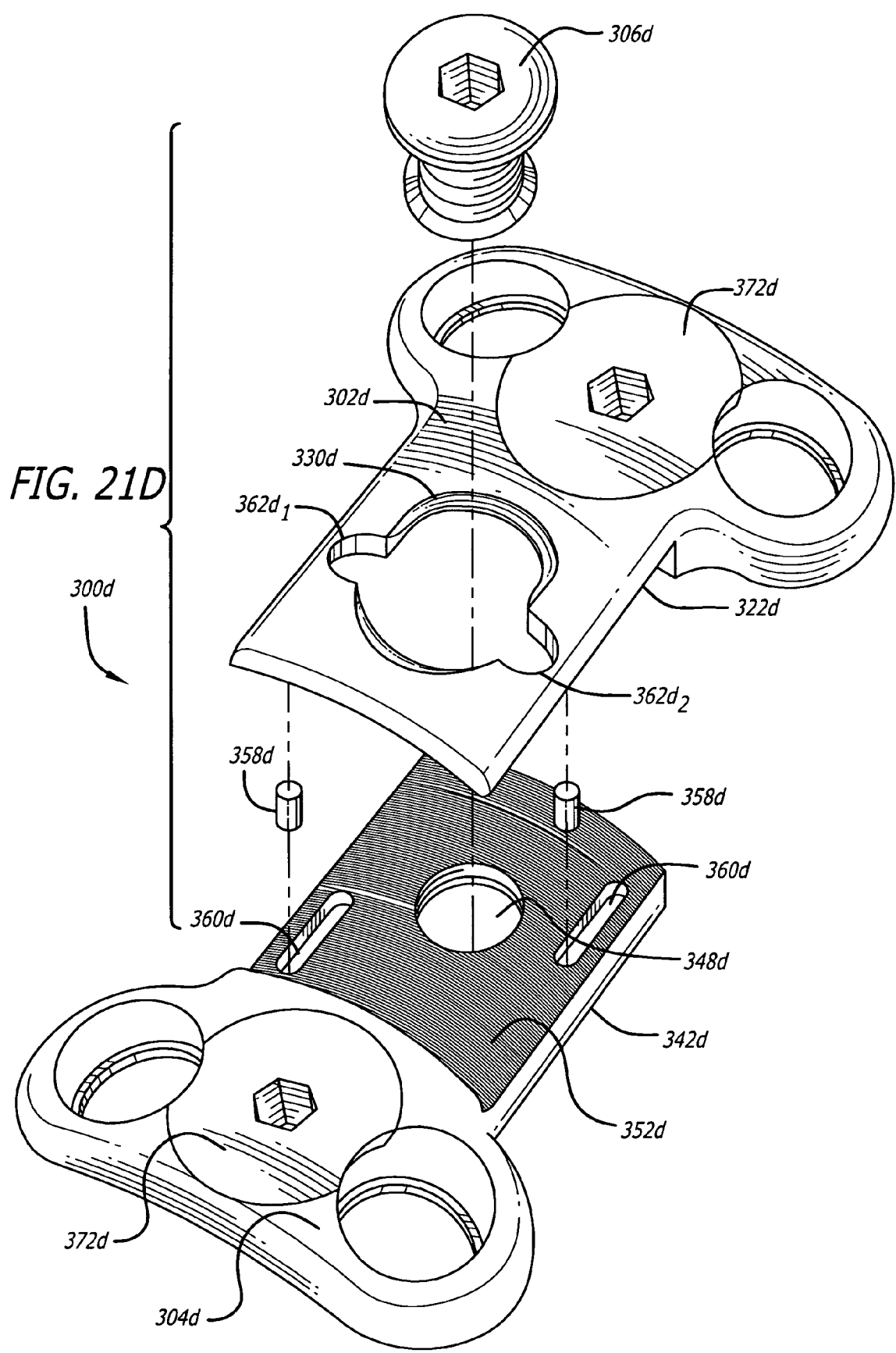
FIG. 21D is an exploded top perspective view of the plate, fastener, and locking elements of FIG. 16C in accordance with another preferred embodiment of the present invention.
Figure 22A:
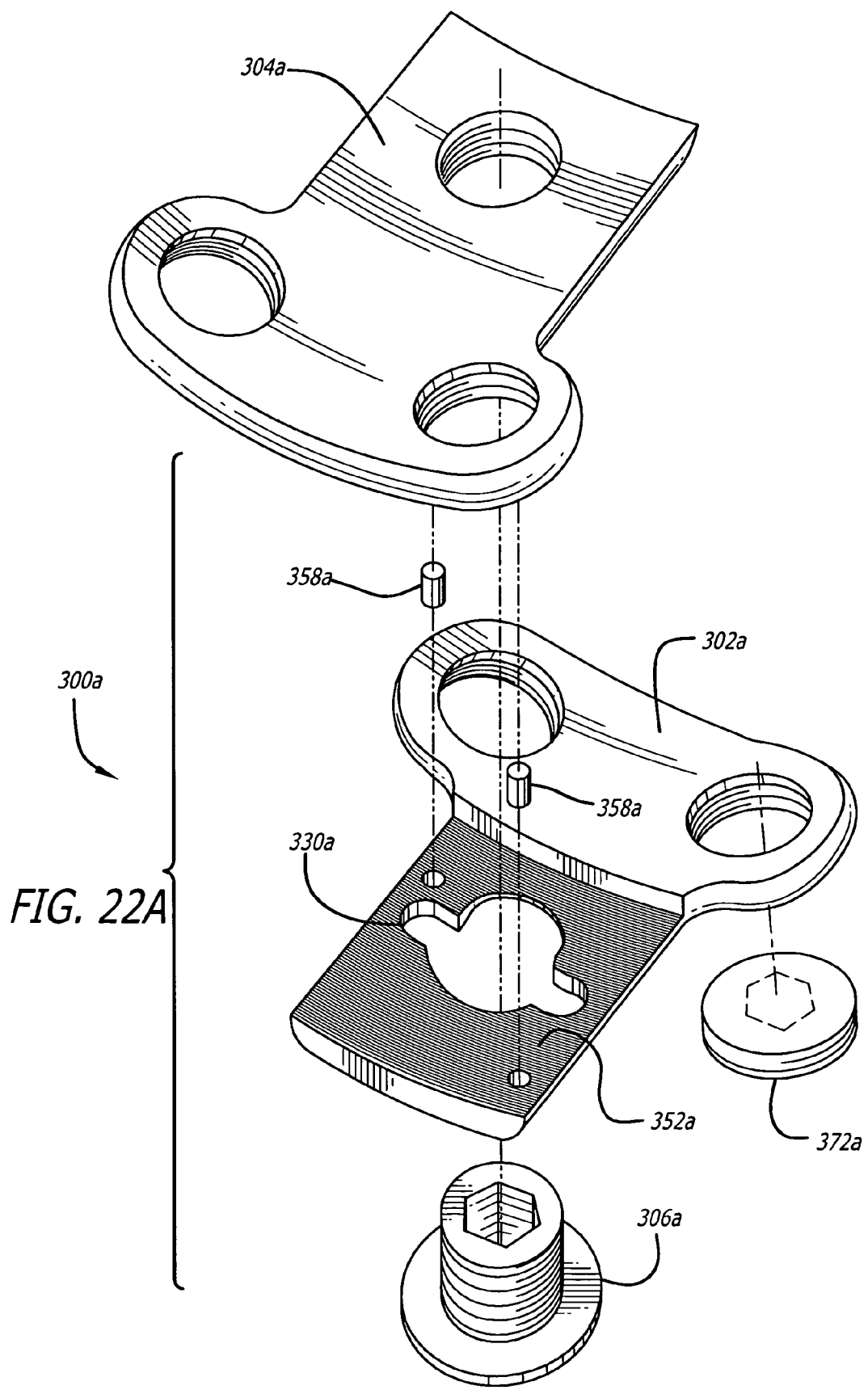
FIG. 22A is an exploded bottom perspective view of the plate, fastener, and locking element of FIG. 16A.
Figure 22B:
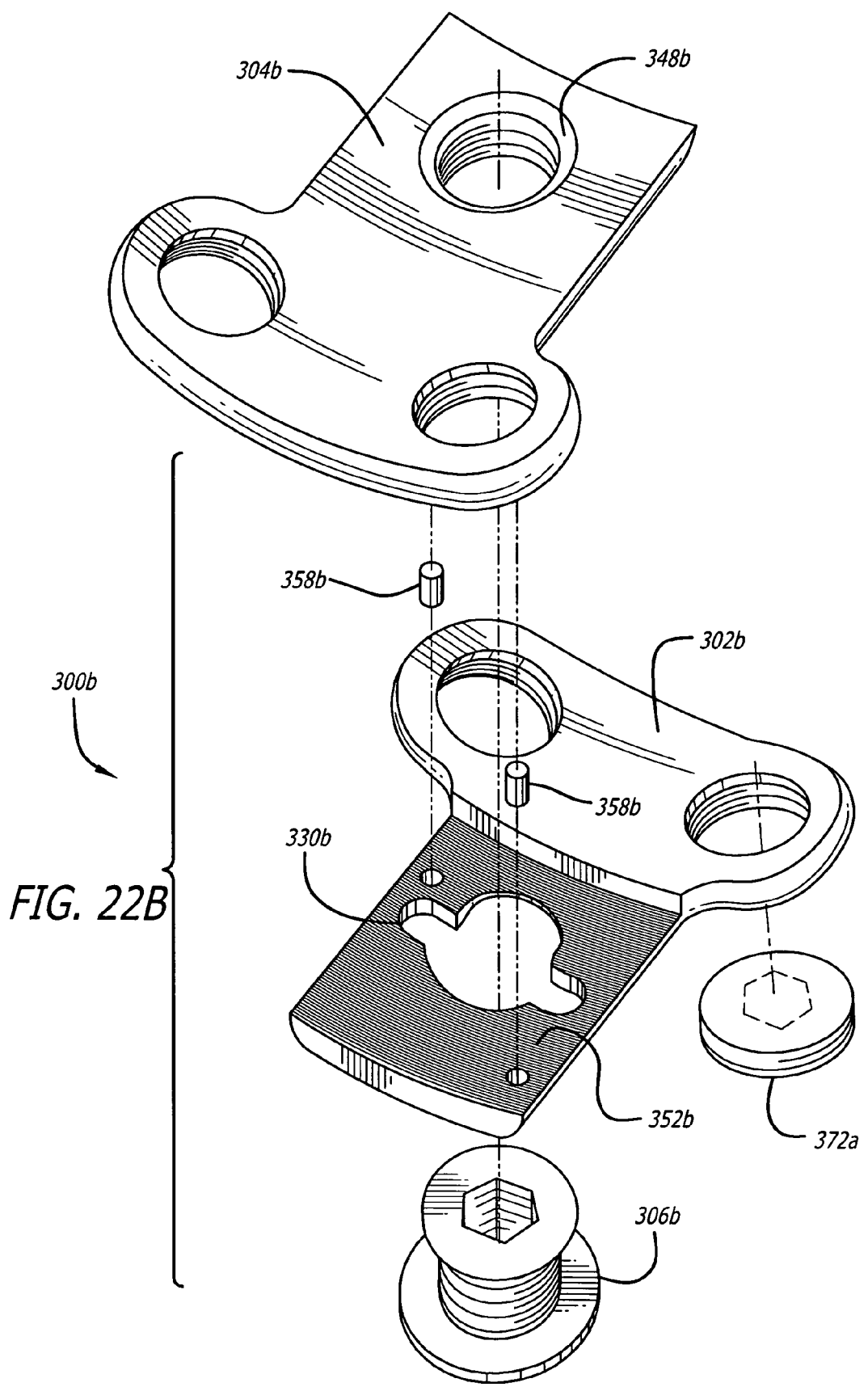
FIG. 22B is an exploded bottom perspective view of the plate, fastener, and locking element of FIG. 21B.
Figure 22C:
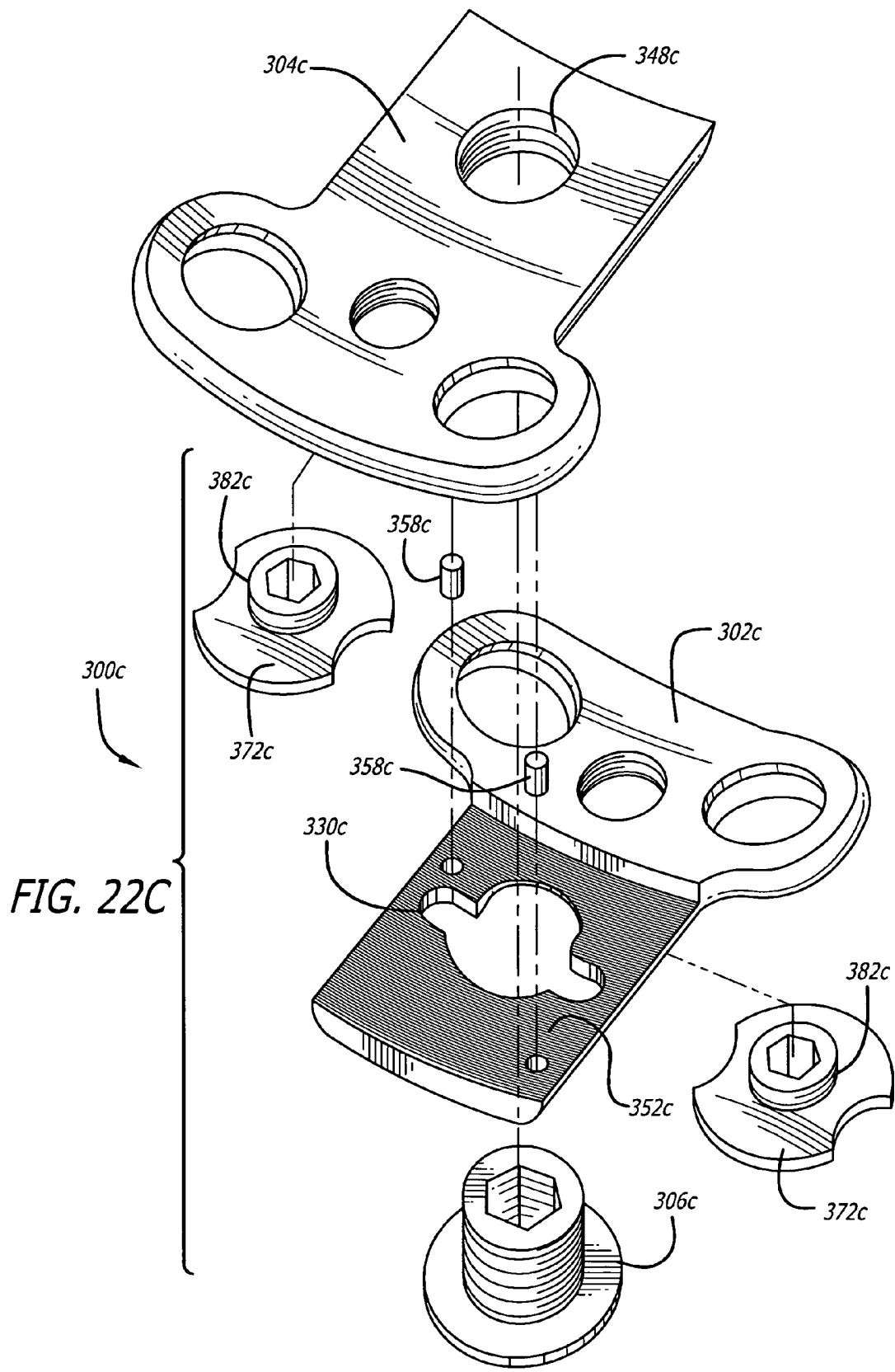
FIG. 22C is an exploded bottom perspective view of the plate, fastener, and locking elements of FIG. 16C.
Figure 22D:
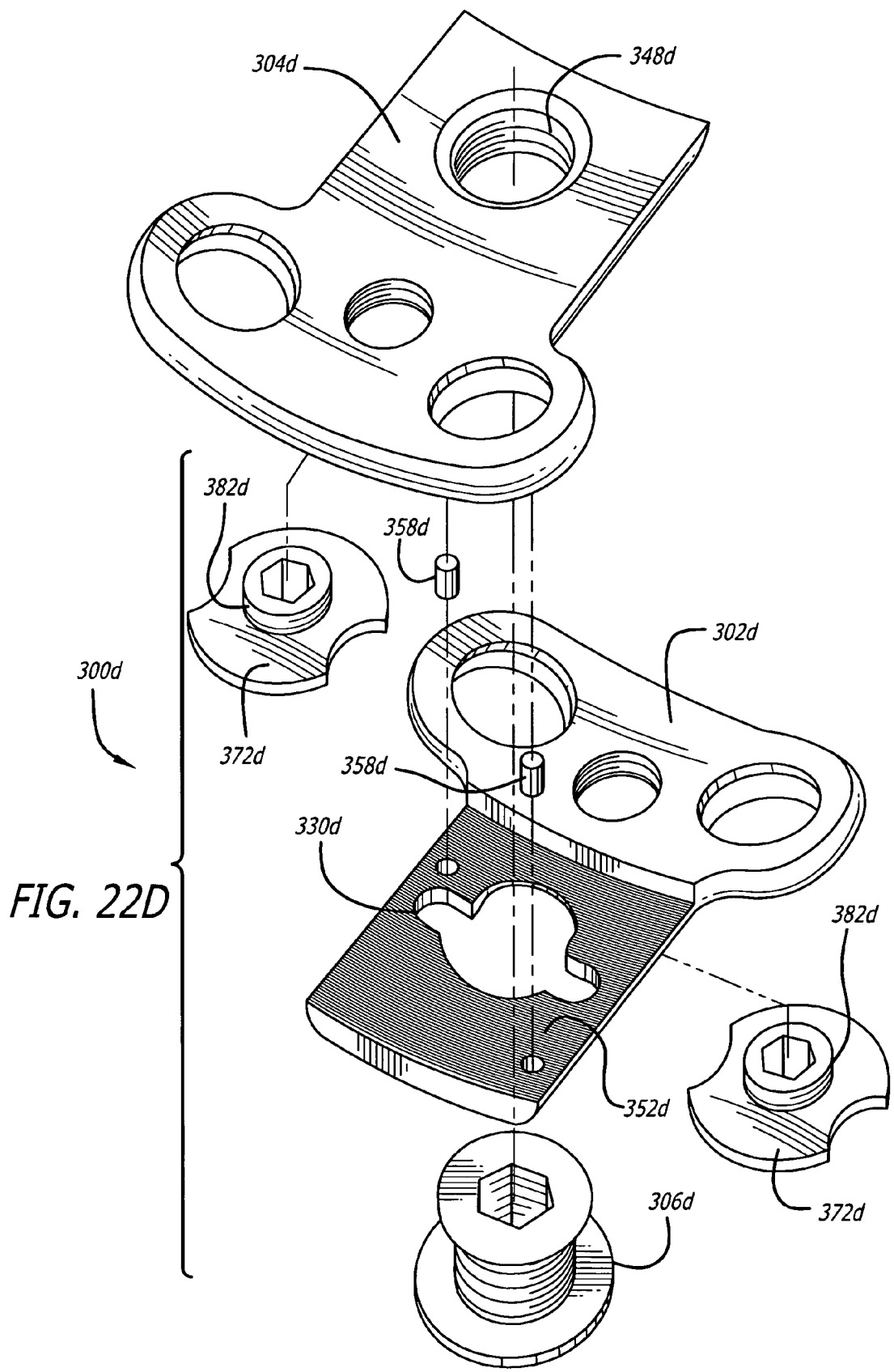
FIG. 22D is an exploded bottom perspective view of the plate, fastener, and locking elements of FIG. 21D.
Figure 24D:
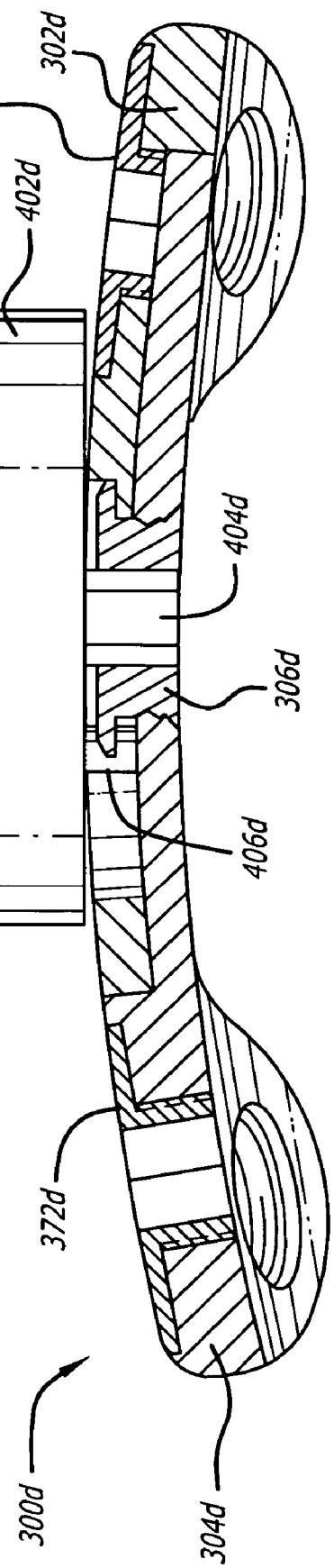
FIG. 24D is an enlarged cross sectional view of another preferred embodiment of the plate of FIG. 16C with the instrument of FIG. 23C engaging the fastener and positioned within the plate.

As shown in FIGS. 20A, 21A, and 22A, first segment 302a preferably has two pins 358a depending therefrom for engagement in corresponding tracks 360a in second segment 304a. Pins 358a slideably engage tracks 360a, respectively, and travel therein when first and second segments 302a, 304a are moved relative to one another. Tracks 360a are staggered along the length of medial portion 342a and pins 358a are staggered along the length of medial portion 322a to maintain first and second segments 302a, 304a aligned along the longitudinal axis of plate 300a. It is appreciated that any plate configuration to achieve the intended purpose of maintaining first and second segments 302a, 304a aligned along the longitudinal axis of the plate would be within the scope of the present invention.

Figure 25A:
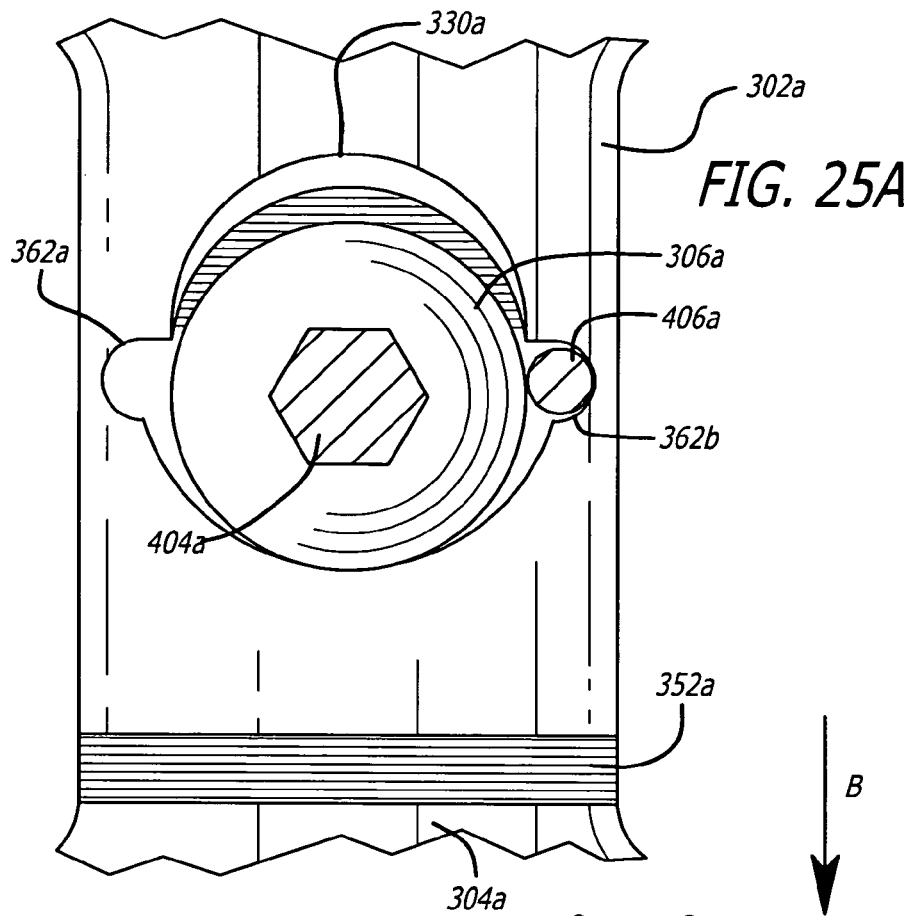
FIG. 25A is a fragmentary top plan view of one of the plates of FIGS. 16A and 16C in an elongated state with the instrument of FIGS. 23A and 23C shown in cross section engaging the fastener and positioned within the plate.
Figure 26A:
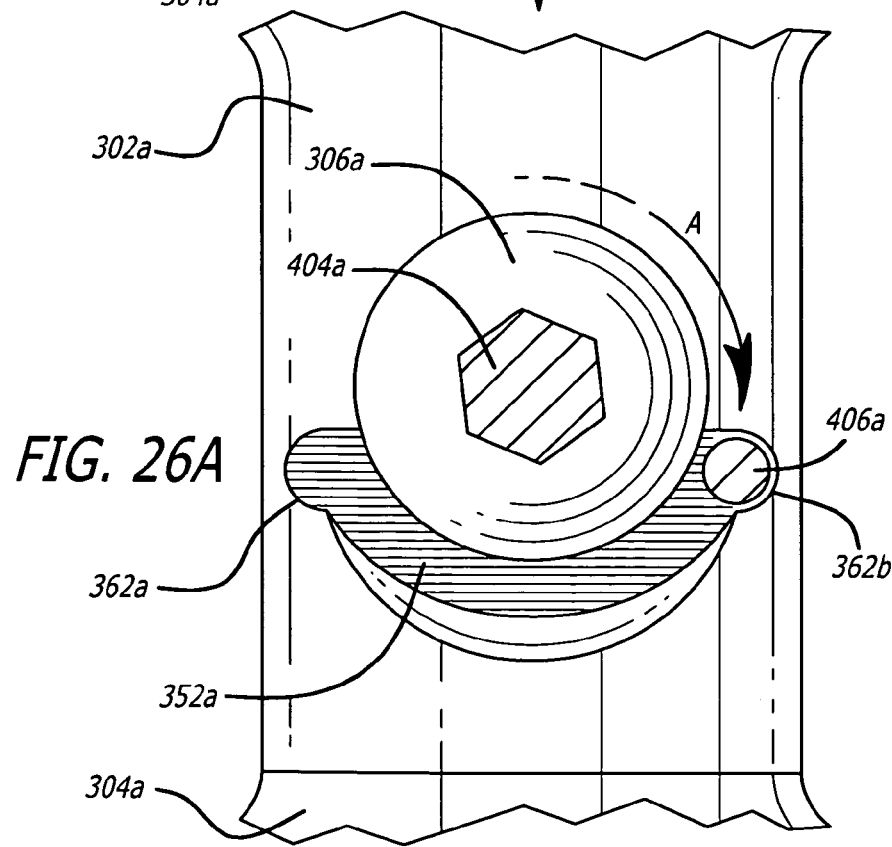
FIG. 26A is a fragmentary top plan view of one of the plates of FIGS. 16A and 16C in a compressed state with the instrument of FIGS. 23A and 23C shown in cross section engaging the fastener and positioned within the plate to rotate the fastener in the direction of the arrow to compress the plate.

FIGS. 23A, 24A, 25A, and 26A show a preferred embodiment of instrumentation 400a used for compressing and locking plate 300a. Instrumentation 400a has a working end 402a configured to cooperatively engage fastener receiving opening 330a and fastener 306a. After segments 302a, 304a have been attached to the adjacent vertebral bodies with an appropriate fastening element, such as bone screws, instrument 400a can be used to move segments 302a, 304a toward one another to shorten the length of plate 300a, create a compressive load across the disc space, and concurrently tighten fastener 306a (if desired) to secure first and second segments 302a, 304a in a preferred position. Working end 402a of instrument 400a preferably has a driver portion 404a configured to cooperatively engage driver receiving opening 364a in fastener 306a. Driver portion 404a is preferably hex-shaped. Working end 402a preferably has a pin 406a extending therefrom and displaced from driver portion 404a to engage one of pin receiving recesses $362a_1$ and $362a_2$, respectively, when driver portion 404a is engaged with driver receiving opening 364a in fastener 306a. With driver portion 404a engaging fastener 306a and pin 406a inserted in pin receiving recess $362a_2$ as shown in FIG. 25A, instrument 400a rotates fastener 306a in the direction of arrow A as shown in FIG. 26A to move first segment 302a toward second segment 304a in the direction of arrow B to reduce the length of plate 300a and can if desired concurrently tighten fastener 306a. The configuration of plate 300a provides for an internal compression mechanism that can be operated by a driver instrument eliminating the need for an externally applied compression apparatus for shortening plate 300a and creating a compressive load.

FIGS. 19B, 20B, 21B, 22B, and 24B show another preferred embodiment of a cervical plate 300b in accordance with the present invention similar to plate 300a. In this preferred embodiment of the present invention, plate 300b may include at least one bone screw lock adapted to lock to the plate only a single bone screw inserted into one of bone screw receiving holes 326b such as described above in relation to plate 100a and a non-detachable fastener 306b configured to couple together first and second segments 302b, 304b such as described above in relation to plate 100b.

FIGS. 16C, 17C 18C, 19C, 21C, 22C, 23C, and 24C show another preferred embodiment of a cervical plate 300c in accordance with the present invention similar to plate 300a. In this preferred embodiment of the present invention, plate 300c may include a detachable fastener configured to couple together first and second segments 302c, 304c such as described above in relation to plate 100a and a bone screw lock adapted to lock at least two bone screws inserted in bone screw receiving holes 326c such as described above in relation to plate 100c.

FIGS. 19D, 21D, 22D, and 24D show another preferred embodiment of a cervical plate 300d in accordance with the present invention similar to plate 300a. In this preferred embodiment of the present invention, plate 300d may include a non-detachable fastener configured to couple together first and second segments 302d, 304d such as described above in relation to plate 100b and a bone screw lock adapted to lock at least two bone screws inserted into bone screw receiving holes 326d such as described above in relation to plate 100c.

Figure 27A:
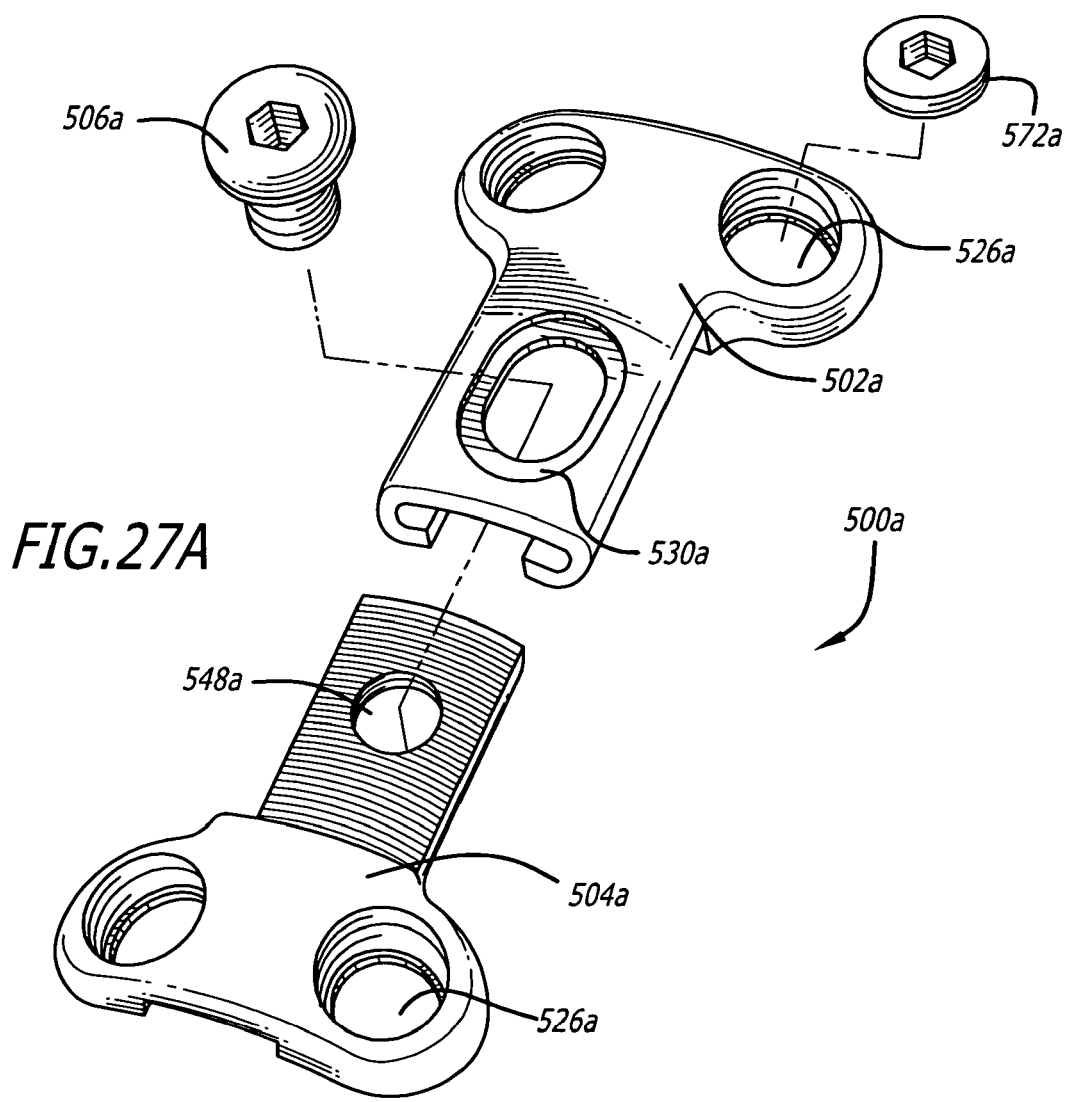
FIG. 27A is an exploded top perspective view of a plate, a fastener, and locking element in accordance with another preferred embodiment of the present invention.
Figure 28A:
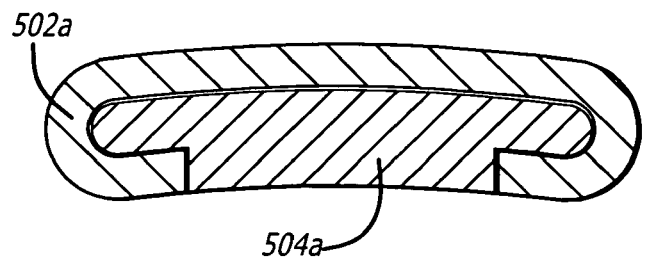
FIG. 28A is a cross sectional view transverse to the longitudinal axis of the plate of FIGS. 27A-27D.

FIGS. 27A and 28A show another preferred embodiment of a cervical plate 500a in accordance with the present invention. Plate 500a is similar to plate 100a except that first segment 502a is configured to receive at least a portion of second segment 504a therein in a tongue and groove configuration. As shown in FIG. 28A, first segment 502a preferably has a C-shaped cross section and second segment 504a preferably has a T-shaped cross section. The configurations of segments 502a, 504a in this embodiment of the present invention keep segments 502a, 504a aligned along the longitudinal axis of plate 500a and limit movement of segments 502a, 504a in a direction generally transverse to the longitudinal axis of plate 500a. A person of ordinary skill in the art would appreciate that other configurations of cooperatively engaging first and second segments 502a, 504a are possible without departing from the intended purpose within the broad scope of the present invention. Bone screw lock 572a is adapted to lock to plate 500a one bone screw inserted in one of bone screw receiving holes 526a.

Figure 27B:
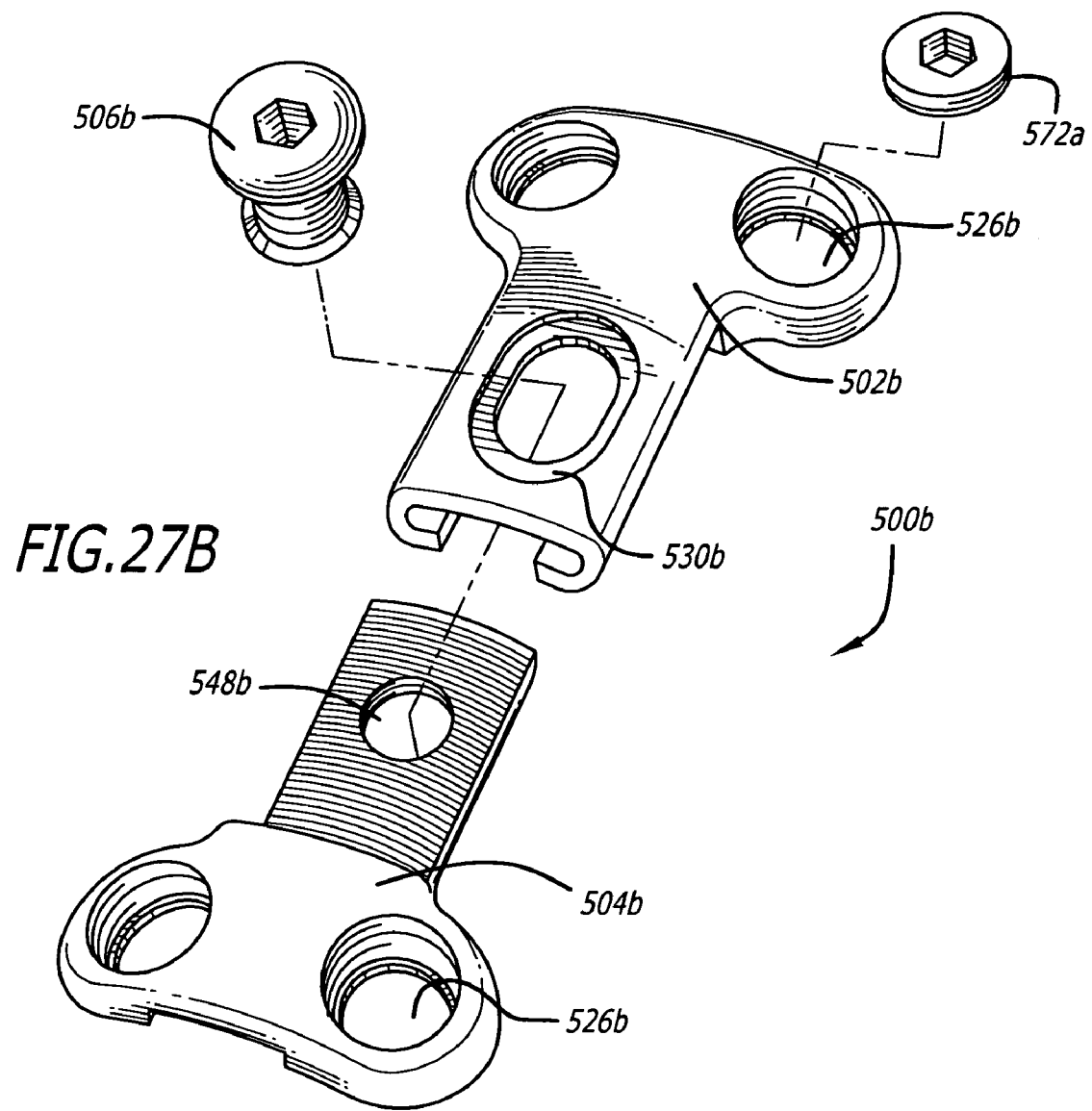
FIG. 27B is an exploded top perspective view of a plate, a fastener, and locking element in accordance with another preferred embodiment of the present invention.

FIG. 27B shows another preferred embodiment of a cervical plate 500b in accordance with the present invention similar to plate 500a. In this preferred embodiment of the present invention, plate 500b may include at least one bone screw lock adapted to lock to the plate only a single bone screw inserted into one of bone screw receiving holes 526b such as described above in relation to plate 100a and a non-detachable fastener 506b configured to couple together first and second segments 502b, 504b such as described above in relation to plate 100b.

Figure 27C:
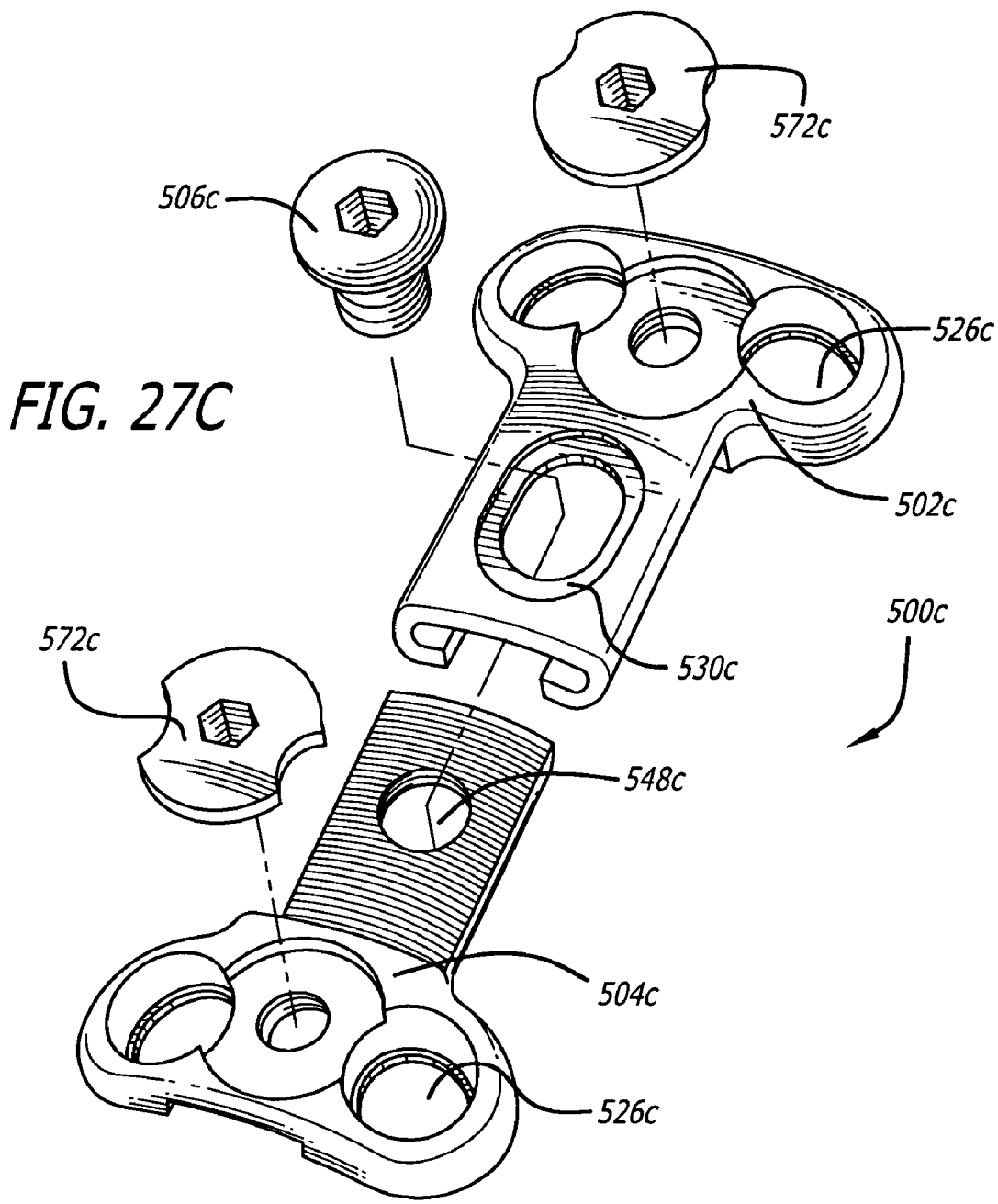
FIG. 27C is an exploded top perspective view of a plate, a fastener, and locking elements in accordance with another preferred embodiment of the present invention.

FIG. 27C shows another preferred embodiment of a cervical plate 500c in accordance with the present invention similar to plate 500a. In this preferred embodiment of the present invention, plate 500c may include a detachable fastener configured to couple together first and second segments 502c, 504c such as described above in relation to plate 100a and a bone screw lock adapted to lock at least two bone screws inserted in bone screw receiving holes 526c such as described above in relation to plate 100c.

Figure 27D:
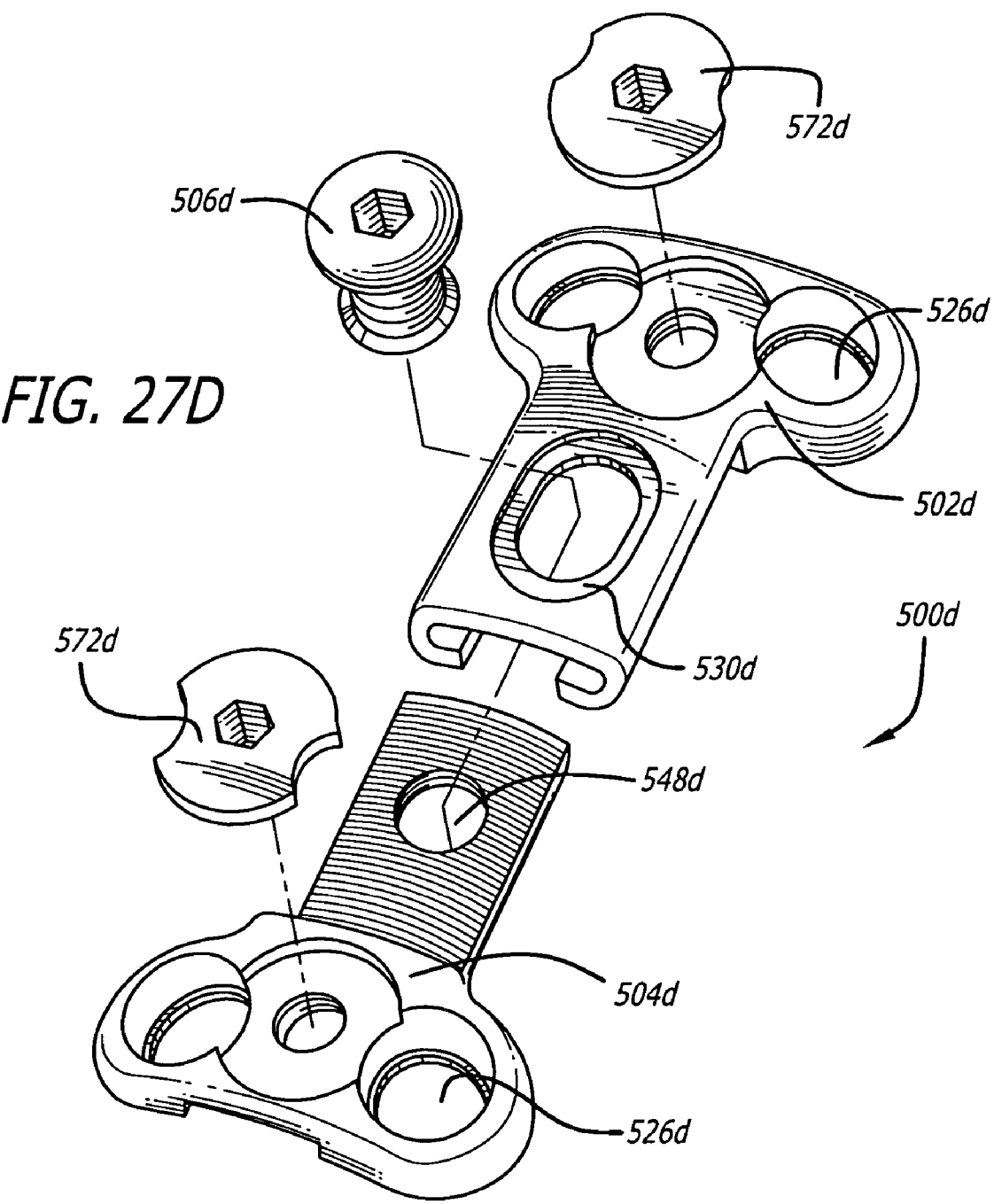
FIG. 27D is an exploded top perspective view of a plate, a fastener, and locking elements in accordance with another preferred embodiment of the present invention.
Figure 29A:
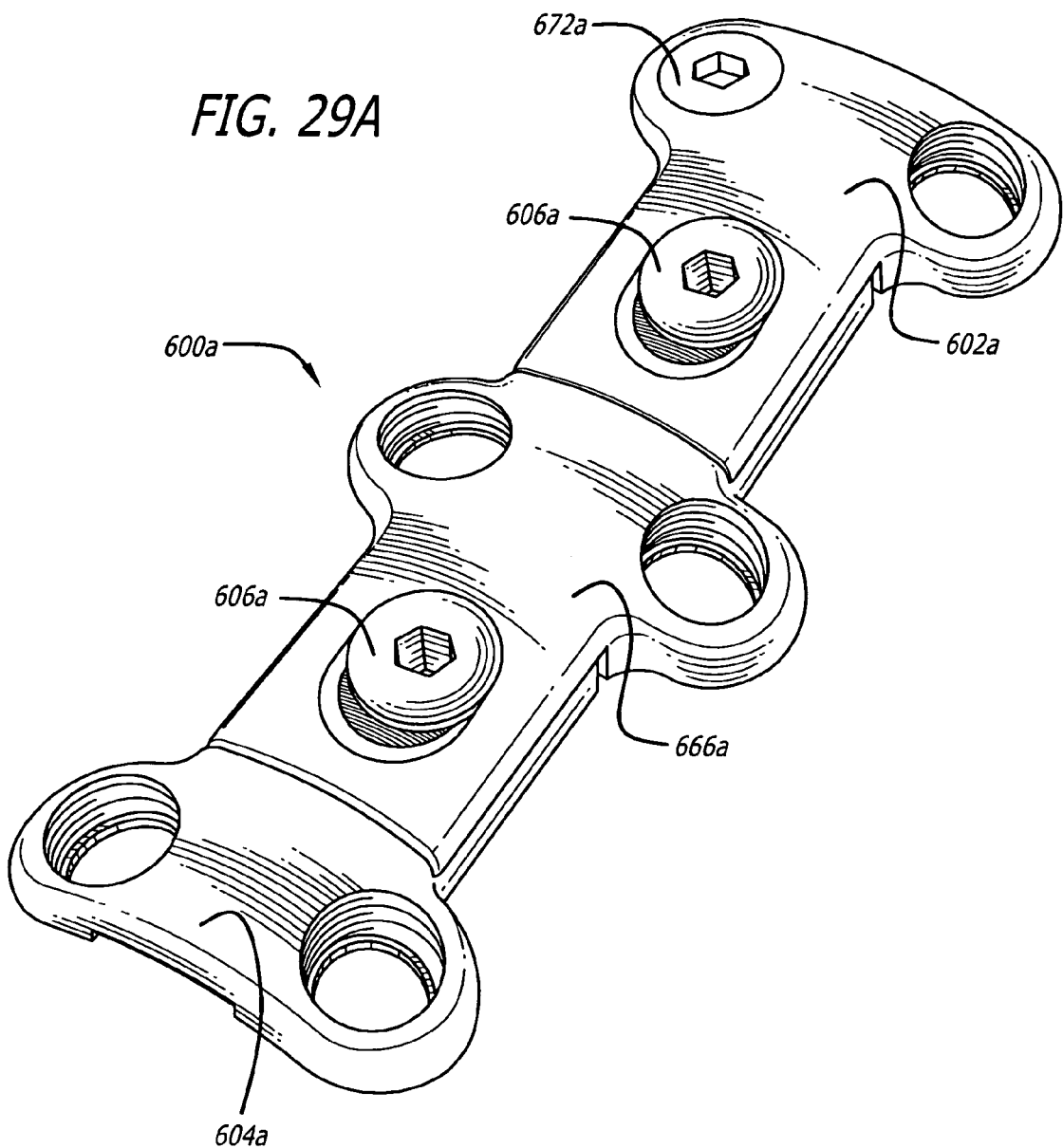
FIG. 29A is a top plan view of a plate, fasteners, and locking element in accordance with another preferred embodiment of the present invention.
Figure 29C:
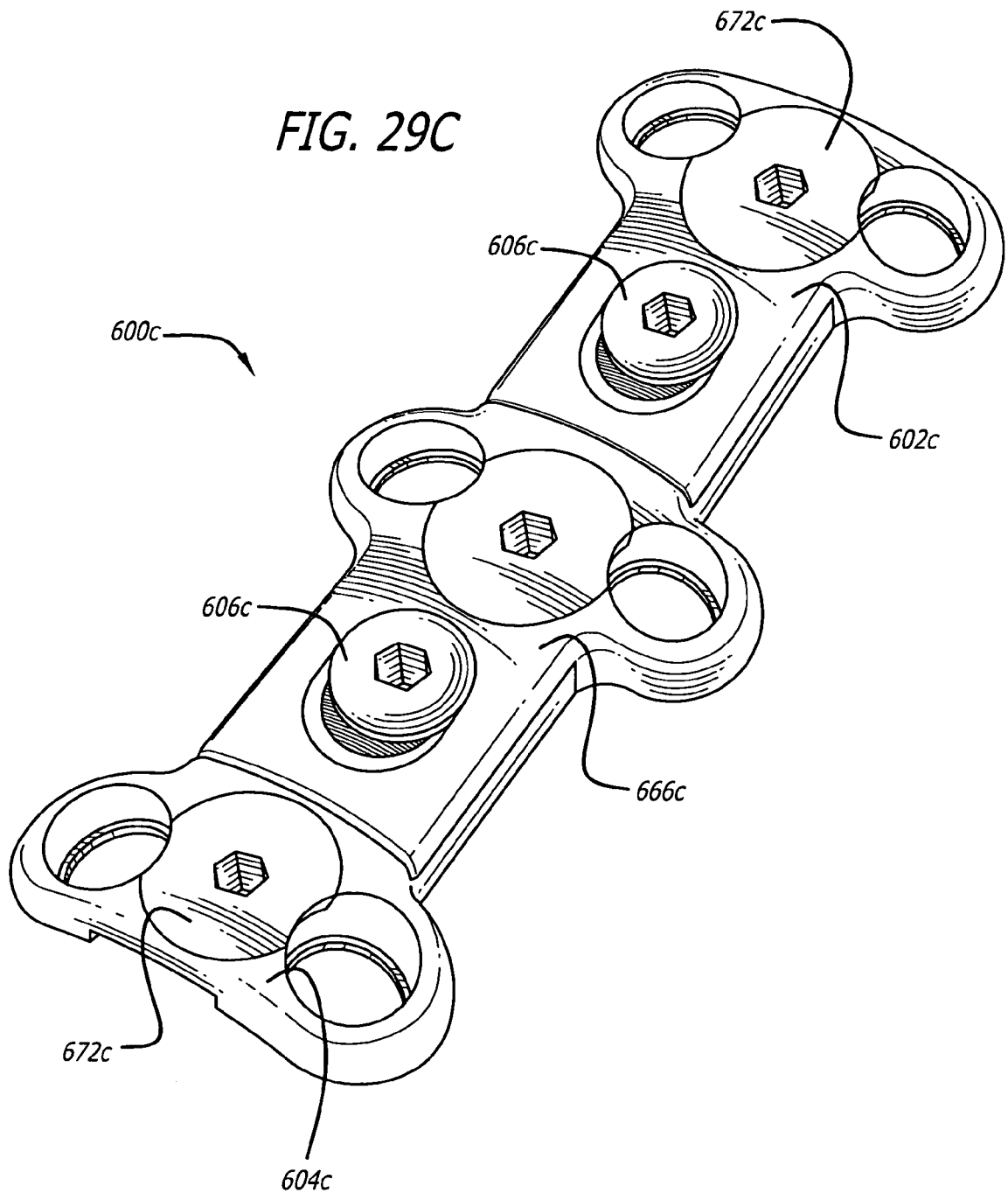
FIG. 29C is a top plan view of a plate, fasteners, and locking elements in accordance with another preferred embodiment of the present invention.
Figure 30A:
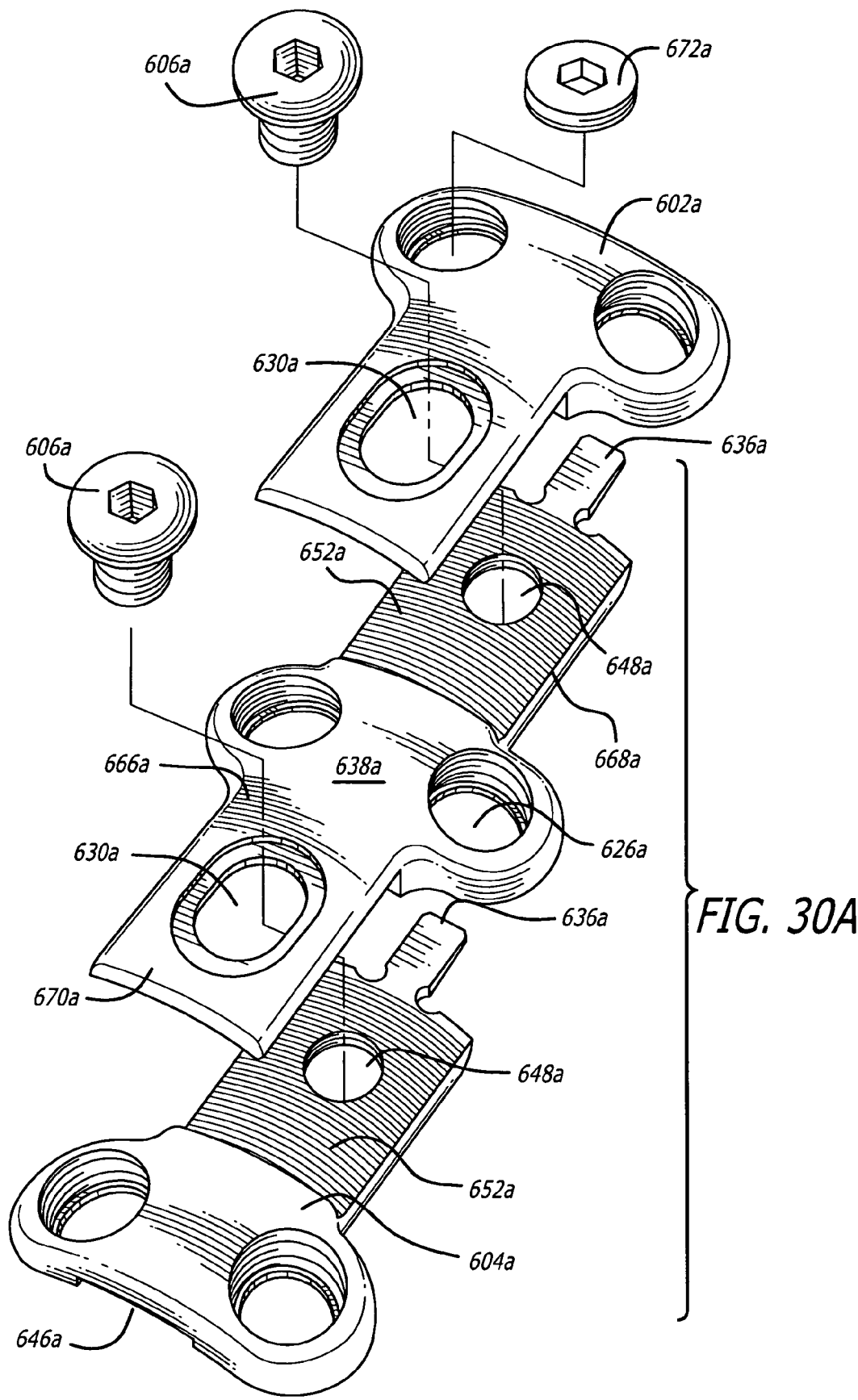
FIG. 30A is an exploded top perspective view of the plate, fasteners, and locking element of FIG. 29A.
Figure 30B:
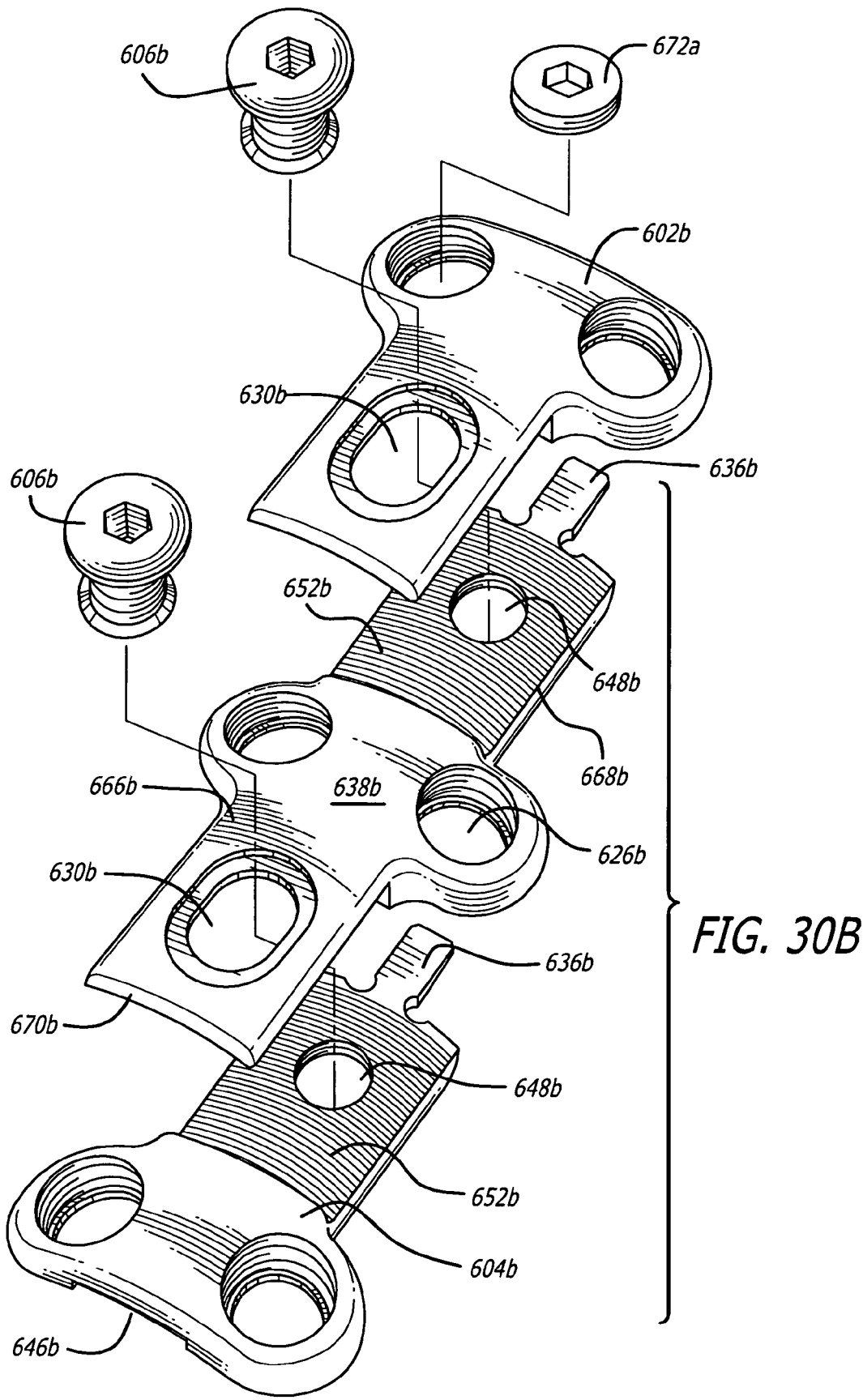
FIG. 30B is an exploded top perspective view of another preferred embodiment of the plate, fasteners, and locking element of FIG. 29A.
Figure 30C:
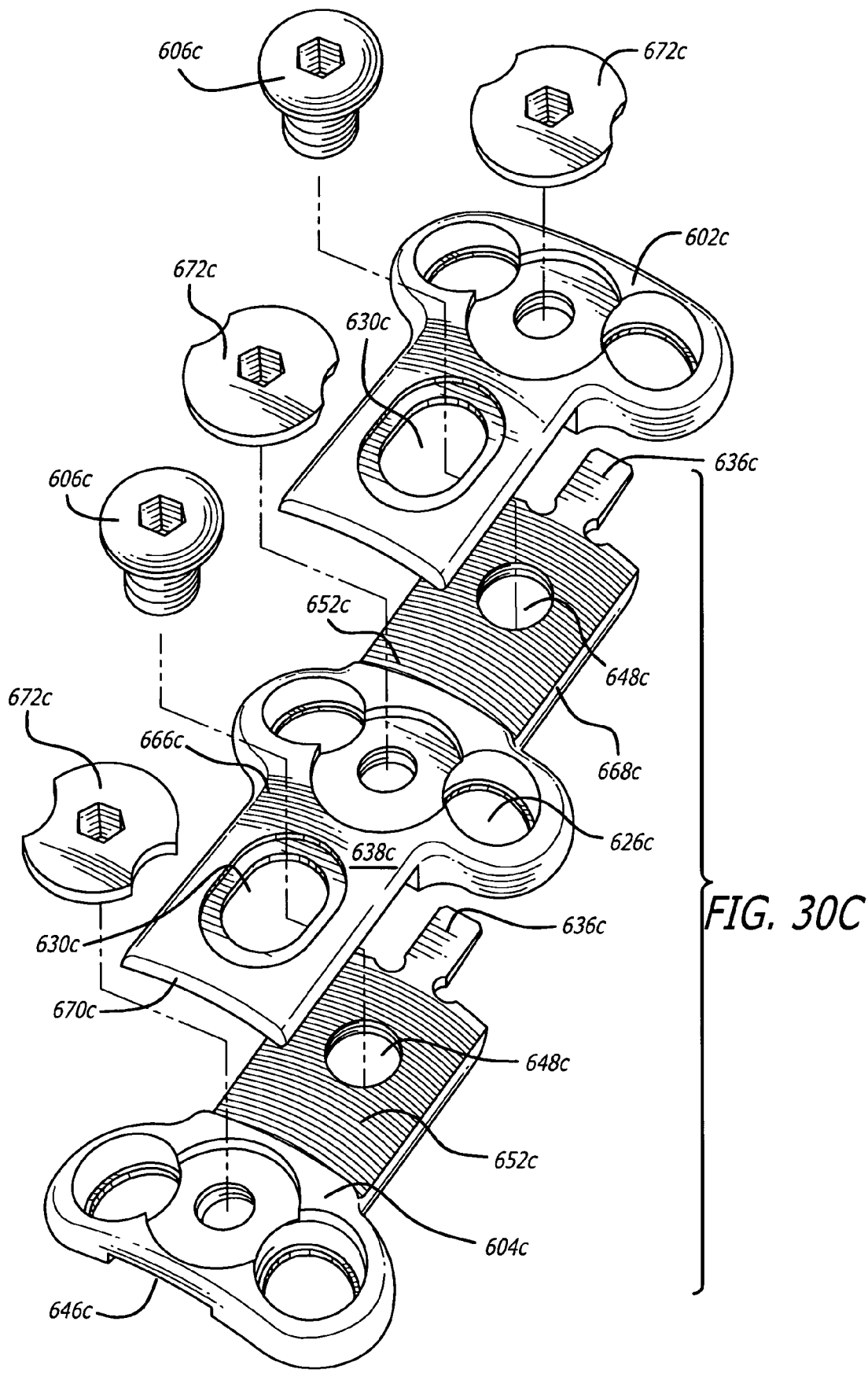
FIG. 30C is an exploded top perspective view of the plate, fasteners, and locking elements of FIG. 29C.
Figure 30D:
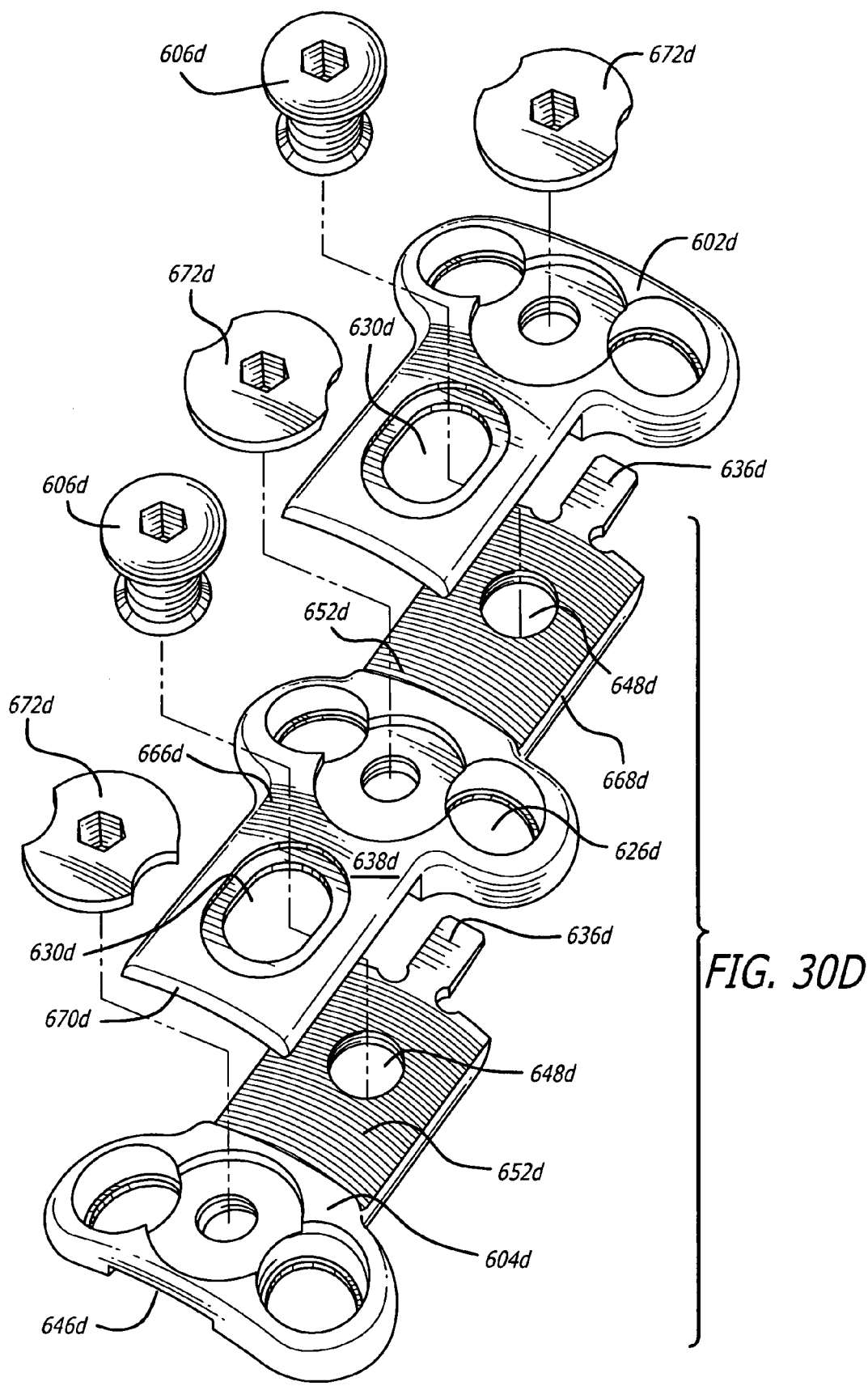
FIG. 30D is an exploded top perspective view of another preferred embodiment of the plate, fasteners, and locking elements of FIG. 29C.
Figure 31A:
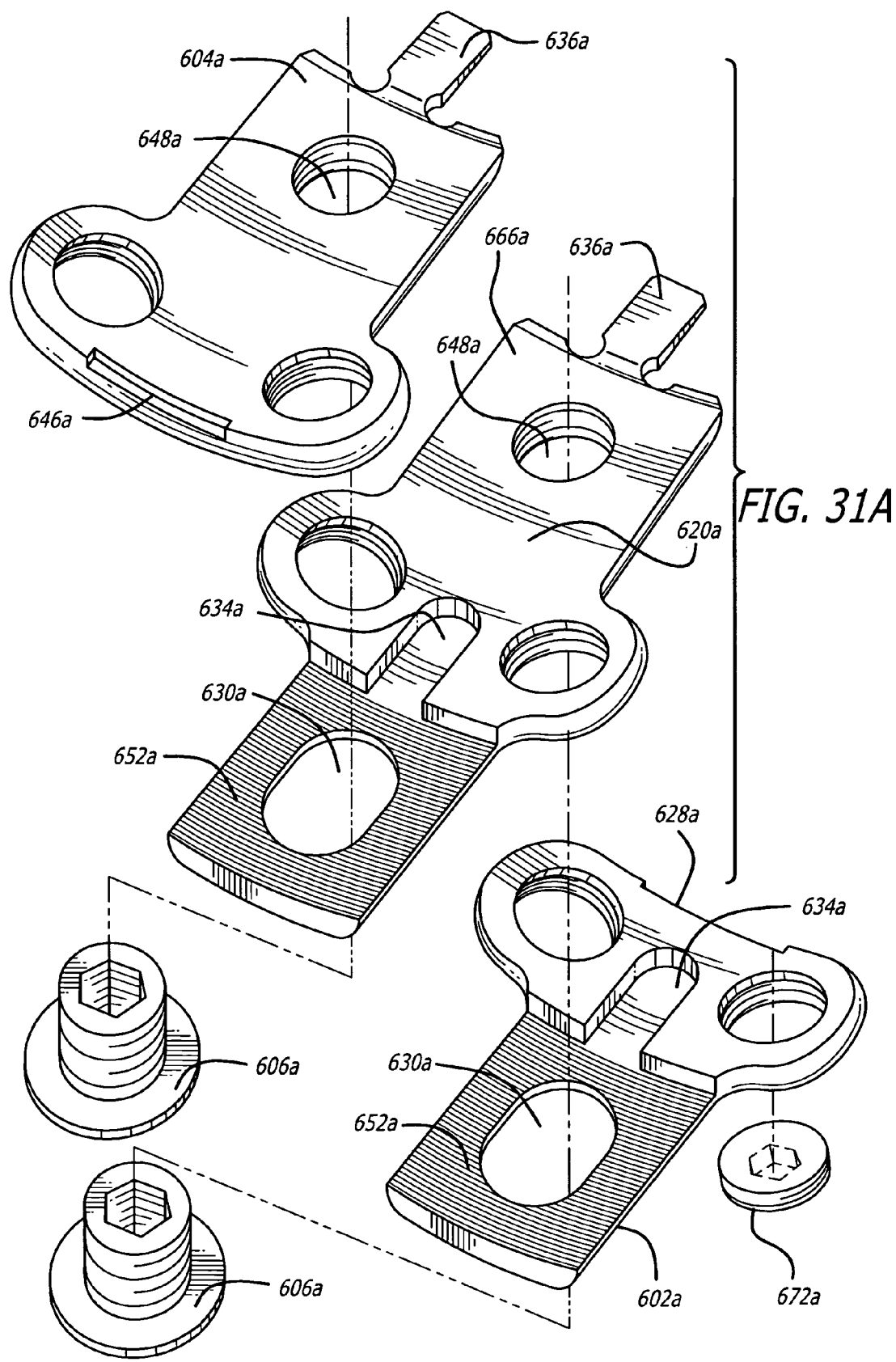
FIG. 31A is an exploded bottom perspective view of the plate, fasteners, and locking element of FIG. 30A.
Figure 31B:
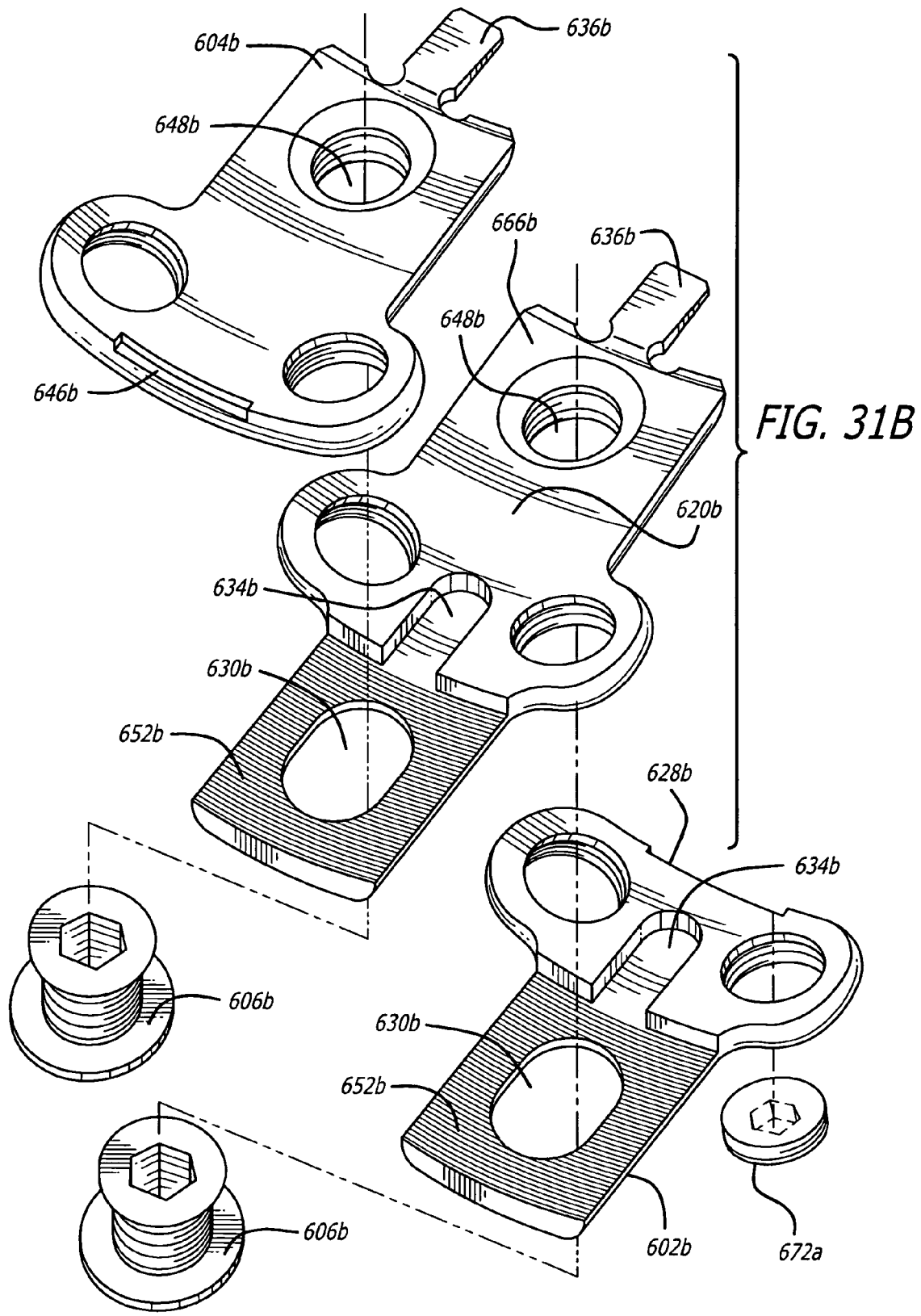
FIG. 31B is an exploded bottom perspective view of the plate, fasteners, and locking element of FIG. 30B.
Figure 31C:
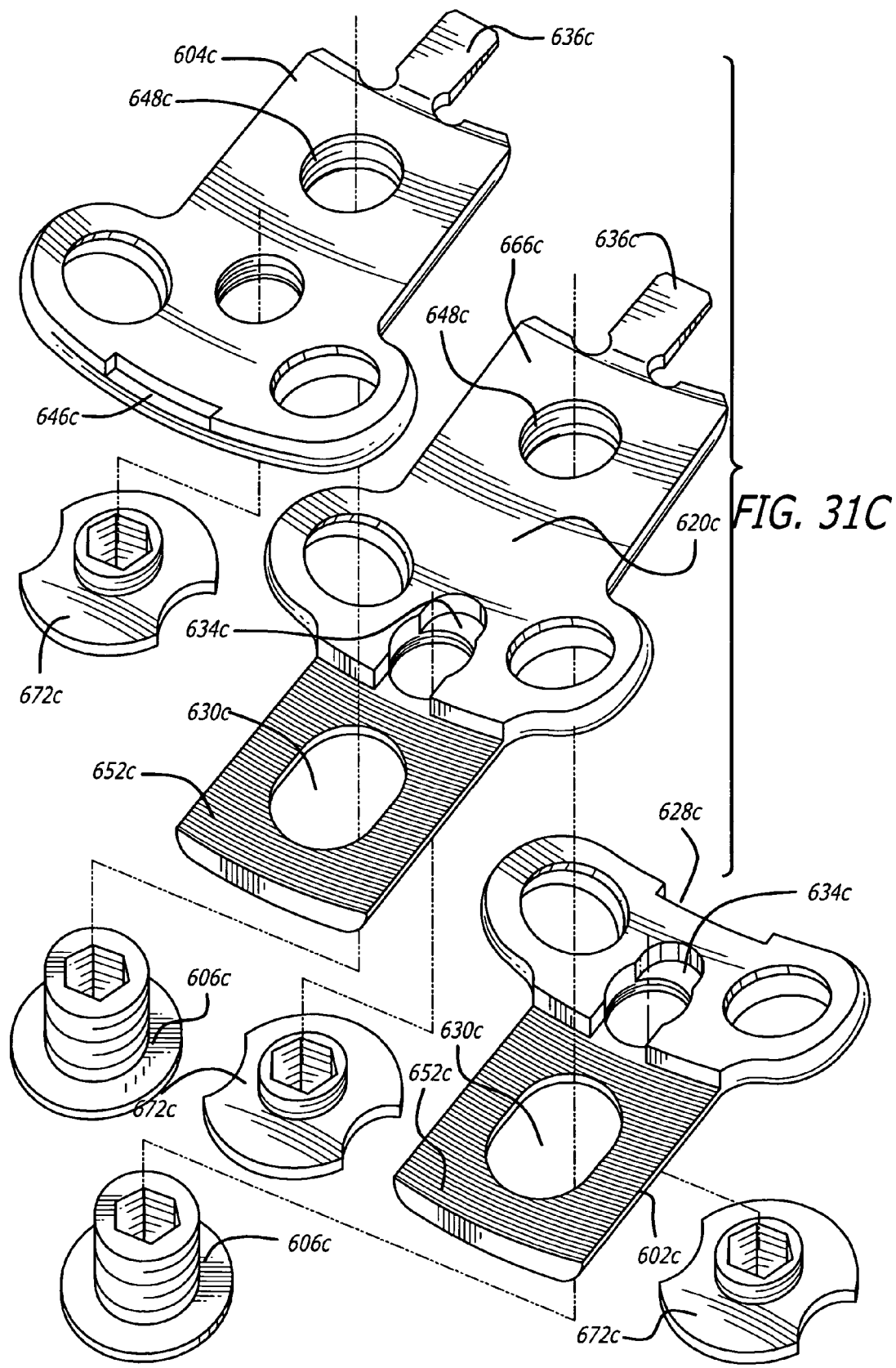
FIG. 31C is an exploded bottom perspective view of the plate, fasteners, and locking elements of FIG. 30C.
Figure 31D:
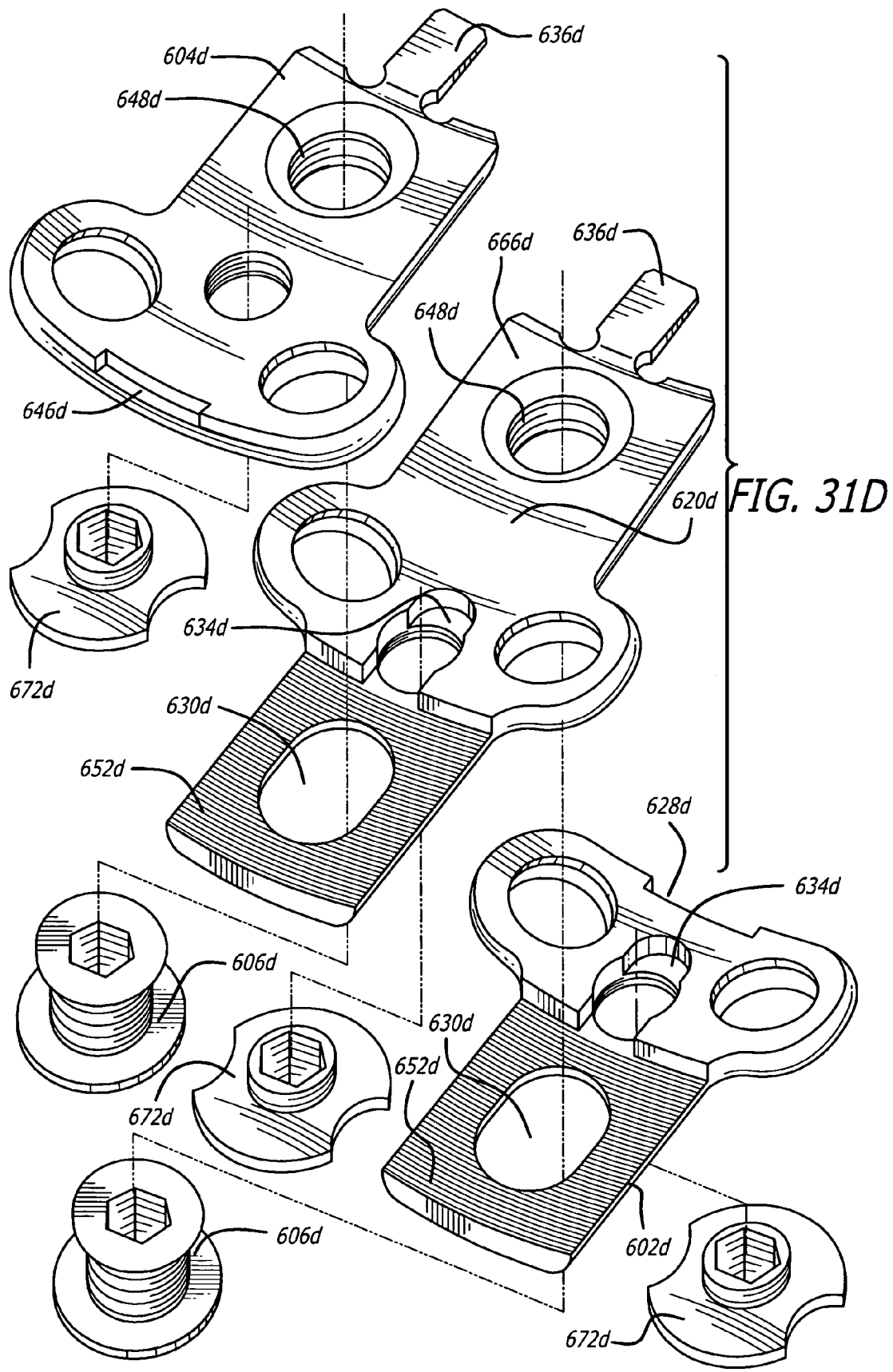
FIG. 31D is an exploded bottom perspective view of the plate, fasteners, and locking elements of FIG. 30D.
Figure 33B:
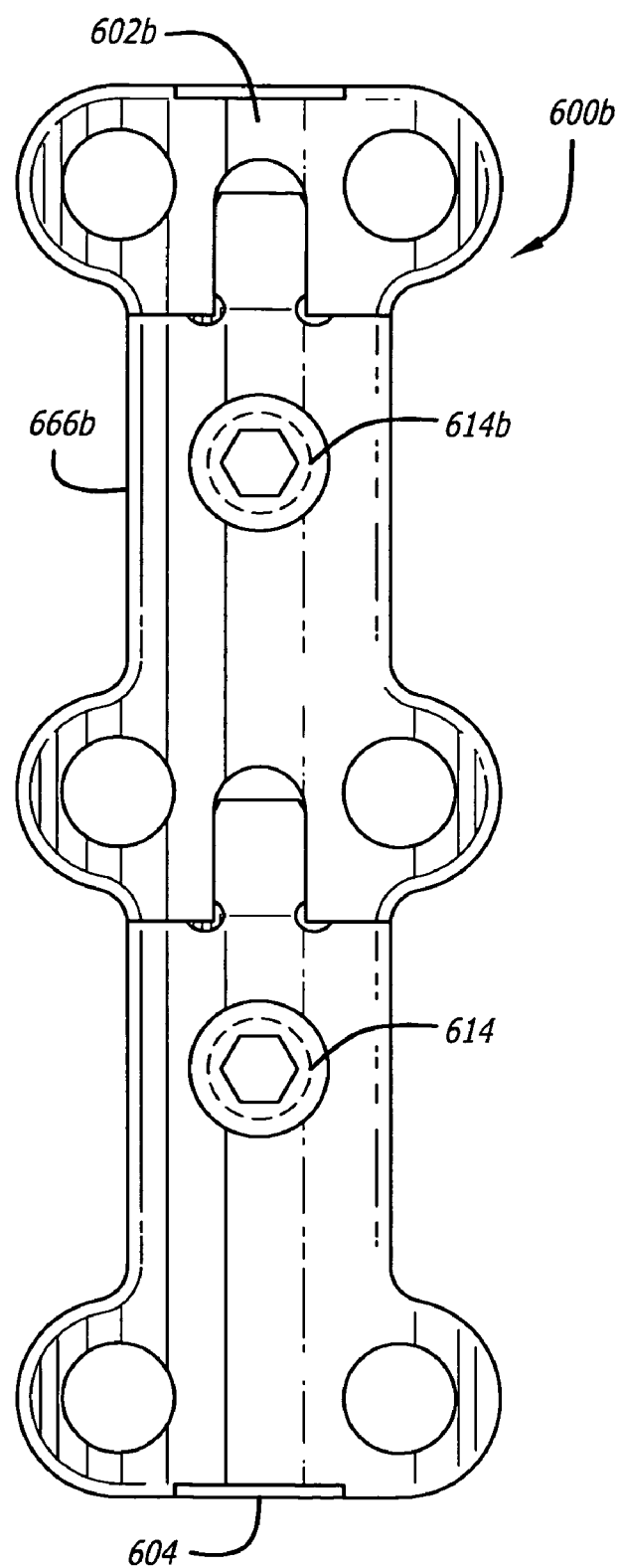
FIG. 33B is a bottom plan view of the plate and fasteners of FIG. 30B.
Figure 33D:
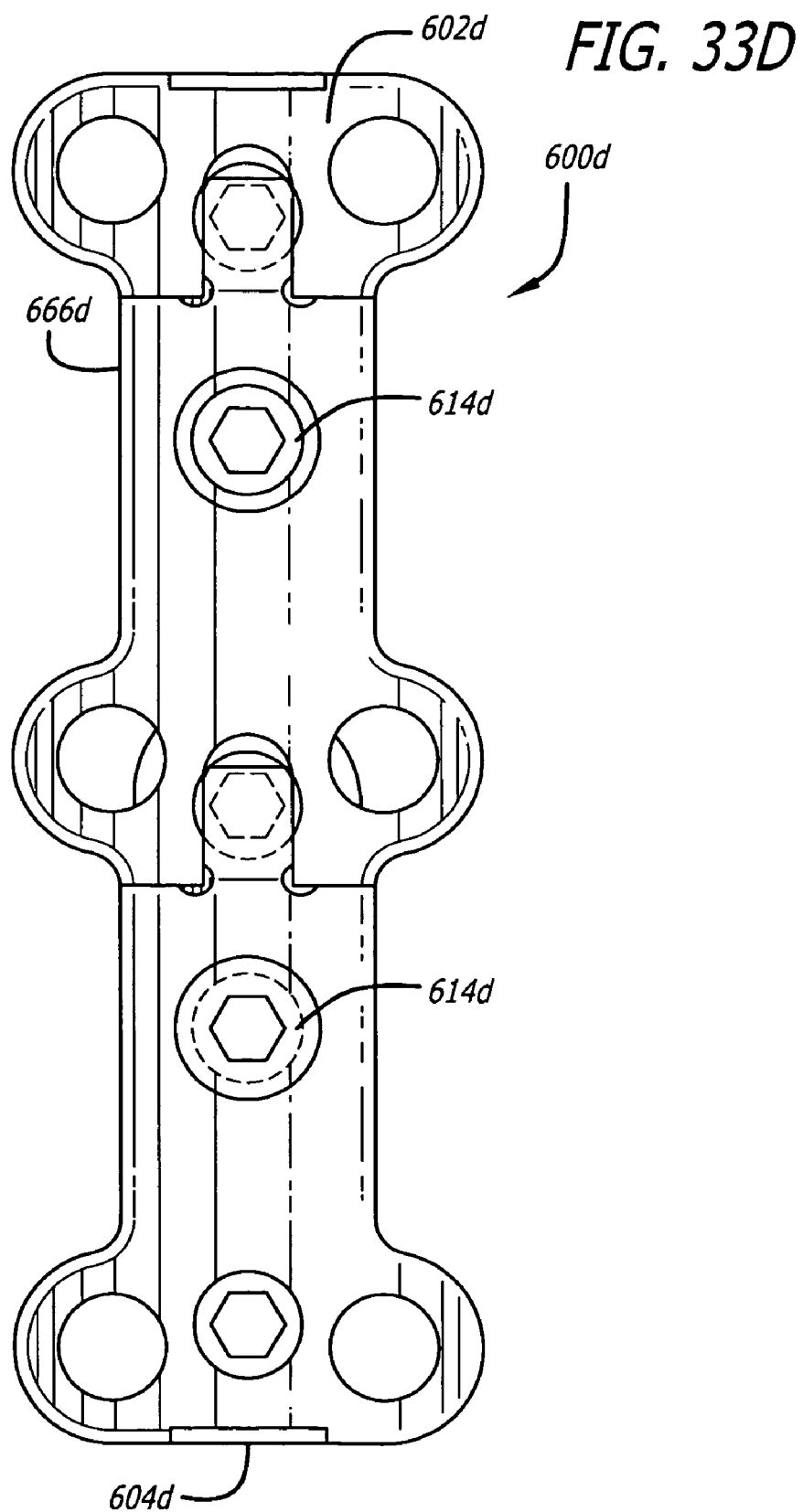
FIG. 33D is a bottom plan view of the plate, fasteners, and locking elements of FIG. 30D.
Figure 35A:
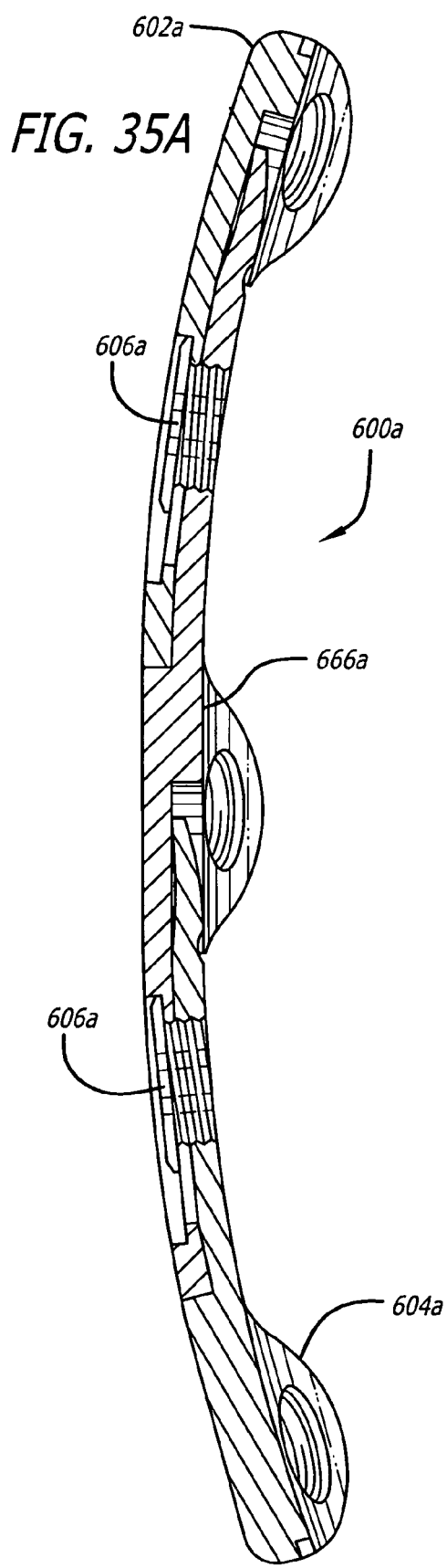
FIG. 35A is a partial cross sectional view along the longitudinal axis of the plate of FIG. 30A.
Figure 36A:
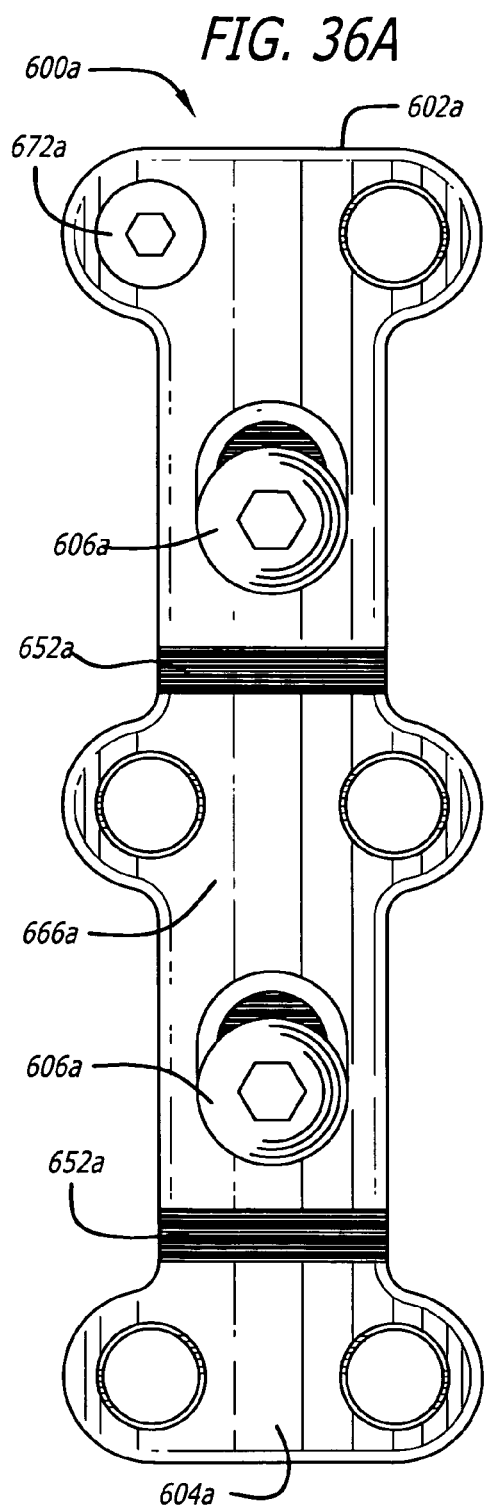
FIG. 36A is a top plan view of the plates in an elongated position, fasteners, and locking element of FIGS. 30A and 30B.
Figure 35B:
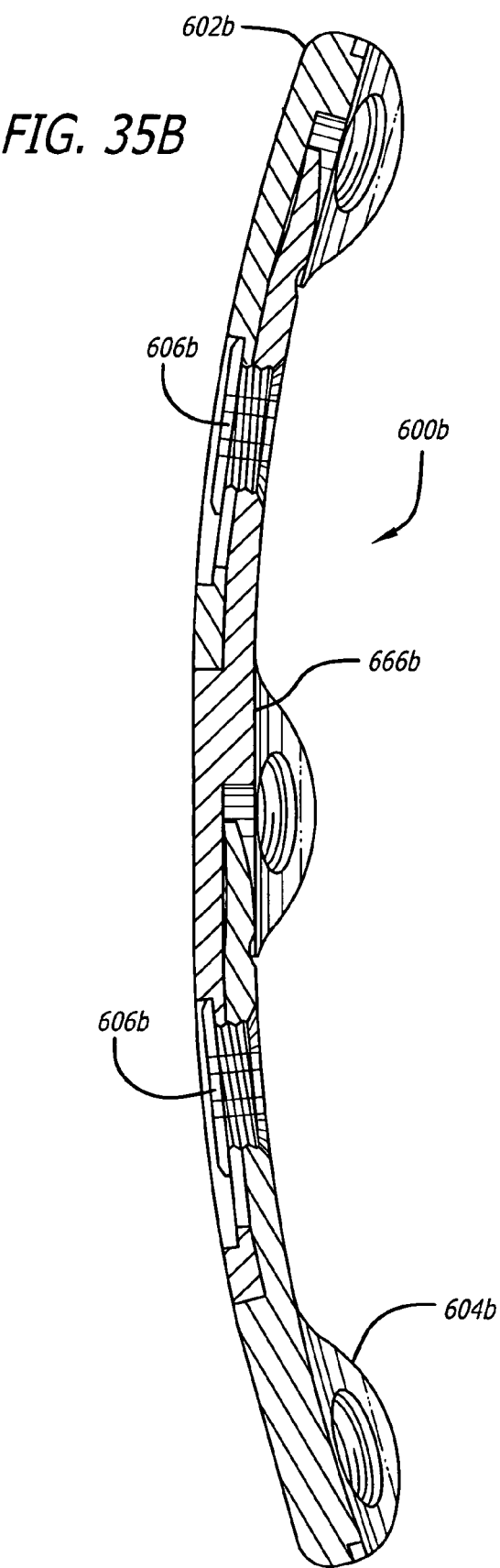
FIG. 35B is a partial cross sectional view along the longitudinal axis of the plate of FIG. 30B.
Figure 35D:
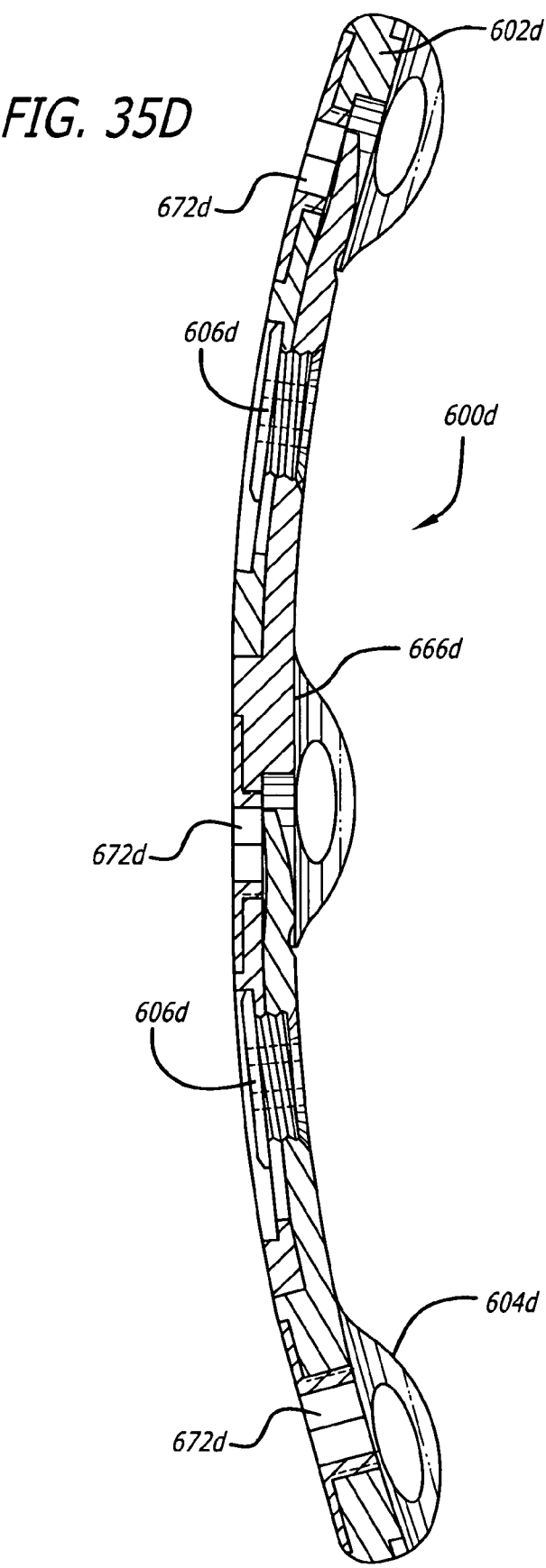
FIG. 35D is a partial cross sectional view along the longitudinal axis of the plate of FIG. 30D.

FIG. 27D shows another preferred embodiment of a cervical plate 500d in accordance with the present invention similar to plate 500a. In this preferred embodiment of the present invention, plate 500d may include a non-detachable fastener configured to couple together first and second segments 502d, 504d such as described above in relation to plate 100b and a bone screw lock adapted to lock at least two bone screws inserted into bone screw receiving holes 526d such as described above in relation to plate 100c.

FIGS. 29A, 30A, 31A, 32A, 33A, 34A, 35A, and -36A show another preferred embodiment of a cervical plate 600a in accordance with the present invention. Plate 600a is similar to plate 100a except that it is configured for use across two levels of the cervical spine. In addition to the elements of plate 100a, plate 600a further includes an intermediate third segment 666a between first and second segments 602a, 604a. Third segment 666a has a first end 668a configured to cooperatively engage first segment 602a. Third segment 666a has a second end 670a configured to cooperatively engage second segment 604a. Third segment 666a and first and second segments 602a, 604a are articulated and can be moved to vary the spacing between the bone screw receiving holes of the plate segments as well as the overall length of the plate. Third segment 666a can be made of different lengths and/or configurations to vary the distance between first and second segments 602a, 604a to further vary the spacing between the bone screw receiving holes and further vary the overall length of the plate.

In a preferred embodiment of the present invention, plate 600a could be provided to the health care facility in a set of segments. For example, a set or group of six segments could include a longer and a shorter one of first, second, and third segments 602a, 604a, 666a. These segments could be assembled to cover a range of sizes. Additional intermediate segments 666a can be used to assemble a plate that covers additional levels of the spine and preferably the spacing between plate segments would be adjustable.

First end 668a of third segment 666a has similar features to second segment 604a including a fastener receiving recess 648a, bone screw receiving holes 626a, ratchetings 652a on at least a portion of its upper surface 638a, and a tab 636a. Second end 670a of third segment 666a has similar features to first segment 602a including a ratchetings 652a on at least a portion of its lower surface 620a and a tab receiving recess 634a. A first fastener 606a couples together first segment 602a to first end 668a of third segment 666a. A second fastener couples together second segment 604a to second end 670a of third segment 666a. Additional segments 666a may be added for use across more than two levels of the spine. Segments 666a are configured to be coupled together with first end 668a of one segment 666a to second end 670a of another segment 666a. Bone screw lock 672a is adapted to lock to plate 600a at least two bone screws inserted in bone screw receiving holes 626a.

Figure 37A:
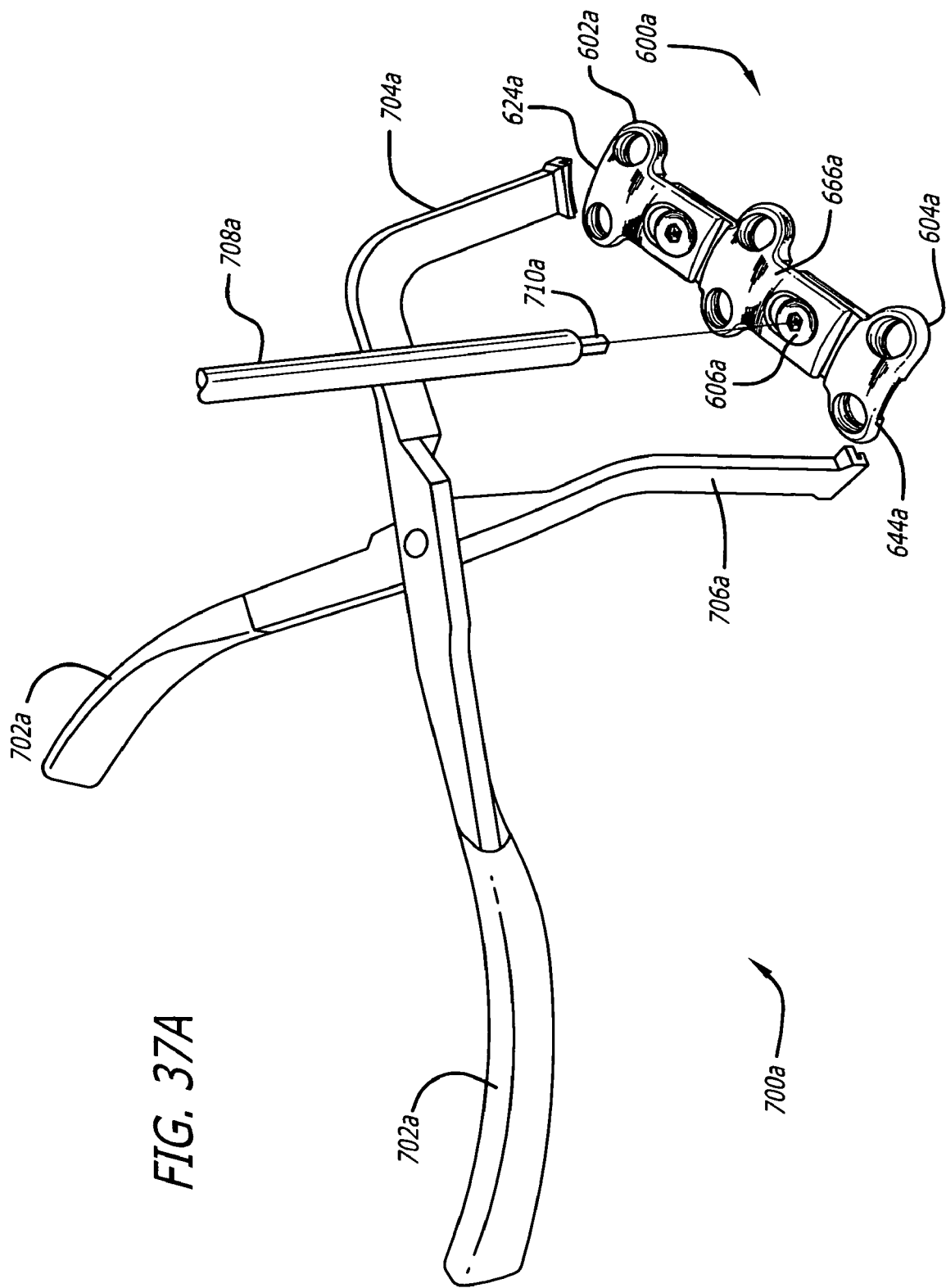
FIG. 37A is a top perspective view of one of the plates of FIGS. 30A and 30B and another preferred embodiment of instrumentation for compressing the plate and instrumentation for locking the fastener in accordance with the present invention.
Figure 37C:
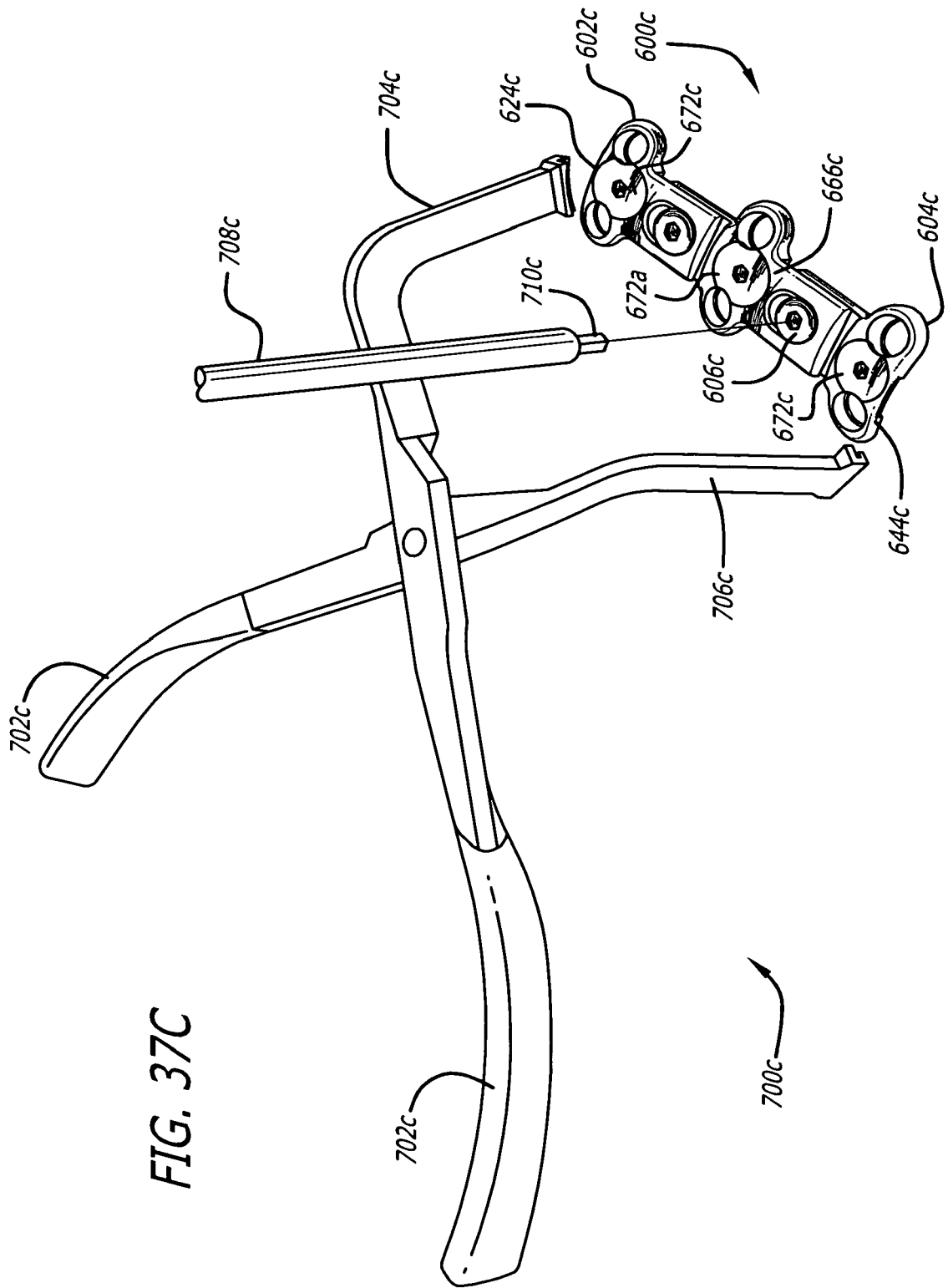
FIG. 37C is a top perspective view of one of the plates of FIGS. 30C and 30D and another preferred embodiment of instrumentation for compressing the plate and instrumentation for locking the fastener in accordance with the present invention.

FIGS. 37A, 38A, and- 39A show a preferred embodiment of instrumentation 700a for compressing and locking plate 600a. Instrumentation 700a has a handle 702a with a pair of tongs 704a, 706a in moveable relationship to each. Tongs 704a, 706a are configured to cooperatively engage ends 624a, 644a of first and second segments, 602a, 604a, respectively, to shorten the overall length of the plate and to apply a desired compressive load across multiple levels of the spine. Instrumentation 700a may be used to position plate 600a in a desired position at the fusion site during at least a portion of the procedure for installing plate 600a. An instrument may be used for holding the plate such as the instrumentation disclosed in the '721 patent incorporated by reference above. Instrument 700a can be used to move segments 602a, 604a toward one another and toward third segment 666a to shorten the length of plate 600a and create a compressive load across the respective disc spaces.

As shown in FIG. 38A, an alternative embodiment of instrument 700a' may be used to move first or second segment 602a, 604a toward third segment 666a so that a compressive load may be applied to one disc space at a time. Instrument 700a' has a tong 704a' similar to tong 704a for engaging one of ends 624a, 644a of first and second segments 602a, 604a, and forked tong 707a for engaging the third segment as shown in FIG. 38A.

After the desired length of plate 600a is achieved, an instrument 708a having a head 710a configured to cooperatively engage fastener 606a is used to tighten fastener 606a to secure first, second, and third segments 602a, 604a, 666a in a desired position.

FIGS. 30B, 31B, 33B, and 35B show another preferred embodiment of a cervical plate 600b in accordance with the present invention similar to plate 600a. In this preferred embodiment of the present invention, plate 600b may include at least one bone screw lock adapted to lock to the plate only a single bone screw inserted into one of bone screw receiving holes 626b such as described above in relation to plate 100a and a non-detachable fastener 606b configured to couple together first and second segments 602b, 604b such as described above in relation to plate 100b.

FIGS. 29C, 30C, 31C, 32C, 33C, 34C, 35C, 36C, 37C, 38C, and 39C show another preferred embodiment of a cervical plate 600c in accordance with the present invention similar to plate 600a. In this preferred embodiment of the present invention, plate 600c may include a detachable fastener configured to couple together first and second segments 602c, 604c such as described above in relation to plate 100a and a bone screw lock adapted to lock at least two bone screws inserted in bone screw receiving holes 626c such as described above in relation to plate 100c.

FIGS. 30D, 31D, 33D, and 35D show another preferred embodiment of a cervical plate 600d in accordance with the present invention similar to plate 600a. In this preferred embodiment of the present invention, plate 600d may include a non-detachable fastener configured to couple together first and second segments 602d, 604d such as described above in relation to plate 100b and a bone screw lock adapted to lock at least two bone screws inserted into bone screw receiving holes 626d such as described above in relation to plate 100c.

FIG. 40A shows another preferred embodiment of a cervical plate 800a in accordance with the present invention. Plate 800a is similar to plate 600a except that first segment 802a is configured to receive at least a portion of the first end 868a of third segment 866a therein in a tongue and groove configuration and second end 870a of third segment 866a is configured to receive at least a portion of second segment 804a therein, in a tongue and groove configuration. A person of ordinary skill in the art would appreciate that other configurations of cooperatively engaging first and second segments 802a, 804a are possible without departing from the intended purpose within the broad scope of the present invention. Bone screw lock 872a is adapted to lock to plate 800a at least two bone screws inserted in bone screw receiving holes 826a.

Figure 40B:
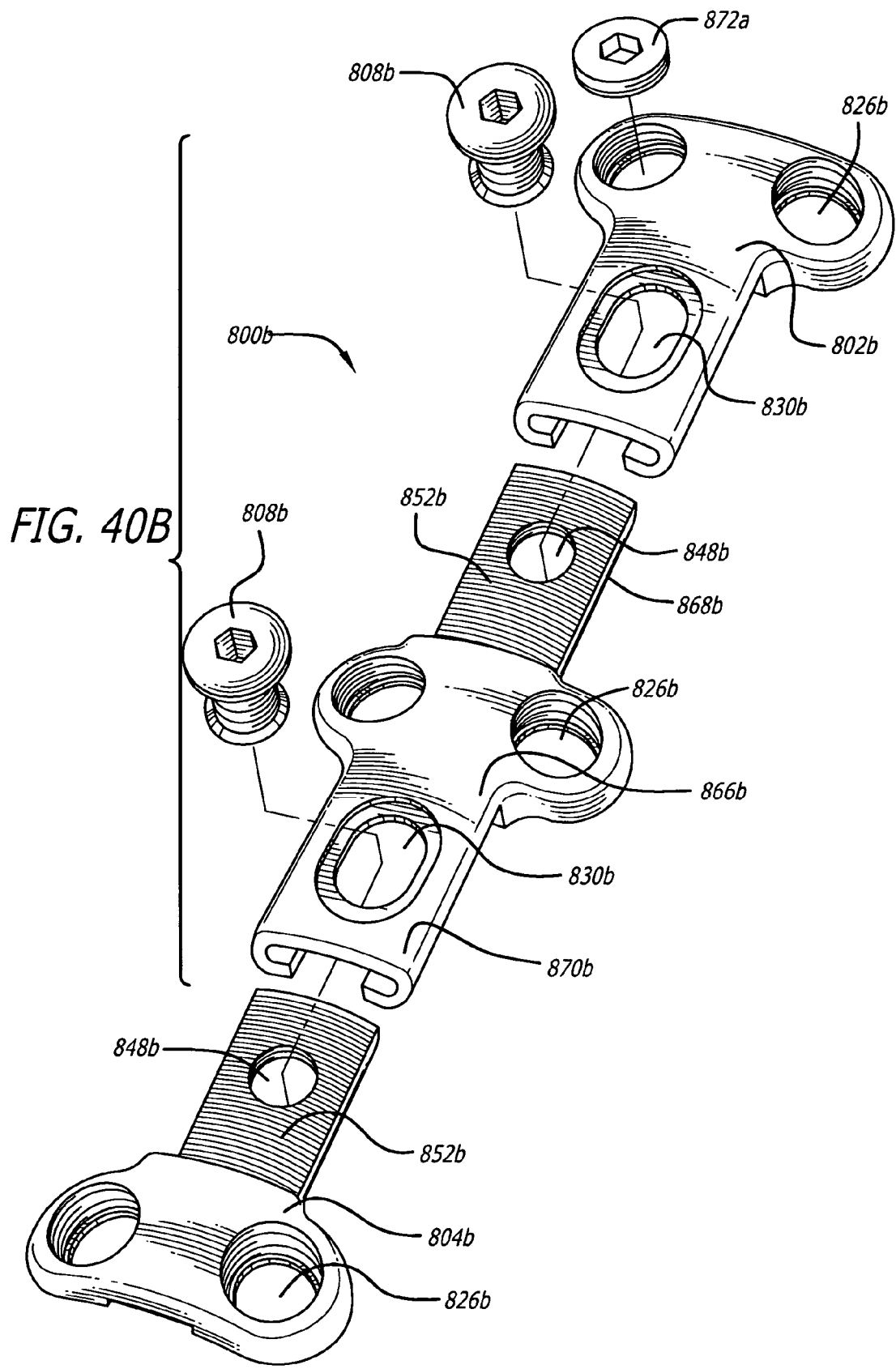
FIG. 40B is an exploded top perspective view of a plate, fasteners, and a locking element in accordance with another preferred embodiment of the present invention.

FIG. 40B shows another preferred embodiment of a cervical plate 800b in accordance with the present invention similar to plate 800a. In this preferred embodiment of the present invention, plate 800b may include at least one bone screw lock adapted to lock to the plate only a single bone screw inserted into one of bone screw receiving holes 826b such as described above in relation to plate 100a and a non-detachable fastener 806b configured to couple together first and second segments 802b, 804b such as described above in relation to plate 100b.

Figure 40C:
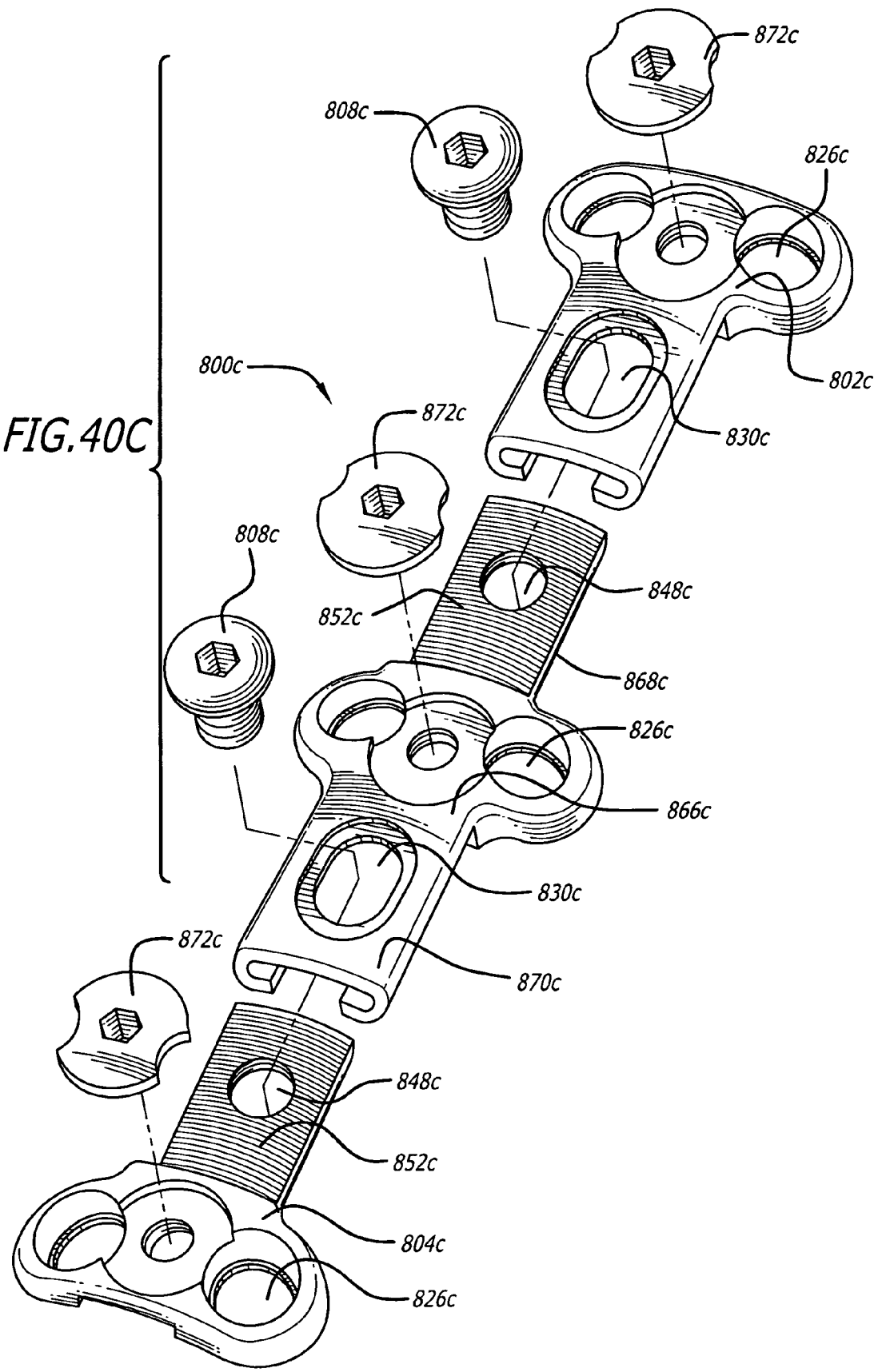
FIG. 40C is an exploded top perspective view of a plate, fasteners, and locking elements in accordance with another preferred embodiment of the present invention.

FIG. 40C shows another preferred embodiment of a cervical plate 800c in accordance with the present invention similar to plate 800a. In this preferred embodiment of the present invention, plate 800c may include a detachable fastener configured to couple together first and second segments 802c, 804c such as described above in relation to plate 100a and a bone screw lock adapted to lock at least two bone screws inserted in bone screw receiving holes 826c such as described above in relation to plate 100c.

FIG. 40D shows another preferred embodiment of a cervical plate 800d in accordance with the present invention similar to plate 800a. In this preferred embodiment of the present invention, plate 800d may include a non-detachable fastener configured to couple together first and second segments 802d, 804d such as described above in relation to plate 100b and a bone screw lock adapted to lock at least two bone screws inserted into bone screw receiving holes 826d such as described above in relation to plate 100c.

FIG. 41 shows a cervical plate 900c with locking elements 902c in accordance with another preferred embodiment of the present invention. Locking elements 902c are adapted to lock at least two bone screws installed in each of bone screw receiving holes 916c, respectively. Locking element 902c is in moveable relationship to plate 900c so that locking element 902c can be pre-installed to plate 900c prior to the insertion of bone screws into bone screw receiving holes 916c. During installation of the bone screws, locking element 902c can be slid to one side of the plate as shown in the top portion of the plate in FIG. 41 to allow for insertion of a first bone screw into a first bone screw receiving hole 916c on the opposite side of plate 900c. Locking element 902c is then moved to the opposite side of plate 900c to permit insertion of a second bone screw into the second bone screw receiving hole 916c. Locking element 902c is then moved to cover at least a portion of both first and second bone screws and can be locked in place by a screw 917c as shown in the middle and bottom portions of plate 900c in FIG. 41.

FIGS. 42 and 43 show a cervical plate 1000c with locking elements 1002c in accordance with another preferred embodiment of the present invention. Locking elements 1002c are installed to cover at least a portion of two bone screw receiving holes 1016c. In this embodiment, the bone screws are installed in bone screw receiving holes 1016c and locking element 1002c is placed over at least a portion of two bone screws to lock the bone screws. Locking element 1002c can be held in place with a screw 1017c that passes at least in part through opening 1003c in locking element 1002c and engages opening 1005c in plate 1000c to lock two bone screws 1048c to plate 1000c as shown in FIG. 43. Bone screws 1048c preferably have a leading end configured for insertion into the cervical spine and a head 1049c opposite the leading end that may be configured to contact locking element 1002c. By way of example only, bone screws 1048c may be configured to be in a fixed relationship to plate 1000c such as shown in FIG. 43.

FIG. 44 is a fragmentary cross sectional view of another preferred embodiment of a locking element 1002c' and bone screws 1048c'. Locking element 1002c' has a bottom surface adapted to cooperate with a rounded portion of head 1049c' of bone screws 1048c' and is adapted to hold bone screws 1048c' in an angular relationship to plate 1000c'. Examples of preferred fixed-angled locking elements are taught by Michelson the '550 patent hereby incorporated by reference herein. Locking element 1002c' may also permit movement of bone screw 1048c' relative to plate 1000c'. Locking element 1002c' may also be adapted to adjustably lock bone screws 1048c' in a variable angle relationship relative to plate 1000c'. Examples of preferred variable-angled locking elements are taught by Michelson in the '550 patent. The rounded portion of head 1049c' permits bone screws 1048c' to be in a moveable relationship, such as for example in a variable angular relationship to plate 1000*c'*. Other configurations are possible for the intended purpose and are within the broad scope of the present invention.

Various methods for using and installing the plates of the present invention are disclosed in the '550 and '721 patents to Michelson identified above, incorporated by reference herein.

Figure 45:
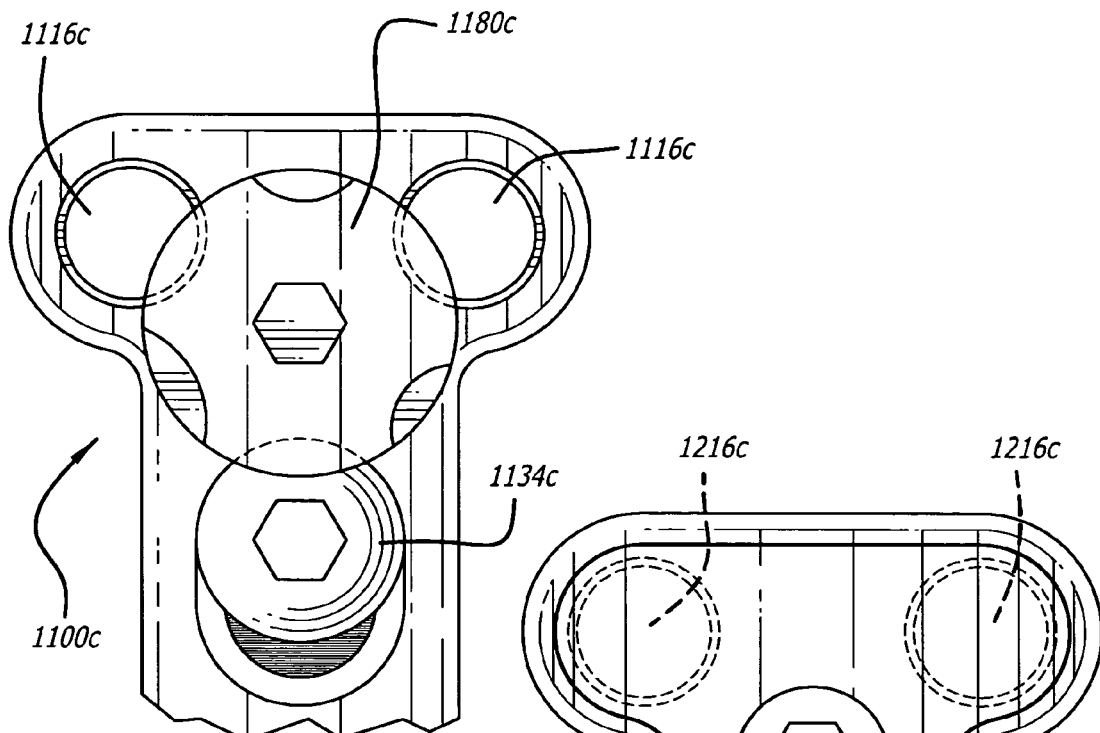
FIG. 45 is a fragmentary top plan view of another preferred embodiment of a plate and a locking element adapted to lock at least two bone screws and a fastener in accordance with the present invention.

FIG. 45 shows a plate 1100*c* and a locking element 1180*c* adapted to lock at least two bone screws and a fastener 1134*c* in accordance with the present invention. Preferably, locking element 1180*c* is configured to be preinstalled to plate 1100*c* prior to insertion of the bone screws in bone screw receiving holes 1116*c* and attachment of fastener 1134*c* to plate 1100*c*. Locking element 1180*c* has a first position that permits insertion of bone screws in respective bone screw receiving holes 1116*c* and installation and/or movement of fastener 1134*c*. Locking element 1180*c* has a second position that covers at least a portion of at least two bone screw receiving holes 1116*c* and fastener 1134*c* to lock at least two bone screws and fastener 1134*c* to plate 1100*c*. Locking element 1180*c* may preferably be configured to rotatably and/or slideably cover at least a portion of two bone screws in bone screw receiving holes 1116*c* and at least a portion of fastener 1134*c*.

Figure 46:
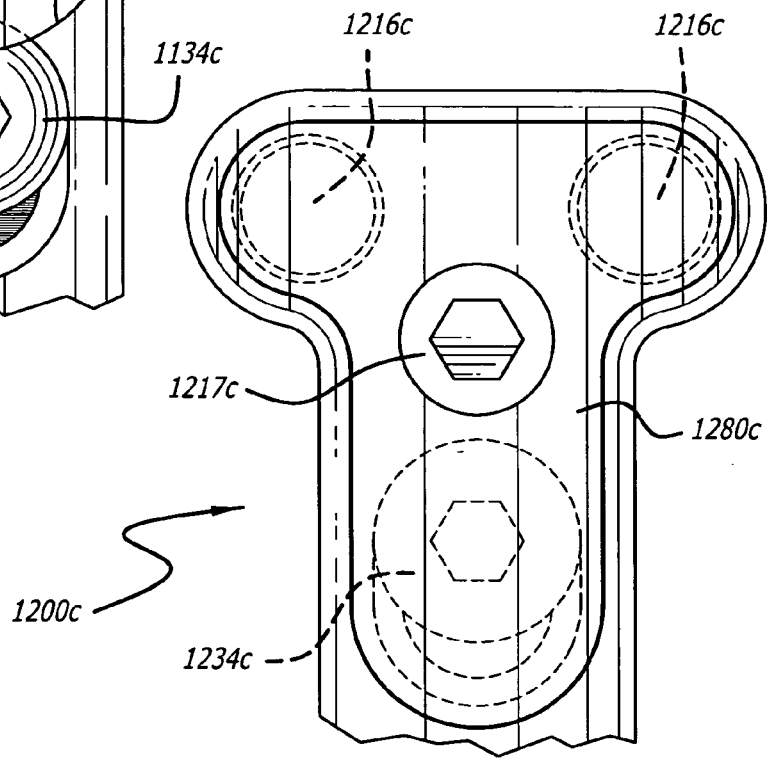
FIG. 46 is a fragmentary top plan view of another preferred embodiment of a plate and a locking element adapted to lock at least two bone screws and a fastener in accordance with the present invention.

FIG. 46 shows another preferred embodiment of a plate 1200*c* and locking element 1280*c* adapted to lock at least two bone screws and a fastener 1234*c* in accordance with the present invention. Locking element 1280*c* is configured to be installed to plate 1200*c* after insertion of bone screws in bone screw receiving holes 1216*c* and attachment of fastener 1234*c* to plate 1200*c*. Locking element 1280*c* is configured to cover at least a portion of at least two bone screw receiving holes 1216*c* and fastener 1234*c* to lock at least two bone screws and at least a portion of fastener 1234*c* to plate 1200*c*. Locking element 1280*c* is preferably attached to plate 1200*c* by a screw 1217*c* or by any other means suitable for the intended purpose.

The plates of present invention may include a bone screw system that allows the vertebrae to move toward an interposed bone graft, and each other if necessary, instead of keeping the vertebrae apart during the occurrence of the resorption phase of the creeping substitution process. For example, the '550 patent discloses three types of screw-plate-lock systems, which are themselves combinable with one another, as follows: (1) Passive Dynamic; (2) Self-Compressing; and (3) Active Dynamic and are incorporated by reference herein.

It is appreciated that for any of the embodiments of the plates described herein can be made of, treated, coated, combined with, comprised of, or used with any source of osteogenesis, fusion promoting substances, bone growth promoting materials, bone, bone derived substances or products, demineralized bone matrix, mineralizing proteins, ossifying proteins, bone morphogenetic proteins, hydroxyapatite, genes coding for the production of bone, substances other than bone, and bone including, but not limited to, cortical bone. The plates, screws, fasteners, and/or screw locks may also be combined with material and/or substance for inhibiting scar formation. The plates, screws, fasteners, and/or screw locks may be combined with an antimicrobial material and/or surface treated or coated to be antibacterial and/or antimicrobial, such as for example, by a silver coating. At least a portion of the bottom surface of the plates can preferably have a porous, and/or textured and/or roughened surface and may be coated with, impregnated with, or comprise of fusion promoting substances (such as bone morphogenetic proteins) so as to encourage the growth of bone along the underside of the plate from bone portion to bone portion. The textured bottom surface also provides a medium for retaining fusion promoting substances with which the bottom surface layer can be impregnated prior to installation. The bottom surface of the plate may be given the desired porous textured form by rough blasting or any other conventional technology, such as etching, plasma spraying, sintering, and casting for example. If porous so as to promote bone ingrowth, the bottom surface is formed to have a porosity or pore size in the order of 50-500 microns, and preferably 100-300 microns. Bone growth promoting substances with which the porous, textured bottom surface can be impregnated include, but are not limited to, bone morphogenetic proteins, hydroxyapatite, or hydroxyapatite tricalcium phosphate. The plate, screws, fasteners, and/or bone screw locks may include at least in part a resorbable and/or bioresorbable material which can further be impregnated with a bone growth material so that as the resorbable and/or bioresorbable material is resorbed by the body of the patient, the bone growth material is released, thus acting as a time release mechanism. The bioresorbable material may be, for example, at least in part bone. The plate of the present invention may be used in combination with a spinal fixation implant such as any object, regardless of material, that can be inserted into any portion of the spine, such as but not limited to interbody spinal implants, interbody spinal fusion implants, structural bone grafts, mesh, cages, spacers, staples, bone screws, plates, rods, tethers of synthetic cords or wires, or other spinal fixation hardware. The interbody spinal fusion implants may be at least in part bone, for example only, an allograft interbody bone graft. Alternatively, the spinal interbody spinal fusion implant may be at least in part artificial. At least one of the plate, screws, fasteners, and/or bone screw locks may be, if so desired, electrified for purposes of stimulating bone growth and contributing to bone fusion.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method comprising:
   providing a plate of appropriate length adapted to overlap at least an anterior portion of two adjacent vertebral bodies, the plate having at least a first plate segment adapted to be attached to one of the adjacent vertebral bodies to be fused and a second plate segment adapted to be attached to another one of the adjacent vertebral bodies to be fused, the first and second plate segments being in moveable relationship to one another along a longitudinal axis of the plate, the first and second plate segments being configured to couple together in cooperative relationship, the first plate segment and the second plate segment overlapping one another at least in part along the longitudinal axis of the plate, the plate having a fastener for coupling together the first and second plate segments, the fastener engaging at least one of the first and second plate segments;
   attaching the first plate segment by inserting, to a final installation depth, at least two bone screws through the first plate segment and into one of the vertebral bodies adjacent the disc space to be fused;
   attaching the second plate segment by inserting, to a final installation depth, at least two bone screws through the second plate segment and into the other of the vertebral bodies adjacent the disc space to be fused;
   tightening the fastener to one of the first and second plate segments to permit for limited motion of the first and second plate segments relative to one another; and after attaching the first and second plate segments to the vertebral bodies with the bone screws inserted to the final installation depth and with the fastener fully tightened to one of the first and second plate segments, permitting movement of the first and second plate segments relative to one another in a direction toward one another along the longitudinal axis of the plate in response to the natural tendency of the vertebral bodies to move toward one another, and resisting movement of the first and second plate segments in a direction away from one another along the longitudinal axis of the plate.

2. The method of claim 1, wherein the permitting movement of the first and second plate segments includes permitting movement of the first and second plate segments in only a single direction toward one another.

3. The method of claim 1, wherein the permitting movement of the first and second plate segments includes allowing but not causing the movement of the adjacent vertebral bodies by movement of the first and second plate segments of the plate.

4. The method of claim 3, wherein the permitting movement of the first and second plate segments includes the first and second plate segments being free to move toward one another.

5. The method of claim 1, wherein the permitting movement of the first and second plate segments includes limiting the movement of the first and second plate segments relative to one another to sequential increments along the longitudinal axis of the plate.

6. The method of claim 1, wherein the permitting movement of the first and second plate segments includes causing movement of the adjacent vertebral bodies by moving the first and second plate segments relative to one another.

7. The method of claim 6, wherein the causing movement of the adjacent vertebral bodies includes generating a compressive load across the disc space between the adjacent vertebral bodies.

8. The method of claim 7, wherein the permitting movement of the first and second plate segments includes the first and second plate segments being free to move toward one another.

9. The method of claim 6, wherein the causing movement of the adjacent vertebral bodies includes storing a compressive load across the disc space between the adjacent vertebral bodies.

10. The method of claim 9, wherein the permitting movement of the first and second plate segments includes the first and second plate segments being in fixed relationship to one another.

11. The method of claim 1, further comprising providing an instrument configured to cooperatively engage the fastener and at least a portion of at least one of the first and second plate segments, and utilizing the instrument to move the fastener and the first and second plate segments relative to one another along a mid-longitudinal axis of the plate.

12. The method of claim 11, wherein the utilizing the instrument to move the fastener and the first and second plate segments includes rotating the fastener at least in part with the instrument.

13. The method of claim 1, wherein the tightening the fastener to one of the first and second plate segments includes limiting the movement of the first and second plate segments relative to one another to sequential increments along the longitudinal axis of the plate.

14. The method of claim 1, wherein the tightening the fastener to one of the first and second plate segments includes tightening the fastener to cause the fastener to tighten to the first plate segment while permitting movement of the first and second plate segments relative to one another.

15. The method of claim 1, further comprising adjusting the overall length of the plate by moving the first and second plate segments relative to each other.

16. The method of claim 1, wherein the providing a plate of appropriate length includes selecting at least one of the first and second plate segments from a group of plate segments of various lengths.

17. The method of claim 1, wherein the providing a plate of appropriate length includes selecting at least one of the first and second plate segments from a group of plate segments of various configurations.

18. The method of claim 1, wherein the providing a plate of appropriate length includes providing a plate having at least a third plate segment.

19. The method of claim 18, wherein the providing a plate of appropriate length includes selecting at least one of the first, second, and third plate segments from a group of plate segments of various lengths.

20. The method of claim 18, wherein the providing a plate of appropriate length includes selecting at least one of the first, second, and third plate segments from a plurality of plate segments of various configurations.

21. The method of claim 1, further comprising locking at least one of the bone screws to the plate.

22. The method of claim 21, wherein the permitting movement of the first and second plate segments occurs prior to the locking at least one of the bone screws to the plate.

23. The method of claim 1, wherein the permitting movement of the first and second plate segments includes moving the first and second plate segments relative to one another before the inserting, to a final installation depth, at least two bone screws.

24. The method of claim 1, wherein the permitting movement of the first and second plate segments includes applying a compressive load to the adjacent vertebral bodies.

25. The method of claim 1, wherein the permitting movement of the first and second plate segments includes moving the first and second plate segments from a first position to a second position.

26. The method of claim 1, further comprising combining the plate with an interbody spinal fusion implant.

27. The method of claim 26, wherein the implant comprises at least in part bone.

28. The method of claim 26, wherein the implant is an allograft interbody bone graft implant.

29. The method of claim 26, wherein the implant is an artificial implant.

30. The method of claim 1, further comprising combining the plate with a fusion promoting substance.

31. The method of claim 30, wherein the fusion promoting substance is at least in part other than bone.

32. The method of claim 30, wherein the fusion promoting substance is at least in part bone.

33. The method of claim 30, wherein the fusion promoting substance is hydroxyapatite.

34. The method of claim 30, wherein the fusion promoting substance comprises bone morphogenetic protein.

35. The method of claim 30, wherein the fusion promoting substance comprises genes coding for the production of bone.

36. The method of claim 1, wherein the providing a plate of appropriate length further comprises providing bone screws for engaging the plate to the cervical spine, wherein at least a portion of one of the plate and the bone screws is a bioresorbable material.

37. The method of claim 36, wherein the bioresorbable material is at least in part bone.

38. The method of claim 1, further comprising combining the plate with a substance for inhibiting scar formation.

39. The method of claim 1, further comprising combining the plate with an antimicrobial material.

40. The method of claim 1, further comprising treating the plate with an antimicrobial material.

41. The method of claim 1, further comprising electrifying at least one of the plate and the bone screws for purposes of stimulating bone growth and contributing to bone fusion.

42. The method of claim 1, further comprising electrifying at least one of the plate, the fastener, and the bone screws for purposes of stimulating bone growth and contributing to bone fusion.

* * * * *